(12) United States Patent
Whittle et al.

(10) Patent No.: US 6,653,329 B1
(45) Date of Patent: Nov. 25, 2003

(54) GRANULATED PHARMACEUTICAL FORMULATIONS AND METHODS FOR MAKING THE SAME

(76) Inventors: Robert R. Whittle, 5006 Pine Needles Dr., Wilmington, NC (US) 28403; Frederick D. Sancilio, 2332 Ocean Point Dr., Wilimington, NC (US) 28405; Grayson Walker Stowell, 710 Darwin Dr., Wilmington, NC (US) 28405; Douglas John Jenkins, 6400 Purple Martin Ct., Wilmington, NC (US) 28411-8323; Linda B. Whittall, 2204 Splitbrook Ct., Wilmington, NC (US) 28411

( * ) Notice: Subject to any disclaimer, the term of this patent is extended or adjusted under 35 U.S.C. 154(b) by 0 days.

(21) Appl. No.: 10/439,865

(22) Filed: May 16, 2003

Related U.S. Application Data

(63) Continuation of application No. 10/189,659, filed on Jul. 3, 2002, which is a continuation of application No. 10/057,659, filed on Jan. 25, 2002, now Pat. No. 6,444,689, which is a continuation of application No. 09/645,145, filed on Aug. 24, 2000, now Pat. No. 6,369,087, which is a continuation-in-part of application No. 09/519,976, filed on Mar. 7, 2000, now Pat. No. 6,262,085.
(60) Provisional application No. 60/150,878, filed on Aug. 26, 1999.

(51) Int. Cl.$^7$ ............................................... A61K 31/44
(52) U.S. Cl. ........................................................ 514/338
(58) Field of Search ......................................... 514/338

(56) References Cited

U.S. PATENT DOCUMENTS

| | | | |
|---|---|---|---|
| 4,128,658 A | 12/1978 | Price et al. | .................. 424/285 |
| 4,255,431 A | 3/1981 | Junggren et al. | ............. 424/263 |
| 4,279,819 A | 7/1981 | Price et al. | ............ 260/326.5 S |
| 4,337,257 A | 6/1982 | Junggren et al. | ............. 424/263 |
| 4,508,905 A | 4/1985 | Junggren et al. | ............. 546/271 |

(List continued on next page.)

FOREIGN PATENT DOCUMENTS

| | | | | |
|---|---|---|---|---|
| DE | 4035455 A1 | 5/1992 | ......... | C07D/401/12 |
| EP | 0124495 A2 | 11/1984 | ......... | C07D/401/12 |
| EP | 0166287 B1 | 1/1986 | ......... | C07D/401/12 |
| EP | 0171372 A1 | 2/1986 | ......... | C07D/513/14 |
| EP | 0197013 A1 | 10/1986 | ......... | C07D/401/12 |
| EP | 0484265 A1 | 5/1992 | ......... | C07D/401/12 |
| EP | 0585722 A1 | 3/1994 | .......... | A61K/31/44 |
| JP | 61007281 A2 | 1/1986 | ......... | C07D/513/14 |
| JP | 61205211 | 9/1986 | .......... | A61K/31/44 |
| JP | 61271259 | 12/1986 | ............ | C07C/93/14 |
| JP | 02049774 A2 | 2/1990 | ......... | C07D/235/28 |
| JP | 06096581 | 4/1994 | ......... | G11C/114/01 |
| JP | 06316573 | 11/1994 | ......... | C07D/401/12 |
| WO | WO 89/03829 | 5/1989 | ......... | C07D/401/12 |
| WO | WO 92/08716 | 5/1992 | ......... | C07D/401/12 |
| WO | WO 93/21920 | 11/1993 | .......... | A61K/31/44 |
| WO | WO 94/02141 | 2/1994 | .......... | A61K/31/44 |
| WO | WO 94/27988 | 12/1994 | ......... | C07D/401/12 |
| WO | WO 95/01783 | 1/1995 | ............ | A61K/9/24 |
| WO | WO 95/01977 | 1/1995 | ......... | C07D/401/12 |
| WO | WO 95/18612 | 7/1995 | .......... | A61K/31/44 |
| WO | WO 95/32957 | 12/1995 | ......... | C07D/401/12 |
| WO | WO96/01622 | 1/1996 | ............ | A61K/9/24 |
| WO | WO 96/01623 | 1/1996 | ............ | A61K/9/26 |
| WO | WO 96/02535 | 2/1997 | ......... | C07D/401/12 |
| WO | WO 97/20851 | 6/1997 | ............ | C07F/7/08 |
| WO | WO 97/25030 | 7/1997 | ............ | A61K/9/46 |
| WO | WO 98/19668 | 5/1998 | ............ | A61K/9/50 |
| WO | WO 98/53803 | 12/1998 | ............ | A61K/9/28 |
| WO | WO 98/54171 | 12/1998 | ......... | C07D/401/12 |
| WO | WO 99/08500 | 2/1999 | | |

OTHER PUBLICATIONS

"The Mechanism of Action of the Gastric Acid Secretion Inhibitor Omeprazole," *Journal of Medicinal Chemistry* 29:8 1327–1329 (1986).

Beckett et al.; "4–Hydroxybenzoles: Preparation and Antibacterial Activities," *J. Pharm. and Pharmacol* 8:661–665 (1956).

Brändström et al.; "Structure activity relationships of substituted benzimidazoles," *Scandinavian Journal of Gastroenterology* 20:Supplemental 108 15–22 (1985).

Brändström et al.; "Chemical Reactions of Omeprazole and Omeprazole Analogues. I. A Survey of the Chemical Transformations of Omeprazole and its Analogues," *Acta Chemica Scandinavica* 43:536–548 (1989).

Brämdström et al.; "Chemical Reactions of Omeprazole and Omeprazole Analogues. II. Kinetics of the Reaction of Omeprazole in the Presence of 2–Mercaptoethanol," *Acta Chemica Scandinavica* 43:549–568 (1989).

Brändström et al.; "Chemical Reactions of Omeprazole and Omeprazole Analogues. III. Protolytic Behaviour of Compounds in the Omeprazole System," *Acta Chemica Scandinavica* 43:569–576 (1989).

Brändström et al.; "Chemical Reactions of Omeprazole and Omeprazole Analogues. IV. Reactions of Compounds of the Omeprazole System with 2–Mercaptoethanol," *Acta Chemica Scandinavica* 43:577–586 (1989).

Brändström et al.; "Chemical Reactions of Omeprazole and Omeprazole Analogues. V. The Reaction of N–Alkylated Derivatives of Omeprazole Analogues with 2–Mercaptoethanol," *Acta Chemica Scandinavica* 43:587–594 (1989).

Brändström et al.; "Chemical Reactions of Omeprazole and Omeprazole Analogues. VI. The Reactions of Omeprazole in the Absence of 2–Mercaptoethanol," *Acta Chemica Scandinavica* 43:595–611 (1989).

Clissold et al.; "Omeprazole A Preliminary Review of its Pharmacodynamic and Pharmacokinetic Properties, and Therapeutic Potential in Peptic Ulcer Disease and Zollinger–Ellison Syndrome," *Drugs* 32:15–47 (1986).

(List continued on next page.)

Primary Examiner—James H Reamer
(74) Attorney, Agent, or Firm—Myers Bigel Sibley & Sajovec, PA

(57) ABSTRACT

Compounds represented by formula (Ia) are disclosed by the invention, along with compositions and complexes thereof, optionally in combination with compounds of formula (Ib). Pharmaceutical formulations and methods of making and using such compounds are also disclosed.

45 Claims, No Drawings

U.S. PATENT DOCUMENTS

| | | | |
|---|---|---|---|
| 4,555,518 A | 11/1985 | Rainer | 514/338 |
| 4,596,795 A | 6/1986 | Pitha | 514/58 |
| 4,612,378 A | 9/1986 | Bosshard et al. | 548/170 |
| 4,620,008 A | 10/1986 | Brändström et al. | 546/271 |
| 4,628,098 A | 12/1986 | Nohara et al. | 546/271 |
| 4,636,499 A | 1/1987 | Brändström et al. | 514/222 |
| 4,725,691 A | 2/1988 | Brändström et al. | 546/172 |
| 4,727,064 A | 2/1988 | Pitha | 514/58 |
| 4,738,974 A | 4/1988 | Brändström | 514/338 |
| 4,753,955 A | 6/1988 | Matsuishi et al. | 514/338 |
| 4,772,619 A | 9/1988 | Adelstein et al. | 514/338 |
| 4,777,172 A | 10/1988 | Ife et al. | 514/234.5 |
| 4,786,505 A | 11/1988 | Lovgren et al. | 424/468 |
| 4,808,596 A | 2/1989 | Matsuishi et al. | 514/303 |
| 4,820,708 A | 4/1989 | Ife et al. | 514/232.8 |
| 4,840,799 A | 6/1989 | Appelgren et al. | 424/493 |
| 4,853,230 A | 8/1989 | Lovgren et al. | 424/466 |
| 5,021,443 A | 6/1991 | Bru-Magniez et al. | 514/394 |
| 5,045,321 A | 9/1991 | Makino et al. | 424/475 |
| 5,070,101 A | 12/1991 | Kaminski | 514/399 |
| 5,075,323 A | 12/1991 | Fain et al. | 514/338 |
| 5,093,132 A | 3/1992 | Makino et al. | 424/475 |
| 5,093,342 A | 3/1992 | Tomoi et al. | 514/328 |
| 5,096,893 A | 3/1992 | Pitha et al. | 514/58 |
| 5,106,863 A | 4/1992 | Hajos et al. | 514/395 |
| 5,124,158 A | 6/1992 | Ruwart et al. | 424/449 |
| 5,178,867 A | 1/1993 | Guittard et al. | 424/473 |
| 5,196,205 A | 3/1993 | Borody | 424/653 |
| 5,204,118 A | 4/1993 | Goldman et al. | 424/489 |
| 5,206,025 A | 4/1993 | Courteille et al. | 424/439 |
| 5,219,870 A | 6/1993 | Kim | 514/338 |
| 5,232,706 A | 8/1993 | Palomo Coll | 424/475 |
| 5,244,670 A | 9/1993 | Upson et al. | 424/439 |
| 5,246,714 A | 9/1993 | Dahlinder et al. | 424/497 |
| 5,288,506 A | 2/1994 | Spickett et al. | 424/498 |
| 5,294,439 A | 3/1994 | Yamasaka et al. | 424/78.01 |
| 5,294,629 A | 3/1994 | Machinami et al. | 514/366 |
| 5,304,540 A | 4/1994 | Blackburn et al. | 514/2 |
| 5,352,688 A | 10/1994 | Kaminski | 514/357 |
| 5,362,424 A | 11/1994 | Lee et al. | 264/4.3 |
| 5,374,730 A | 12/1994 | Slemon et al. | 546/271 |
| 5,385,739 A | 1/1995 | Debregeas et al. | 424/494 |
| 5,386,032 A | 1/1995 | Brändström | 546/271 |
| 5,391,752 A | 2/1995 | Hoerrner et al. | 546/271 |
| 5,399,700 A | 3/1995 | Min et al. | 546/271 |
| 5,417,980 A | 5/1995 | Goldman et al. | 424/464 |
| 5,433,959 A | 7/1995 | Makino et al. | 424/475 |
| 5,476,669 A | 12/1995 | Borody | 424/653 |
| 5,508,041 A | 4/1996 | Lee et al. | 424/451 |
| 5,514,660 A | 5/1996 | Zopf et al. | 514/25 |
| 5,518,730 A | 5/1996 | Fuisz | 424/426 |
| 5,536,735 A | 7/1996 | Takechi et al. | 514/338 |
| 5,571,811 A | 11/1996 | Heeres et al. | 514/252 |
| 5,578,732 A | 11/1996 | Kato et al. | 546/273.7 |
| 5,582,837 A | 12/1996 | Shell | 424/451 |
| 5,589,491 A | 12/1996 | Nakanishi et al. | 514/338 |
| 5,599,794 A | 2/1997 | Eek et al. | 514/29 |
| 5,616,593 A | 4/1997 | Patel et al. | 514/321 |
| 5,620,964 A | 4/1997 | Roth et al. | 514/53 |
| 5,622,717 A | 4/1997 | Fuisz | 424/488 |
| 5,629,305 A | 5/1997 | Eek et al. | 514/199 |
| 5,633,244 A | 5/1997 | Eek et al. | 514/199 |
| 5,635,520 A | 6/1997 | Uda | 514/338 |
| 5,637,592 A | 6/1997 | Heeres et al. | 514/252 |
| 5,639,478 A | 6/1997 | Makino et al. | 424/475 |
| 5,639,754 A | 6/1997 | Heeres et al. | 514/252 |
| 5,650,411 A | 7/1997 | Heeres et al. | 514/252 |
| 5,651,987 A | 7/1997 | Fuisz | 424/488 |
| 5,656,286 A | 8/1997 | Miranda et al. | 424/449 |
| 5,665,730 A | 9/1997 | Senn-Bilfinger et al. | 514/300 |
| 5,670,932 A | 9/1997 | Kizima | 340/384.6 |
| 5,686,588 A | 11/1997 | Yoo | 536/13.3 |
| 5,693,818 A | 12/1997 | Von Unge | 546/273.7 |
| 5,710,156 A | 1/1998 | Heeres et al. | 514/255 |
| 5,714,504 A | 2/1998 | Lindberg et al. | 514/338 |
| 5,719,161 A | 2/1998 | Rainer | 514/300 |
| 5,728,700 A | 3/1998 | Heeres et al. | 514/252 |
| 5,731,002 A | 3/1998 | Olovson et al. | 424/484 |
| 5,753,630 A | 5/1998 | Zopf et al. | 514/25 |
| 5,766,622 A | 6/1998 | Nelson | 424/440 |
| 5,776,765 A | 7/1998 | Graham et al. | 435/280 |
| 5,811,426 A | 9/1998 | Heeres et al. | 514/252 |
| 5,811,547 A | 9/1998 | Nakamichi et al. | 540/589 |
| 5,817,338 A | 10/1998 | Bergstrand et al. | 424/468 |
| 5,840,552 A | 11/1998 | Holt et al. | 435/118 |
| 5,846,562 A | 12/1998 | Yanai et al. | 424/451 |
| 5,859,030 A | 1/1999 | Kohl et al. | 514/338 |
| 5,877,192 A | 3/1999 | Lindberg et al. | 514/338 |
| 5,916,904 A | 6/1999 | Sato et al. | 514/338 |
| 5,929,244 A | 7/1999 | Von Unge | 546/273.7 |
| 5,948,789 A | 9/1999 | Larsson et al. | 514/299 |
| 6,262,085 B1 | 7/2001 | Whittle et al. | 514/338 |
| 6,262,086 B1 | 7/2001 | Whittle et al. | 514/338 |
| 6,268,385 B1 | 7/2001 | Whittle et al. | 514/338 |

OTHER PUBLICATIONS

Erlandsson; "Resolution of the enantiomers of omeprazole and some of its analogues by liquid chromatography on a trisphenylcarbomoylcellulose–based stationary phase. The effect of the enantiomers of omeprazole on gastric glands," *Journal of Chromatography* 532:305–319 (1990).

Lindberg et al.; "Structure–activity relationships of omeprazole analogues and their mechanism of action," *TIPS* 8:399–402 (Oct. 1987).

Maier et al.; "Diphenylethanediamine (DPEDA) Derivatives as Chiral Selectors: IV. A Comparison of 3,5–Dinitrobenzoylated (S,S)– and (S,R)–DPEDA–Derived Chiral Stationary Phases with Pirkle's Standard (R)–Phenylglycine–Derived Phase in Normal Phase HPLC," *Chirality* 6:116–128 (1994).

Marle et al.; "Separation of enantiomers using cellulase (CBH I) silica as a chiral stationary phase," *Journal of Chromatography* 582:233–248 (1991).

Marle et al.; "Chiral stationary phases based on intact and fragmented cellobiohydrolase I immobilized on silica," *Journal of Chromatography* 648:333–347 (1993).

Ohishi et al.; "Structure of 5–Methoxy–2–{[4–methoxy–3, 5–dimethyl–2–pyridinyl)methyl]sulfinyl }–1H–benzimidazole (Omeprazole)," *Acta Cryst.* C45:1921–1923 (1989).

Sachs et al.; "Gastric H,K–ATPase as Therapeutic Target," *Ann. Rev. Pharmacol. Toxicol.* 28:269–284 (1988).

Uray et al.; "Diphenylethanediamine derivatives as chiral selectors VIII. Influence of the second amido function on the high–performance liquid chromatographic enantioseparation characteristics of (N–3,5–dinitrobenzoyl)–diphenylethanediamine based chiral stationary phases," *Journal of Chromatography A* 799:1+2 67–81 (Mar. 1998).

von Unge et al.; "Stereochemical assignment of the enantiomers of omeprazole from X–ray analysis of a fenchyloxymethyl derivative of (+)–(R)–omeprazole," *Tetrahedron: Asymmetry* 8:12 1967–1970 (1997).

U.S. patent application No. 09/629,587 to Whittle, et al. entitled *Pharmaceutical Formulations*; filed Jul. 31, 2000.

U.S. patent application No. 09/628,840 to Whittle, et al. entitled *Method of Improving Bioavailability*; filed Jul. 31, 2000.

U.S. patent application No. 09/629,634 to Whittle, et al. entitled *Pharmaceutical Unit Dosage Form*; filed Jul. 31, 2000.

U.S. patent application No. 09/645,148 to Whittle, et al. entitled *Dry Blend Pharmaceutical Unit Dosage Form*; filed Aug. 24, 2000.

GRANULATED PHARMACEUTICAL FORMULATIONS AND METHODS FOR MAKING THE SAME

CROSS-REFERENCE TO RELATED APPLICATIONS

This application is a continuation of and claims priority from U.S. application Ser. No. 10/189,659, filed Jul. 3, 2002, which is a continuation of Ser. No. 10/057,659, now U.S. Pat. No. 6,444,689, filed Jan. 25, 2002, which is a continuation of Ser. No. 09/645,145 now U.S. Pat. No. 6,369,087, filed Aug. 24, 2000, which is a continuation-in-part of Ser. No. 09/519,976 now U.S. Pat. No. 6,262,085, filed Mar. 7, 2000, which claims the benefit of U.S. Provisional Application Serial No. 60/150,878, filed Aug. 26, 1999, the disclosures of all of which are hereby incorporated herein by reference in their entirety.

FIELD OF THE INVENTION

The invention generally relates to novel pharmaceutically active compounds, compositions comprising the same, pharmaceutical formulations of the same, methods of making the same, and methods of using the same.

BACKGROUND OF THE INVENTION

Various compounds used in inhibiting gastric acid secretion are known in the art and include a class of benzimidazole-substituted compounds, one of which is omeprazole. Omeprazole is currently commercially available in the formulation PRILOSEC®. In particular, U.S. Pat. No. 4,255,431 proposes such benzimidazole-substituted compounds generally described by the formula (III) in the '431 patent that allegedly encompasses omeprazole. Various methods of making these compounds are also proposed in the '431 patent.

European Patent No. 0 124 495 B1 proposes various salts of omeprazole, namely alkaline salts of the formula (I) in the '495 reference which includes lithium, sodium, potassium, magnesium, and calcium salts, along with methods of making the salts. The methods of forming these salts may involve employing a hydroxide, alkoxide, or amine base, or cation exchange using a metal salt Erlandsson, P., et al. *J. Chromatography*, 532 (1990) pp. 305–319 propose separating the (−) and (+) enantiomers of omeprazole utilizing chromatographic techniques. In this publication, the separation is proposed to take place on a preparative scale using a cellulose-based chiral phase, e.g., trisphenyl-carbamoyl cellulose coated on 3-aminopropyl silica. It is appreciated that other schemes and processes are available for this separation.

PCT Publication No. WO 94/27988 proposes salts of the single enantiomers of omeprazole and methods of making the same. The process involves separating the two stereoisomers of a diastereomer mixture of an acytoxymethyl-substituted benzimidazole compound described by the formula (IV) set forth in this published application, followed by solvolysis of each separated diastereomer in an alkaline solution. Salts of the single enantiomers are formed and isolated by neutralizing aqueous solutions of the salts of the single enantiomers of omeprazole with a neutralizing agent PCT Publication No. WO 96/02535 proposes a process for the enantioselective synthesis of single enantiomers of omeprazole or its alkaline salts. The process employs an oxidizing agent and a chiral titanium complex which may include a titanium(IV) compound.

PCT Publication No. WO 98/54171 proposes the magnesium salt of the (−) enantiomer of omeprazole. The '171 publication also proposes a method of synthesizing the above magnesium salt as well as the potassium, salt of (−) omeprazole that may be used as a suitable intermediate for preparing the magnesium salt The potassium salt is taught to be useful in treating gastrointestinal diseases.

U.S. Pat. No. 5,386,032 to Brandstrom processes an improved method for synthesizing omeprazole which involves reacting 5-methoxy-2-[(4-methoxy-3,5-dimethyl-2-pyridinyl)-methyl-thio]-1H benzimidazole with m-chicroperoxybenzoic acid in a methylene chloride solution.

The teachings regarding the methods of making omeprazole as referred to in these references, salts thereof, enantiomers thereof, and salts of the enantiomers, as well as formulations which may include these compounds, all rely on the chemical structure of omeprazole being accurately determined and the referenced compound or compounds being consistently prepared using the referenced techniques. More specifically, a methoxy group on the benzimidazole ring has been explicitly stated in the literature to be present at the 5-position, in omeprazole, a racemic mixture, and an optically pure isomer of omeprazole designated as esomeprazole or s-omeprazole. Applicants have now unexpectedly discovered the complexity of omeprazole and the relative bioactivity of each of its previously undiscovered and undisclosed attributes. More specifically, Applicants have confirmed that the methods of the prior art do not yield a single compound having the methoxy group in the 5-position on the benzimidazole ring as previously taught, nor do all of the methods of the prior art yield consistent results. In fact, omeprazole as conventionally referred to as a bulk drug substance (in its solid state) has been discovered to be present in the form of two pharmaceutically active compounds having the methoxy group on the benzimidazole ring at the 6- and 5-positions. Additionally, Applicants have discovered the presence of a second chiral location at the pyridine ring plane in each of the two compounds such that each compound has two positional isomers and four diastereomers. Therefore, the present invention provides these individual compounds, along with any salts, hydrates, solvates, combinations thereof, and polymorphs thereof, compositions of the above, and methods of making the same that are not taught or suggested by the prior art, pharmaceutical formulations of the compounds, compositions, and complexes of the present invention, and methods for using the same.

SUMMARY OF THE INVENTION

The present invention generally provides compounds represented by formulae (Ia) and (Ib), compositions of compounds represented by formulae (Ia) and (Ib) which typically are co-crystallized in part or in whole, one or more pharmaceutically acceptable salts, solvates, hydrates, or combinations of such compounds and compositions, and complexes thereof. Individual diastereomers of the above and combinations of such diastereomers are also provided. The invention also provides compositions and pharmaceutical formulations of the above. Methods of making the above are also provided by the present invention.

More specifically, the present discovery pertains to novel compounds, particularly compounds of the present invention that have a methoxy moiety at the 6-position on the benzimidazole ring, and compositions comprising compounds having methoxy groups at the 5- and 6-positions, respectively. It is unexpected that these individual compounds are present in the solid state and, furthermore, in co-crystalline form. Ratios of the above isomers can be manipulated, and novel compounds encompassing a myriad of ratios of diastereomers of such compounds are also provided. Each of these is described in greater detail hereinafter.

The invention also provides methods of administering such compounds, compositions, and complexes of the present invention to a mammal in need of treatment, typically for the treatment of gastric acid related diseases.

As used herein, the plural forms of the terms salts, solvates, hydrates, and the like, refer to both two singular and plural, e.g., a single salt, multiple salts, singular solvate, multiple solvates, singular hydrate, multiple hydrates, and the like, and combinations thereof of the term.

These and other aspects of the invention are set forth in greater detail herein.

DETAILED DESCRIPTION OF THE PREFERRED EMBODIMENTS

The invention is described hereinbelow in greater detail with reference to its preferred embodiments. These embodiments, however, are set forth to illustrate the invention and are not to be construed as a limitation thereof, the invention being defined by the claims.

In one aspect, the invention relates to a compound represented by formula (Ia) as set forth below. Applicants have unexpectedly discovered that this compound, in solid state, has not been taught or suggested by the prior art Additionally, it has been unexpectedly discovered that this newly-discovered compound has two distinct chiral locations in solid state: (1) a chiral center at the sulfoxide group and (2) a chiral plane located at the pyridinal moiety of such compound. More specifically, it has been furthered discovered that when $R_4$ is alkoxy, or other appropriate substituents, such group is locked into a fixed configuration generally perpendicular to the pyridine plane by the steric hindrance of the two substituents located in the $R_3$ and $R_5$ positions providing $R_3$ and $R_5$ are not hydrogen. The locked orientation of this substituent in solid state, preferably methoxy, gives rise to a chiral plane in which part or all of such substituent, preferably the methyl substituent of such preferred methoxy group, is located either above or below the unsymmetricalyridine chiral plane. However, in solution the $R_4$ alkoxy substituent of compounds represented by formulae Ia and Ib herein are not necessarily locked in such orientation.

The compound represented by formula (Ia) is as follows:

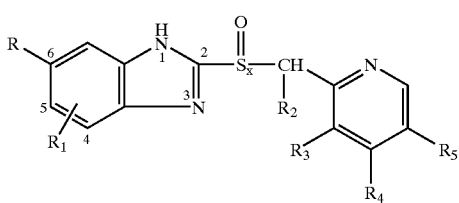

(Ia)

wherein:
$S_x$ represent a chiral sulfur atom comprising at least one of the diastereomers represented by $S_{xa}$ and $S_{xb}$, wherien $S_{xa}$ is the (−) enantiomer and $S_{xb}$ is the (+) enantiomer,
R is alkoxy;
$R_1$ is selected from the group consisting of hydrogen, alkyl halogen, carboalkoxy, alkoxy, and alkanoyl;

$R_2$ is hydrogen or alkyl; and
$R_3$, $R_4$, and $R_5$ may be the same or different and are each selected from the group consisting of hydrogen, alkyl, alkoxy, and alkoxyalkoxy,
wherein when $R_4$ is alkoxy and neither $R_3$ nor $R_5$ are hydrogen, the alkyl substituent of such alkoxy group is selected from the group consisting of at least one of the enantiomers represented by $R_{4q}$ and $R_{4z}$; wherein $R_{4q}$ is the (−) enantiomer and lies above the chiral plane; and $R_{4z}$ is the (+) enantiomer and lies below the chiral plane;

or one or more pharmaceutically acceptable salts, solvates, hydrates, or combinations thereof of said compound(s) represented by formula (Ia).

In one embodiment, all of $R_3$, $R_4$, and $R_5$ are not hydrogen. In another embodiment, when two of $R_3$, $R_4$, and $R_5$ are hydrogen, the third is not methyl. The compound represented by formula (Ia) is preferably present in solid state.

The term "alkoxy" preferably refers to alkoxy groups having up to 5 carbon atoms more, preferably up to 3 carbon atoms such as, for example, methoxy, ethoxy, n-propoxy, or isopropoxy.

The term "carboalkoxy" preferably refers to carboalkoxy groups having up to 5 carbon atoms such as, for example, carbomethoxy, carboethoxy, carbopropoxy, and carbobutoxy.

The term "alkoxyalkoxy" preferably refers to alkoxyalkoxy groups having up to 5 carbon atoms such as, for example, methoxymethoxy, ethoxyethoxy, and the like. Methoxyethoxy and the like is also encompassed under this definition.

The term "alkyl" preferably refers to alkyl groups having up to 7 carbon atoms, more preferably up to 4 carbon atoms, and is thus preferably selected from methyl, ethyl, n-propyl, isopropyl, n-butyl, or isobutyl.

The term "halogen" refers to chlcro, bromo, fluoro, or iodo.

The term "alkanoyl" preferably refers to alkanoyl, groups having up to 4 carbon atoms. Examples include formyl, acatyl, and propionyl.

In a preferred embodiment, R is methoxy; $R_1$ is hydrogen; $R_2$ is hydrogen; $R_3$ is methyl; $R_4$ is methoxy; and $R_5$ is methyl.

Applicants note that throughout the provisional application upon which priority is claimed, the $R_1$ substituent was referred to as being in the 4-position in the compound represented by formula (Ia). For the purposes of the present application, the benzimidazole ring is numbered such that the $R_1$ substituent of the compound of formula (Ia) is present in the 6-position. The purpose of this change in numbering is to better conform to generally accepted chemical nomenclature and has no bearing on the location of substituents of compounds described in the provisional application or herein.

In various embodiments of the present invention, the compounds represented by formula (Ia) may be present in the form of various individual diastereomers including, for example:
(a) $S_{xa}$—$R_{4q}$;
(b) $S_{xa}$—$R_{4z}$;
(c) $S_{xb}$—$R_{4q}$; and
(d) $S_{xb}$—$R_{4z}$,
or pharmaceutically acceptable salts, solvates, hydrates, or combinations thereof. These descriptions are provided to permit differentiation of the various stereoisomers (diastereomers) throughout this document, and represent the following in standard chemical nomenclature:

(a) $S_{xa}$—$R_{4q}$, (S)—(S), or (−)-(−);
(b) $S_{xa}$—$R_{4z}$, (S)—(R), or (−)-(+);
(c) $S_{xb}$—$R_{4q}$, (R)—(S), or (+)-(−); and
(d) $S_{xb}$—$R_{4z}$, (R)—(R), or (+)-(+).

For the purposes of the present invention, the term "enantiomer" refers to diastereomer pairs that are non-superimposable mirror images of each other. The term "enantomeric pair" as referenced herein refers t pairs of enantiomers that generate a racemic mixture. Examples of enantiomeric pairs include: (1) S—S and R—R, and (2) S—S and R—S of the compounds of formulae (Ia) and/or (Ib). The term "(−) enantiomer" may encompass any of the diastereomers S—S or S—R and pairs thereof. The term "(+) enantiomer" may encompass any of the diastereomers R—R and R—S and pairs thereof.

Preferred embodiments of various species of the compound represented by formula (Ia) are represented by the formulae (Iai), (Iaii), (Iaiii), and (Iaiv):

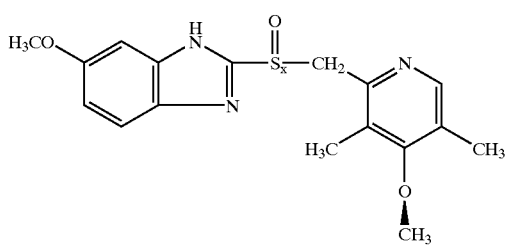
(Iai)

wherein $S_x$ is $S_{xa}$, or one or more pharmaceutically acceptable salts, solvates, hydrates, or combinations thereof of said compound represented by formula (Iai):

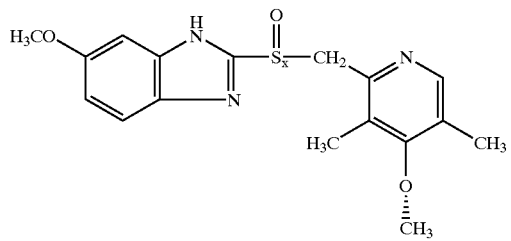
(Iaii)

wherein $S_x$ is $S_{xa}$, or one or more pharmaceutically acceptable salts, solvates, hydrates, or combinations thereof of said compound represented by formula (Iaii);

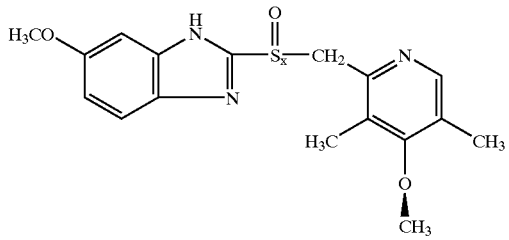
(Iaiii)

wherein $S_x$ is $S_{xb}$, or one or more pharmaceutically acceptable salts, solvates, hydrates, or combinations thereof of said compound represented by formula (Iaiii); and

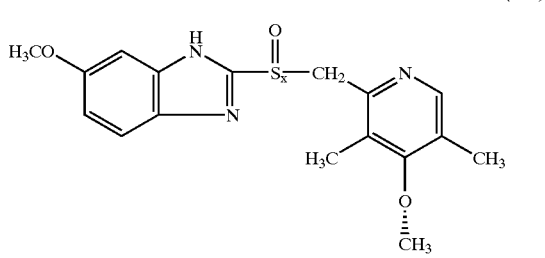
(Iaiv)

wherein $S_x$ is $S_{xb}$, or one or more pharmaceutically acceptable salts, solvates, hydrates, or combinations thereof of said compound represented by formula (Iaiv).

The above compounds may be made by various methods including those set forth in greater detail herein. Other methods may be also be employed.

In another aspect, the invention relates to a composition comprising two or more compounds represented by the formula (Ia) set fort herein. In particular, and as discussed in greater detail herein, Applicants provide any combination of any of the four diastereomers in varying ratio amounts.

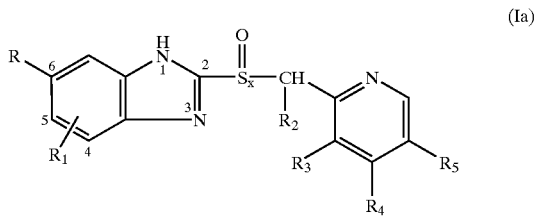
(Ia)

wherein:
$S_x$ represents a chiral sulfur atom comprising at least one of the enantiomers represented by $S_{xa}$ and $S_{xb}$, wherein $S_{xa}$ is the (−) enantiomer and $S_{xb}$ is the (+) enantiomer,
R is alkoxy;
$R_1$ is selected from the group consisting of hydrogen, alkyl, halogen, carboalkoxy, alkoxy, and alkanoyl;
$R_2$ is hydrogen or alkyl; and
$R_3$, $R_4$, and $R_5$ may be the same or different and are each selected from the group consisting of hydrogen, alkyl, alkoxy, and alkoxyalkoxy,
wherein when $R_4$ is alkoxy and neither $R_3$ nor $R_5$ are hydrogen, the alkyl substituent of such alkoxy group is selected from the group consisting of at least one of the enantiomers represented by $R_{4q}$ and $R_{4z}$, wherein $R_{4q}$ is the (−) enantiomer and lies above the chiral plane; and $R_{4z}$ is the (+) enantiomer and lies below the chiral plane;
or one or more pharmaceutically acceptable salts, solvates, hydrates, or combinations thereof of said compounds represented by formula (Ia).

The compositions of two or more compounds may contain various amounts of the enantiomers $S_{xa}$, $S_{xb}$, $R_{4q}$, and $R_{4z}$. Methods for making the various enantiomers and diastereomers are set forth herein. In one embodiment, for example, each of the diastereomers represented by $S_{xa}$ and $S_{xb}$ in the compounds represented by formula (Ia) is present in a range from about 0 percent (w/w) to about 100 percent (w/w) such that the total percentage of the sum of $S_{xa}$ and $S_{xb}$ equals about 100 percent (w/w). In another embodiment, each of the enantiomers represented by $R_{4q}$ and $R_{4z}$ is present in a range from about 0 percent (w/w) to about 100 percent (w/w) such that when the total percentage of the sum of $R_{4q}$ and $R_{4z}$ equals about 100 percent (w/w).

In the above composition, each of the at least two compounds may be the same or different. Any number of combinations of individual diastereomers or combinations thereof of the compound represented by formula (Ia) may be present in the composition. Examples of such diastereomers are as follows: $S_{xa}$—$R_{4q}$; $S_{xa}$—$R_{4z}$; $S_{xb}$—$R_{4q}$; and $S_{xb}$—$R_{4z}$, or pharmaceutically acceptable salts, solvates, hydrates, or combinations thereof of the compound represented by formula (Ia).

In various embodiments, the above diastereomers or combinations thereof may be present in such a manner wherein the composition forms a racemic mixture. In other embodiments, the diastereomers may be present in such a manner wherein the composition does not form a racemic mixture. In one embodiment, the diastereomers of each of the compounds represented by formula (Ia) in the composition are $S_{xa}$—$R_{4q}$ and $S_{xb}$—$R_{4z}$ or pharmaceutically acceptable salts, solvates, hydrates, or combinations thereof of the compound represented by formula (Ia). These diastereomers may be present in amounts such that the composition forms a racemic mixture, or alternatively, these diastereomers may be present in amounts such that the composition does not form a racemic mixture. In another embodiment, the composition comprising $S_{xa}$—$R_{4q}$ and $S_{xb}$—$R_{4z}$ or one or more pharmaceutically acceptable salts, solvates, hydrates, or combinations thereof of the compound represented by formula (Ia) may be essentially free of compounds represented by formula (Ia) having diastereomers $S_{xa}$—$R_{4z}$ and $S_{xb}$—$R_{4q}$. When used in reference to individual diastereomers throughout this document, the term "essentially free" means that a composition comprising compounds of the present invention having such specified diastereomers and diastereomer pairs containing not more than about 5 percent concentration of compounds having non-specfied diastereomers and/or diastereomer pairs. In one embodiment, for example, compounds having these diastereomer ($S_{xa}$—$R_{4q}$ and $S_{xb}$—$R_{4z}$) will generally form compositions in crystalline form that are free or, more typically, essentially free of compounds having the diastereomers of $S_{xa}$—$R_{4z}$ and $S_{xb}$—$R_{4q}$.

In another embodiment, the diastereomers of each of the compounds represented by formula (Ia) in the composition are $S_{xa}$—$R_{4q}$ and $S_{xa}$—$R_{4z}$, or one or more pharmaceutically acceptable salts, solvates, hydrates, or combinations thereof of the compound represented by formula (Ia). In one example of this embodiment, the above composition is essentially free of compounds represented by formula (Ia) having diastereomers represented by $S_{xb}$—$R_{4q}$ and/or $S_{xb}$—$R_{4z}$. Typically, this composition is in the form of an oil which, using the technique taught hereinafter, may form a crystalline, generally a microcrystalline, composition. Such a crystalline composition may be formed, typically with significant difficulty, by various techniques, but it is preferred to form a "salt" of such composition which may be formed independently or, preferably, in situ, as described hereinafter. Contrary to teachings in the art, methods typically known to the ordinarily skilled artisan may or may not form a salt of compounds and compositions of the present invention, but may, in fact, form previously unknown and unrecognized complexes which are described herein. As used herein, the term "salt" or "salts", in addition to its traditional meaning in the art, also refers to such complexes, except as otherwise set forth herein.

In another embodiment, the diastereomers of each of the compounds represented by formula (Ia) in the composition are $S_{xb}$—$R_{4z}$ and $S_{xb}$—$R_{4q}$, or one or more pharmaceutically acceptable salts, solvates, hydrates, or combinations thereof of the compound represented by formula (Ia). In one example of this embodiment, the above composition is essentially free of compounds represented by formula (Ia) having diastereomers represented by $S_{xa}$—$R_{4z}$ and/or $S_{xa}$—$R_{4q}$. Otherwise, a salt of such composition may also be formed independently or, preferably, in situ, as described hereinafter.

In another embodiment, the diastereomers of each of the compounds represented by formula (Ia) in the composition is $S_{xa}$—$R_{4q}$ or one or more pharmaceutically acceptable salts, solvates, hydrates, or combinations thereof of the compound represented by formula (Ia). In an example of this embodiment, the composition is optically pure. The term "optically pure" has the meaning generally accepted in the art, and also includes given or selected diastereomers and/or diastereomer pairs being essentially free of other compounds and/or impurities that would substantially affect the optical rotation of the composition. In another example of this embodiment, the composition is essentially free of compounds represented by the formula (Ia) having diastereomers $S_{xa}$—$R_{4z}$, $S_{xb}$—$R_{4q}$, and $S_{xb}$—$R_{4z}$.

In another embodiment, the diastereomers of each of the compounds represented by formula (Ia) in the composition is $S_{xa}$—$R_{4z}$ or one ore more pharmaceutically acceptable salts, solvates, hydrates, or combinations thereof of the compound represented by formula (Ia). In one example of this embodiment, the composition is optically pure as defined herein. In another example of this embodiment, the composition is essentially free of compounds represented by the formula (Ia) having diastereomers $S_{xa}$—$R_{4q}$, $S_{xb}$—$R_{4q}$, and $S_{xb}$—$R_{4z}$.

In another embodiment, the diastereomers of each of the compounds represented by formula (Ia) in the composition is $S_{xb}$—$R_{4q}$ or one or more pharmaceutically acceptable salts, solvates, hydrates, or combinations thereof of the compound represented by formula (Ia). In an example of this embodiment, the composition is optically pure as preferably defined herein. In another example of this embodiment, the composition is essentially free of compounds represented by the formula (Ia) having diastereomers $S_{xa}$—$R_{4q}$, $S_{xa}$—$R_{4z}$, and $S_{xb}$—$R_{4z}$.

In another embodiment, the diastereomers of each of the compounds represented by formula (Ia) in the composition is $S_{xb}$—$R_{4z}$ or one or more pharmaceutically acceptable salts, solvates, hydrates, or combinations thereof of the compound represented by formula (Ia). In an example of his embodiment, the composition is optically pure. In another example of this embodiment, the composition is essentially free of compounds represented by the formula (Ia) having diastereomers $S_{xa}$—$R_{4q}$, $S_{xa}$—$R_{4z}$, and $S_{xb}$—$R_{4q}$.

Compounds of the present invention comprising each of the individual diastereomers represented by $S_{xa}$—$R_{4q}$, $S_{xa}$—$R_{4z}$; $S_{xb}$—$R_{4q}$; and $S_{xb}$—$R_{4z}$ may individually provide significantly greater biological activity for the prevention and/ or treatment of the disease states discussed hereinbelow than compounds of the present invention having combinations of such diastereomers.

Accordingly, methods of the present invention provide for improved biological activity/efficacy (e.g. inhibition of gastric acid secretions and, thus, treatment of gastric acid disturbances in mammals, including humans) of pharmaceutically active compounds omeprazole and esomeprazole, as presently known in the art, comprising administering to such mammals in need of treatment a non-toxic, therapeutically effective amount of any composition of the present invention comprising compounds or compositions of the present invention having individual diastereomers comprising $S_{xa}$—$R_{4q}$; $S_{xa}$—$R_{4z}$; $S_{xb}$—$R_{4q}$; or $S_{xb}$—$R_{4z}$, or one or more pharmaceutically acceptable salts, solvates, hydrates, or combinations thereof. Also provided are such methods wherein said compounds or complexes of the present invention having said selected individual diastereomer pair essentially free of compounds of the present invention having diastereomer pairs other than said selected individual diastereomers. A preferred diastereomer is $S_{xa}$—$R_{4q}$, and an especially preferred diastereomer is $S_{xa}$ $R_{4z}$.

In addition, the present invention also provides for improved biological activity/efficacy of compositions of the present invention comprising compounds or compositions of the present invention having two or more diastereomers comprising $S_{xa}$—$R_{4q}$; $S_{xa}$—$R_{4z}$; $S_{xb}$—$R_{4q}$; or $S_{xb}$—$R_{4z}$, comprising administering to mammals, including humans, in need of inhibition of gastric acid secretion and, thus, treatment of gastric acid disease states, any composition of the present invention comprising compounds, compositions, or complexes of the present invention having an individual diastereomer selected from the group consisting of $S_{xa}$—$R_{4q}$; $S_{xa}$—$R_{4z}$; $S_{xb}$—$R_{4q}$; and $S_{xb}$—$R_{4z}$, or one or more pharmaceutically acceptable salts, solvates, hydrates, or combinations therof. Also provided are such methods wherein said compounds, compositions, or complexes of the present invention having said selected individual diastereomer essentially free of compounds of the present invention having diastereomers other than said selected individual diastereomer.

In any of the above embodiments, each of the two or more compounds represented by formula (Ia), which each of said compounds may be the same or different except as otherwise designated, are preferably compounds of the formulae represented by (Iai), (Iaii), (Iaiii), or (Iaiv):

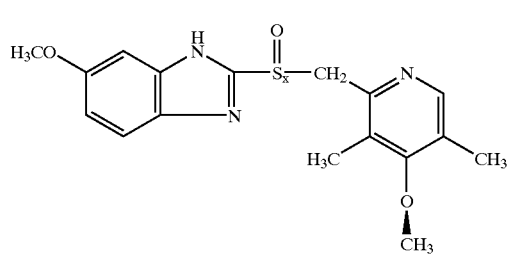

(Iai)

wherein $S_x$ is $S_{xa}$, or one or more pharmaceutically acceptable salts, solvates, hydrates, or combinations thereof of the compound represented by formula (Iai);

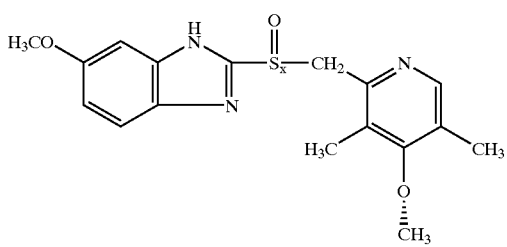

(Iaii)

wherein $S_x$ is $S_{xa}$, or one or more pharmaceutically acceptable salts, solvates, hydrates, or combinations thereof of the compound represented by formula (Iaii);

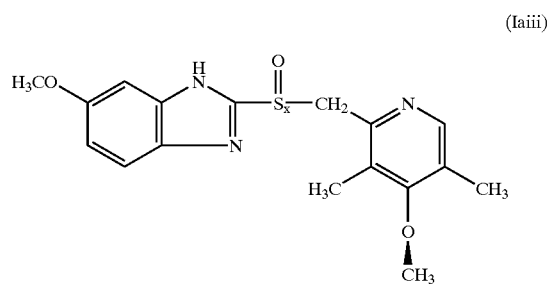

(Iaiii)

wherein $S_x$ is $S_{xb}$, or one or more pharmaceutically acceptable salts, solvates, hydrates, or combinations thereof of the compound represented by formula (Iaiii); and

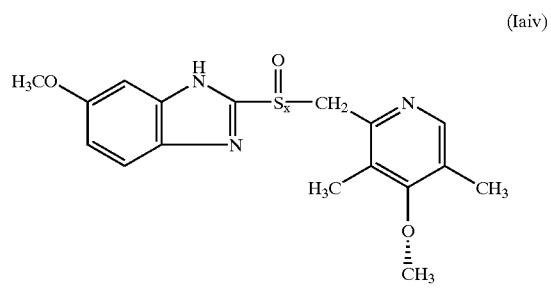

(Iaiv)

wherein $S_x$ is $S_{xb}$, or one or more pharmaceutically acceptable salts, solvates, hydrates, or combinations thereof of the compound represented by formula (Iaiv). Other species of the compound represented by the formula (Ia) may be employed for the purpose of the invention.

Any of the embodiments encompassing the compound(s) represented by formula (Ia), as individual compounds or in compositions and/or complexes of the present invention, or one or more pharmaceutically acceptable salts, solvates, hydrates, or combinations thereof, are typically present in crystalline form, in part or in whole.

In another aspect, the invention also provides compositions of active pharmaceutical ingredient ("API") comprising any of the compounds, compositions, or complexes of the present invention, each of which may be present in crystalline form, in part or in whole. Advantageously, each such compositions and/or complexes comprising compounds represented by formula (Ia) may also include any one or more of the specific compounds represented by formulae (Iaid, (Iaii), (Iaiii), and (Iaiv), or pharmaceutically acceptable salts, solvates, hydrates, polymorphs, or combinations thereof, whether in crystalline form, amorphous forms or a combination thereof. Each can be used as the bases for any such API composition.

The invention also provides any of the compositions set forth herein comprising the two or more compounds of formula (Ia), that may be the same or different, being essentially free of compounds represented by formula (Ib):

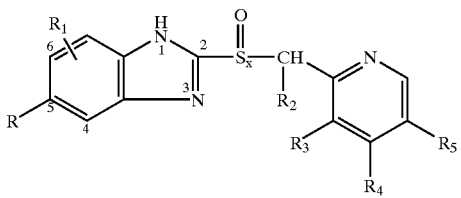

(Ib)

wherein:
S$_x$ represents a chiral sulfur atom comprising at least one of the enantiomers represented by S$_{xa}$ and S$_{xb}$, wherein S$_{xa}$ is the (−) enantiomer and S$_{xb}$ is the (+) enantiomer;
R is alkoxy;
R$_1$ is selected from the group consisting of hydrogen, alkyl, halogen, carboalkoxy, alkoxy, and alkanoyl;
R$_2$ is hydrogen or alkyl; and
R$_3$, R$_4$, and R$_5$ may be the same or different and are each selected from the group consisting of hydrogen, alkyl, alkoxy, and alkoxyalkoxy,
wherein when R$_4$ is alkoxy and neither R$_3$ nor R$_5$ are hydrogen, the alkyl substituent of such alkoxy group is selected from the group consisting of at least one of the enantiomers represented by R$_{4q}$ and R$_{4z}$; wherein R$_{4q}$ is the (−) enantiomer and lies above the chiral plane; and R$_{4z}$ is the (+) enantiomer and lies below the chiral plane;
or one or more pharmaceutically acceptable salts, solvates, hydrates, or combinations thereof of said compounds represented by formula (Ib).

For the purposes of the invention, the term "pure" refers to compounds of the formula (Ia) being present in an amount such that other components, including compounds represented by formula (Ib), are present in amounts generally below limits detectable by conventional technology, preferably compounds of formula (Ia) being present in an amount of at least about 97–98 percent purity (w/w). As used herein, the term "essentially free" of compounds of formula (Ib) refers to the compound(s) represented by formula (Ia) preferably being present in an amount that is less than about 5 percent (w/w), more preferably about 4 percent (w/w) or less, of such compounds represented by formula (Ib) in such composition.

In another aspect, and as discussed in greater detail herein, Applicants have discovered that the compounds of formulae (Ia) and (Ib) are typically formed in a manner such that they are present in the same crystalline lattice (i.e., the compounds co-crystallize, in part or in whole, from solution). Thus, in this aspect, the invention further relates to compositions comprising a one to one ratio of molecules of:
(a) a compound represented by formula (Ia):

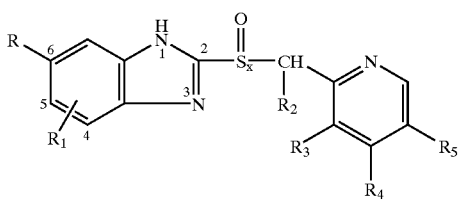

(Ia)

wherein:
S$_x$ represents a chiral sulfur atom comprising at least one of the enantiomers represented by S$_{xa}$ and S$_{xb}$, wherein S$_{xa}$ is the (−) enantiomer and S$_{xb}$ is the (+) enantiomer;
R is alkoxy;
R$_1$ is selected from the group consisting of hydrogen, alkyl, halogen, carboalkoxy, alkoxy, and alkanoyl;
R$_2$ is hydrogen or alkyl; and
R$_3$, R$_4$, and R$_5$ may be the same or different and are each selected from the group consisting of hydrogen, alkyl, alkoxy, and alkoxyalkoxy,
wherein when R$_4$ is alkoxy and neither R$_3$ or R$_5$ are hydrogen, the alkyl substituent of such alkoxy group is selected from the group consisting of at least one of the enantiomers represented by R$_{4q}$ and R$_{4z}$ wherein R$_{4q}$ is the (−) enantiomer and lies above the chiral plane; and R$_{4z}$ is the (+) enantiomer and lies below the chiral plane, or one or more pharmaceutically acceptable salts, solvates, hydrates, or combinations thereof, In combination with, and preferably co-crystallized with:
(b) a compound represented by formula (Ib):

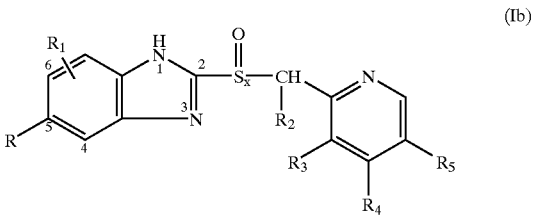

(Ib)

wherein:
S$_x$ represents a chiral sulfur atom comprising at least one of the enantiomers represented by S$_{xa}$ and S$_{xb}$, wherein S$_{xa}$ is the (−) enantiomer and S$_{xb}$ is the (+) enantiomer;
R is alkoxy;
R$_1$ is selected from the group consisting of hydrogen, alkyl, halogen, carboalkoxy, alkoxy, and alkanoyl;
R$_2$ is hydrogen or alkyl; and
R$_3$, R$_4$, and R$_5$ may be the same or different and are each selected from the group consisting of hydrogen, alkyl, alkoxy, and alkoxyalkoxy,
wherein when R$_4$ is alkoxy and neither R$_3$ nor R$_5$ are hydrogen, the alkyl substituent of such alkoxy group is selected from the group consisting of at least one of the enantiomers represented by R$_{4q}$ and R$_{4z}$, wherein R$_{4q}$ is the (−) enantiomer and lies above the chiral plane; and R$_{4z}$ is the (+) enantiomer and lies below the chiral plane;
wherein R of a compound represented by formula (Ia) and (Ib) each is preferably the same alkoxy substituent; and
each substituent of S$_x$, R$_1$, R$_2$, R$_3$, R$_4$, and R$_5$ of a compound represented by each of formulae (Ia) and (Ib) are preferably the same;
or one or more pharmaceutically acceptable salts, solvates, hydrates, or combinations thereof of the composition. The compounds represented by formulae (Ia) and (Ib) may be the same or different relative to the pyridine enantiomers, but should be the same for sulfoxide enantiomers.

Any of the above compositions may include various amounts of the compounds represented by formulae (Ia) and (Ib). In different embodiments, for example, the composition may comprise the above compounds, which may be the same or different, in the following ratios denoted by (a), (b), and (c):
(a) compounds represented by formula (Ia) being present in a range from about 1 percent (w/w) to about 99 percent (w/w) and compounds represented by formula (Ib) being present in a range from about 1 percent (w/w) to about 99 percent (w/w) such that the sum of the total percentage of such compounds represented by formulae (Ia) and (Ib) equals about 100 percent (w/w). A preferred composition comprises compounds represented by formula (Ia) that is 6-methoxy-2-[[(4-methoxy-3,5dimethyl-2-pyridinyl)methyl]sulfinyl]-1H-benzimidazole, which is essentially free of a compound represented by formula (Ib);

(b) compounds represented by formula (Ia) being present in a range from about 96 percent (w/w) to about 99–100 percent (w/w) and compounds represented by formula (Ib) being present in a range from about 0–1 percent (w/w) to about 4 percent (w/w) such that the sum of the total percentage of such compounds represented by formulae (Ia) and (Ib) equals about 100 percent (w/w). A preferred (Ia) compound for this composition also is 6-methoxy-2-[[(4-methoxy-3,5-dimethyl-2-pyridinyl)methyl]sulfinyl]-1H-benzimidazole and a preferred (Ib) compound is 5-methoxy-2-[[(4-methoxy-3,5-dimethyl-2-pyridinyl)methyl]sulfinyl]-1H-benzimidazole; and (c) compounds represented by formula (Ia) being present in a range from about 1 percent (w/w) to about 91 percent (w/w) and compounds represented by formula (Ib) being present in a range from about 9 percent (w/w) to about 99 percent (w/w) such that the sum of the total percentage of such compounds represented by formulae (Ia) and (Ib) equals about 100 percent (w/w). In one preferred composition, compounds represented by (Ib) are present in an amount greater than about 15 percent In another preferred composition, compounds represented by formula (Ib) are present in an amount equal to or greater than about 18 percent. In each such compositions, a preferred (Ia) compound is 6-methoxy-2-[[(4-methoxy-3,5-dimethyl-2-pyridinyl)methyl]sulfinyl]-1H-benzimidazole and a preferred (Ib) compound is 5-methoxy-2-[[(4methoxy-3,5methyl-2-pyridinyl)methyl]sulfinyl]-1H-benzimidazole.

Each of the above embodiments discussed in (a), (b), and (c) above may include various combinations of diastereomer. Such diastereomers are as follows: (a) $S_{xa}$—$R_{4q}$ (b) $S_{xa}$—$R_{4z}$ (c) $S_{xb}$—$R_{4q}$ or (d) $S_{xb}$—$R_{4z}$, or one or more pharmaceutically acceptable salts, solvates, hydrates, or combinations thereof of the compounds represented by formulae (Ia) and (Ib).

Any of the above composition embodiments may include, for example, compounds of the pairs (Iai)–(Ibi), (Iaii)–(Ibii), (Iaiii)–(Ibiii), and (Iaiv)–(Ibiv) as follows:

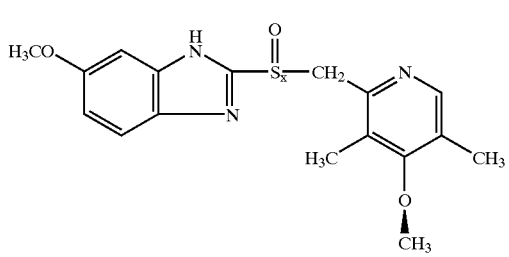
(Iai)

and

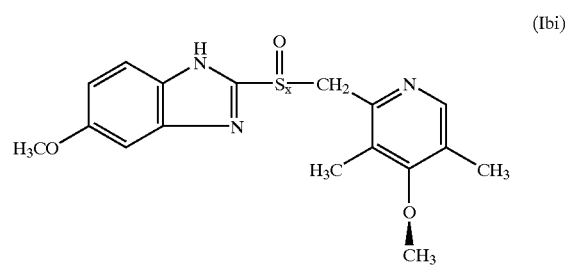
(Ibi)

wherein each $S_x$ is $S_{sx}$;

or one or more pharmaceutically acceptable salts, solvates, hydrates, or combinations thereof of the composition;

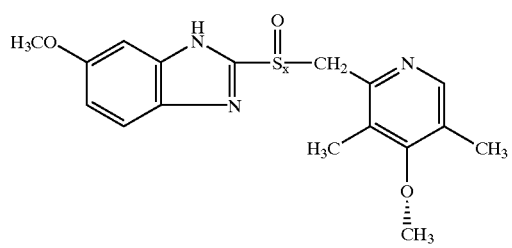
(Iaii)

and

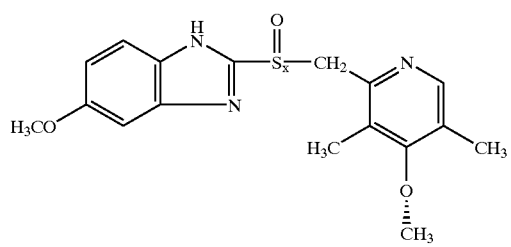
(Ibii)

wherein each $S_x$ is $S_{sa}$;

or one or more pharmaceutically acceptable salts, solvates, hydrates, or combinations thereof of the composition;

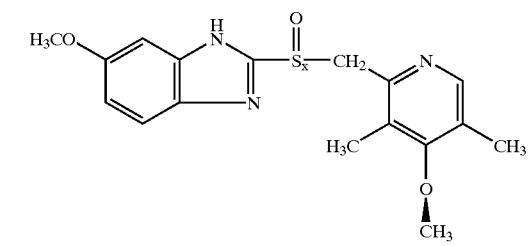
(Iaiii)

and

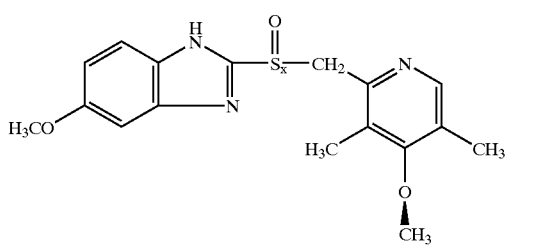

(Ibiii)

wherein each $S_x$ is $S_{xb}$;
or one or more pharmaceutically acceptable salts, solvates, hydrates, or combinations thereof of the composition; and

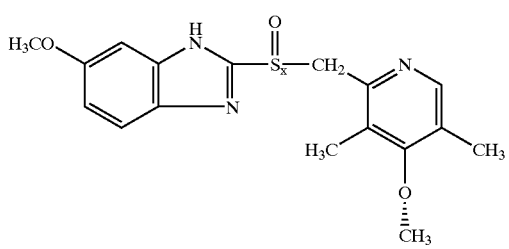

(Iaiv)

and

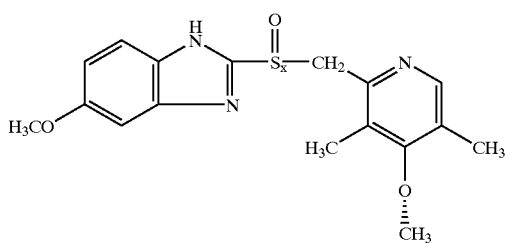

(Ibiv)

wherein each $S_x$ is $S_{xb}$;
or one or more pharmaceutically acceptable salts, solvates, hydrates, or combinations thereof of the composition.

Hereinafter, the compounds (Iai), (Iaii), (Iaiii), (Iaiv), (Ibid, (Ibii), (Ibiii), and (Ibiv) are defined by the structures presented above.

In another aspect, the invention provides compositions comprising two or more compounds each of compounds represented by formulae (Ia) and (Ib) as described above or one or more pharmaceutically acceptable salts, solvates, hydrates, or combinations thereof of the compounds represented by formulae (Ia) and (Ib). In compositions and complexes of the present invention, each of the compounds represented by formulae (Ia) and (Ib) may be the same or different.

The above compositions may include various amounts of the compounds represented by formulae (Ia) and (Ib). In different embodiments, for example, the composition may comprise the above compounds, that may be the same or different, in the following ratios denoted by (a), (b), and (c) as set forth above.

The above compositions comprising compounds represented by formulae (Ia) and (Ib) may advantageously include various percentages of these compounds. In one embodiment for example, the percentage of compounds represented by formula (Ib) in the composition is less than about 40 percent (w/w) and the percentage of compounds of formula (Ia) is such that the sum of the total percentage of such compounds represented by formulae (Ia) and (Ib) is equal to about 100 percent (w/w). In another embodiment, the percentage of compounds represented by formula (Ib) in said compositions is from about 9 percent (w/w) to about 50 percent (w/w) and the percentage of compounds of formula (Ia) is such that the sum of the total percentage of such compounds represented by formulae (Ia) and (Ib) is equal to about 100 percent (w/w). Preferably, said percentage of compounds represented by formula (Ib) is about 15 percent (w/w) to about 50 percent (w/w), and more preferably from about 18 percent (w/w) to about 50 percent (w/w).

Such composition of such two or more compounds may contain various amounts of the enantiomers $S_{xa}$, $S_{xb}$, $R_{4q}$, and $R_{4z}$. Methods for making the various enantiomers and diastereomers are set forth herein. In one embodiment, for example, each of the enantiomers represented by $S_{xa}$ and $S_{xb}$ in the compounds represented by formula (Ia) is present in a range from about 0 percent (w/w) to about 100 percent (w/w) such that the total percentage of the sum of $S_{xa}$ and $S_{xb}$ equals about 1 00 percent (w/w). In another embodiment, each of the enantiomers represented by $R_{4q}$ and $R_{4z}$ is present in a range from about 0 percent (w/w) to about 100 percent (w/w) such that when the total percentage of the sum of $R_{4q}$ and $R_{4z}$ equals about 100 percent (w/w)

In such compositions, each of the at least two compounds, may be the sate or different Any number of combinations of individual diastereomers or combinations thereof of the compound represented by formula (Ia) may be present in the composition. Examples of such diastereomers are as follows: $S_{xa}$—$R_{4q}$; $S_{xa}$—$R_{4z}$; $S_{xb}$—$R_{4q}$; and $S_{xb}$—$R_{4z}$, or one or more pharmaceutically acceptable salts, solvates, hydrates, or combinations thereof of the compound represented in formulae (Ia) and (Ib).

In various embodiments, the above diastereomers or combinations thereof may be present in such a manner wherein the composition forms a racemic mixture. In other embodiments, such diastereomers may be present in such a manner wherein the composition does not form a racemic mixture.

In another embodiment, the diastereomers of the compounds represented by formulae (Ia) and (Ib) that are present in the above compositions may include, for example, the following: (a) $S_{xa}$—$R_{4q}$ and (b) $S_{xb}$—$R_{4z}$ or one or more pharmaceutically acceptable salts, solvates, hydrates, or combinations thereof. In one example of this embodiment, the composition forms a racemic mixture. In another example of this embodiment, the composition does not form a racemic mixture. In another example of this embodiment, the composition is essentially free from compounds having diastereomers represented by $S_{xa}$—$R_{4z}$ and $S_{xb}$—$R_{4q}$.

In another embodiment, the diastereomers of each of the compounds represented by formulae (Ia) and (Ib) in the composition are $S_{xa}$—$R_{4q}$ and $S_{xa}$—$R_{4z}$ or one or more pharmaceutically acceptable salts, solvates, hydrates, or combinations thereof. In one example of this embodiment, the above composition is essentially free of compounds represented by formulae (Ia) and (Ib) having diastereomers represented by $S_{xa}$—$R_{4q}$ and/or $S_{xb}$—$R_{4z}$. Typically, this composition is in the form of an oil which, using the technique taught hereinafter, may form a crystalline, preferably a microcrystalline, composition. Otherwise, a salt of such composition may also be formed independently or, preferably, in situ, as described hereinafter.

In another embodiment, the diastereomers of the compounds represented by formulae (Ia) and (Ib) which are present in the above compositions may include the following: (a) $S_{xb}$—$R_{4q}$ and (b) $S_{xa}$—$R_{4z}$, or one or more pharmaceutically acceptable salts, solvates, hydrates, or combinations thereof. In one example of this embodiment, the enantiomer represented by $S_{xa}$ in each compound in each composition is present in optically pure form as defined herein. In another example of this embodiment, the composition is essentially free from compounds having diastereomers represented by $S_{xa}$—$R_{4q}$ and $S_{xb}$—$R_{4z}$ The above compositions comprising the various diastereomer components may be present in various amounts. In another example of the above embodiments, the percentage of enantiomers represented by $R_{4z}$ for either or both of the compounds represented by formulae (Ia) and (Ib) comprises greater than about 5 percent (w/w) and lees than about 49 percent (w/w) in the compounds represented by formulae (Ia) and (Ib) such that the sum of the total percentage of such enantiomers represented by $R_{4q}$ and $R_{4z}$ equals about 100 percent (w/w). In another example of the above embodiments, the percentage of enantiomers represented by $R_{4z}$ for either or both of the compounds represented by formulae (Ia) and (Ib) comprises greater than about 51 percent (w/w) in the compounds represented by formulae (Ia) and (Ib) such that the sum of the total percentage of such enantiomers represented by $R_{4q}$ and $R_{4z}$ equals about 100 percent (w/w).

In another embodiment, the diastereomers of the compounds represented by formulae (Ia) and (Ib) that are present in the above compositions may include the following: (a) $S_{xb}$—$R_{4q}$ and (b) $S_{xb}$—$R_{4z}$, or one or more pharmaceutically acceptable salts, solvates, hydrates, or combinations thereof. In one example of this embodiment, the enantiomer represented by $S_{xb}$ in each compound in each composition is present in optically pure form as defined herein. In another example of this embodiment, the composition is essentially free from compounds having diastereomers represented by $S_{xa}$—$R_{4q}$ and $S_{xa}$—$R_{4z}$ The above compositions comprising the various diastereomer components may be present in various amounts. In another example of the above embodiments, the percentage of enantiomers represented by $R_{4z}$ for either or both of the compounds represented by formulae (Ia) and (Ib) comprises greater than about 5 percent (w/w) and less than about 49 percent (w/w) in the compounds represented by formulae (Ia) and (Ib) such that the sum of the total percentage of such enantiomers represented by $R_{4q}$ and $R_{4z}$ equals about 100 percent (w/w). In another example of the above embodiments, the percentage of enantiomers represented by $R_{4z}$ for either or both of the compounds represented by formulae (Ia) and (Ib) comprises greater than about 1 percent (w/w) in the compounds represented by formulae (Ia) and (Ib) such that the sum of the total percentage of such enantiomers represented by $R_{4q}$ and $R_{4z}$ equals about 100 percent (w/w).

In another embodiment of the above composition, the diastereomers of each of such compounds represented by formulae (Ia) and (Ib) each is $S_{xa}$—$R_{4q}$, or one or more pharmaceutically acceptable salts, solvates, hydrates, or combinations thereof. In various embodiments of the compositions of the invention, the compounds represented by formulae (Ia) and (Ib) may be present in optically pure form, with the term optically pure being preferably defined hereinabove. In another example of this embodiment, the composition comprising compounds represented by formulae (Ia) and (Ib) are essentially free of such compounds comprising each of the diastereomers represented by: (a) $S_{xa}$—$R_{4z}$; (b) $S_{xb}$—$R_{4q}$; and (c) $S_{xb}$—$R_{4z}$.

In another embodiment of the above composition, the diastereomers of each of such compounds represented by formulae (Ia) and (Ib) each is $S_{xa}$—$R_{4z}$, or one or more pharmaceutically acceptable salts, solvates, hydrates, or combinations thereof. In various embodiments of the compositions of the invention, the compounds represented by formulae (Ia) and (Ib) may be present in optically pure form, with the term optically pure being preferably defined herein. In another example of this embodiment, the composition comprising compounds represented by formulae (Ia) and (Ib) are essentially free of such compounds comprising each of the diastereomers represented by: (a) $S_{xa}$—$R_{4q}$ (b) $S_{xb}$—$R_{4q}$ and (c) $S_{xb}$—$R_{4z}$.

In another embodiment of the above composition, the diastereomers of each of such compounds represented by formulae (Ia) and (Ib) each is $S_{xb}$—$R_{4q}$, or one or more pharmaceutically acceptable salts, solvates, hydrates, or combinations thereof. In various embodiments of the compositions of the invention, the compounds represented by formulae (Ia) and (Ib) may be present in optically pure form, with the term optically pure being preferably defined herein. In another example of this embodiment, the composition comprising compounds represented by formulae (Ia) and (Ib) are essentially free of such compounds comprising each of the diastereomers represented by: (a) $S_{xa}$—$R_{4q}$ (b) $S_{xa}$—$R_{4z}$ and (c) $S_{xb}$—$R_{4z}$.

In another embodiment of the above composition, the diastereomers of each of such compounds represented by formulae (Ia) and (Ib) each is $S_{xb}$—$R_{4z}$, or one or more pharmaceutically acceptable salts, solvates, hydrates, or combinations thereof. In various embodiments of the compositions of the invention, the compounds represented by formulae (Ia) and (Ib) may be present in optically pure form, with the term optically pure being preferably defined herein. In another example of this embodiment, the composition comprising compounds represented by formulae (Ia) and (Ib) are essentially free of such compounds comprising each of the diastereomers represented by: (a) $S_{xa}$—$R_{4q}$ (b) $S_{xa}$—$R_{4z}$ and (c) $S_{xb}$—$R_{4q}$.

Any of the composition embodiments may include, for example, compounds of the pairs (Iai)–(Ibi), (Iaii)–(Ibii), (Iaiii)–(Ibiii), and (Iaiv)–(Ibiv) or one or more pharmaceutically acceptable salts, solvates, hydrates, or combinations thereof as previously set forth herein.

Any of such composition embodiments comprising any of the compounds represented by formulae (Ia) and (Ib), individual species of compounds (Iai)–(Ibi), (Iaii)–(Ibii), (Iaiii)–(Ibiii), and (Iaiv)–(Ibiv), diastereromers thereof, or one or more pharmaceutically acceptable salts, solvates, hydrates, or combinations thereof, may be present in crystalline form, amorphous form, or combinations thereof.

The invention also provides compositions of active pharmaceutical ingredient ("API") comprising any of the above composition embodiments. Advantageously, any of the compositions comprising compounds represented by formulae (Ia) and (Ib) may also comprise any of the specific compositions represented by formulae (Iai)–(Ibi); (Iaii)–(Ibii); (Iaiii)–(Ibiii); and (Iaiv)–(Ibiv) or one or more pharmaceutically acceptable salts, solvates, hydrates, polymorphs, or combinations thereof, whether in crystalline form, amorphous form, or a combination thereof, can be used in any such API compositions.

The compounds represented by formulae (Ia) and (Ib) may be prepared as described in various embodiments. More specifically, the methods describe forming the compounds in solution, The presence of either the compounds of formula (Ia) and/or formulae (Ia) and (Ib) in solution causes formation of the corresponding tautomer. Thus, these methods essentially describe forming each series of compounds. However, the present invention provides novel compounds of the formulae (Ia) and (Ib) in their respective solid states.

Compounds of the present invention are prepared by using a variety of synthetic processes. For example, in the crystallization of 6-methoxy-2-[[(4-methoxy-3,5-dimethyl-2-pyridinyl)methyl]sulfinyl]-1H-benzimidazole (one compound represented by formula (Ia)) and 5-methoxy-2-[[(4methoxy-3,5-dimethyl-2-pyridinyl)methyl]sulfinyl]-1H-benzimidazole (one compound represented by formula (Ib)) from solution, the amount of compound represented by formula (Ia) significantly varies by inter alia the rate of crystallization. Accordingly, slight variations within the same process as taught in the prior art, such process not being appropriately controlled or defined as to regulate the amount of previously unknown compound represented by formula (Ia), will result in various ratios of compounds represented by formula (Ia) to compounds represented by formula (Ib).

Additionally when using such processes represented in the prior art, negligible or trace amounts of previously unknown compounds are formed as described herein. For example, in the preparation of such composition as referenced in the immediately preceding paragraph; compounds having the previously unknown diastereomers $S_{xa}$—$R_{4q}$ and $S_{xb}$—$R_{4z}$ are formed with varying and inconsistent ratios of compounds represented by formulae (Ia) and (Ib). Also formed in trace quantities, and typically in amorphous form, are compounds represented by formulae (Ia) and (Ib) having the previously unknown diastereomers $S_{xa}$—$R_{4z}$ and $S_{xb}$—$R_{4q}$.

Furthermore, when prior art processes are used with the intent of forming "salts" of such composition, the rather broad teachings may result in salts, but may also result in the formation of novel complexes that are described herein.

Accordingly, the processes taught in the prior art for the preparation of "omeprazole" as well as "esomeprazole" (the intended S-isomer of "omeprazole") provide quantities of previously unknown and unrecognized compounds having pharmaceutical activity, or that are used as intermediates in the preparation of pharmaceutically active compounds of the present invention, or that are used as prodrugs that convert to the active metabolite in vivo. Furthermore, many such processes do not invariably provide the same result when conducted as taught in the prior art Embodiments describing methods for preparing the compounds of the present invention follow. In various embodiments, neither $R_3$ nor $R_5$ are hydrogen when $R_4$ is alkoxy.

In one embodiment, the compounds may be formed by oxidizing a compound of formula (II):

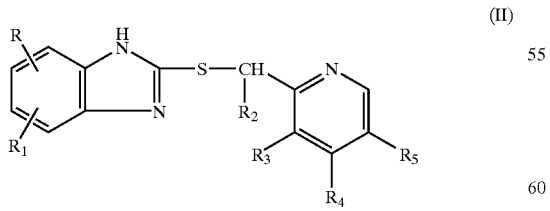

(II)

wherein R is alkoxy at the 5- or 6-position, $R_1$, $R_2$, $R_3$, $R_4$, and $R_5$ have the meanings defined above, to form the compound of formulae (Ia) or (Ib). The oxidation of the sulfur atom to sulfinyl (S→O) typically takes place in the presence of an oxidizing agent selected from the group consisting of nitric acid, hydrogen peroxide, peracids, peresters, ozone, dinitrogentetraoxide, iodosobenzene, N-halosuccinimide, 1-chlorobenzotriazole, t-butythypochlorite, diazobicyclo-[2,2,2,]-octane bromine complex, sodium metaperiodate, selenium dioxide, manganese dioxide, chromic acid, cericammonium nitrate, bromine, chlorine, and sulfuryl chloride. The oxidation usually takes place in a solvent wherein the oxidizing agent is present in some excess in relation to the product to be oxidized.

In another embodiment, a compound of formula (III):

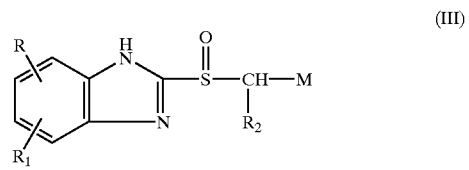

(III)

wherein R $R_1$, and $R_2$ are defined herein, and M is a metal selected from potassium, sodium, and lithium; may be reacted with a compound of formula (IV):

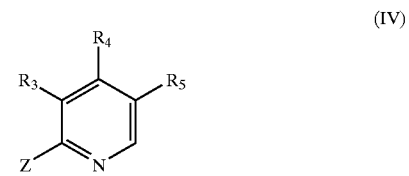

(IV)

wherein $R_3$, $R_4$, and $R_5$ have the same meanings as given above, and Z is a reactive esterified hydroxy group to form compounds of formulae (Ia) and (Ib).

In another embodiment, a compound of formula (V):

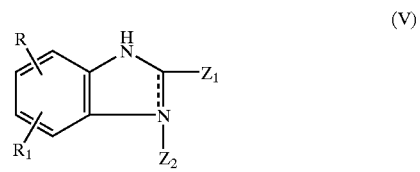

(V)

wherein R and $R_1$ are defined herein and $Z_1$ is (=S) or a reactive esterified hydroxy group, wherein when $Z_1$ is (=S), $Z_2$ is H, is reacted with a compound of formula (VI):

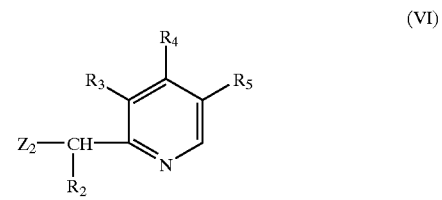

(VI)

wherein $R_2$, $R_3$, $R_4$, and $R_5$ have the same meanings as given above, and $Z_2$ is a reactive esterified hydroxy group or SH, to form an intermediate of formula (II) above, which then is oxidized to give compounds of formulae (Ia) and (Ib).

In another embodiment, a compound of formula (VII):

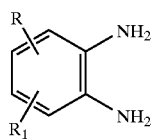

(VII)

wherein R and $R_1$ are defined above is reacted with a compound of formula (VIII):

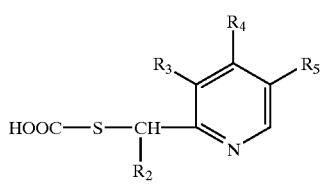

(VIII)

wherein $R_1$, $R_3$, $R_4$, and $R_5$ are defined above, to form an intermediate of formula (II) above, which then is oxidized to give compounds of formulae (Ia) and (Ib).

In the reactions above, Z, $Z_1$, and $Z_2$ may be a reactive esterified hydroxy group which is a hydroxy group esterified with strong, inorganic or organic acid, preferably a hydrohalogen acid, such as hydrochloric acid, hydrobromic acid, or hydroiodic acid, as well as sulfuric acid or a strong organic sulfonic acid, such as, for example, a strong aromatic acid, e.g., benzenesulfonic acid, 4-bromobenzenesulfonic acid or 4-toluenesulfonic acid. The starting materials are known or may, if they should be new, be obtained according to processes known per se.

In another embodiment, compounds of formulae (Ia) and (Ib) may be formed by reacting a compound of formula (II):

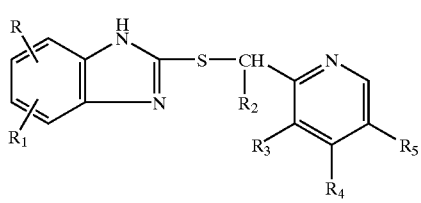

(II)

wherein R, $R_1$, $R_2$, $R_3$, $R_4$, and $R_5$ have the meanings defined above, with m-chloroperoxybenzoic acid in a methylene chloride solution. The reaction should be carried out at a substantially constant pH. The reaction product is then extracted with a base (e.g., NaOH) and the aqueous phase is separated from the organic phase. An alkyl format is added to the aqueous phase resulting in the crystallization of the compounds of formulae (Ia) and (Ib).

The invention also provides methods for producing compositions of compounds represented by formulae (Ia) and (Ib). As discussed herein, Applicants have unexpectedly discovered that it is possible to obtain the compounds of formulae (Ia) and (Ib) in combination and, preferably co-crystallized, in part or in whole, compositions in various amounts relative to one another according to techniques taught below.

Applicants have confirmed that solution NMR reveals the tautomerization of the compounds of formulae (Ia) and (Ib). Solution NMR suggests that the tautomerization reaches an equilibrium at approximately a 2:1 ratio of compounds represented by formula (Ia) to compounds represented by formula (Ib). Upon crystallization and isolation, the compounds of formula (Ia) appear to be the more energetically favorable isomer and crystallizes first This equilibration/crystallization process allows for the predominant isolation of the solid (e.g., crystalline) isomer of compounds of formula (Ia). Through solution NMR experiments, it is believed that the exchange rate of the amine proton during tautomerization may be pH dependent. For example, with the addition of a small amount of base, the proton exchange rate in the NMR was shown to slow, and two distinct proton NMR peaks were observed for each of the benzimidazole aromatic protons.

Methods for forming compositions comprising compounds of formulae (Ia) and (Ib) are described herein with reference to certain embodiments. However, variations from these embodiments may be carried out without departing from these separation methods described by the present invention.

Applicants have determined that compositions of compounds of formulae (Ia) and/or (Ib) may be formed in relative ratios of the compounds to one another not suggested by the prior art. In one embodiment, the method may provide such compound represented by formula (Ia) substantially free from its corresponding isomer (compounds of formula (Ib)). Preferably, compounds represented by formula (Ia) are present in an amount ranging from about 96 to about 99 percent (w/w). The method generally includes first providing a solution comprising the tautomers of formulae (Ia) and (Ib) and a solvent Examples of solvents include, but are not limited to, aqueous solvents, preferably basified solvents such as, for example, water and ammonia, or organic solvents. Examples of organic solvents include, but are not limited to, ketones (e.g., acetone), nitrile solvents (e.g., acetonitrile, acatonitrile/water), amine solvents (e.g., dimethyl formamide (DMF) or pyridine), aryl solvents (e.g., toluene), halogenated solvents (e.g., methylene chloride, chloroform), alcohols (e.g., methanol, ethanol), ammonium hydroxide, and sulfur-containing solvents (e.g., dimethyl sulfoxide (DMSO)). Mixtures of the above may also be employed.

Preferably, the solution is saturated. The solution is evaporated slowly (preferably from about 3 days to about 7 days) until crystal formation is achieved, with the compounds represented by formulae (Ia) and/or (Ib) typically co-crystallizing in the same lattice.

Advantageously, the relative amounts of compounds of formulae (Ia) and (Ib) that may be obtained in corystalline form can be manipulated by judicious selection of a number of variables relating to, but not necessarily limited to, solvent choice, humidity, temperature, and vapor diffusion control rate. The selection of solvent for use in the method may be governed by various considerations. For example, although not intending to be bound by theory, it is believed that the use of slower evaporation solvents (e.g., DMF) and the solvent's or solvents' controlled evaporation at lower temperatures produces crystals with a higher percentage of compounds represented by formula (Ia) in the crystalline lattice, preferably compounds of formula (Ia) being pure or essentially free of compounds represented by formula (Ib) as defined herein. In other embodiments, organic solvents such as, for example, methylene chloride, ethanol, and chloroform are capable of yielding crystals with higher percentages of compounds represented by formula (Ib) in such crystalline lattice, typically up to about 20 percent (w/w) to about 50 percent (w/w) of compounds represented by formula (Ib).

With all other factors Losing consistent, it is believed that the percentage of moisture present in the crystallization chamber is directly proportional to the percentage of compounds represented by formula (Ib). Higher levels of humidity in the chamber inc. ease the percentage of compounds represented by formula (Ib) which crystallizes in the crystalline lattice.

With all other factors being consistent, temperature does not appear to significantly influence which of the compounds of the present invention, (e.g., compounds represented by formulae (Ia) and (Ib)) will be formed, but may influence the size and clarity of such crystals. Typically, temperatures below ambient temperature provides crystals having larger size and better clarity.

The crystallization (e.g., recrystallization) rate may also be influenced by the rate of solvent evaporation, and is influenced by using methods well known in the art. In one embodiment, by exposing a sample of compounds represented by formulae (Ia) and (Ib) to the surrounding environment, the rate of evaporation should increase and the formation of such compounds represented by formula (Ib) in the crystal lattice should increase. Conversely, in another embodiment, by controlling (i.e., slowing) the rate of evaporation, the recrystallization process should be slowed, thus yielding increased amounts of such compounds represented by formula (Ia).

Accordingly, one may manipulate various processing variables as set forth herein to yield the percentage of compound(s) represented by formulae (Ia) and/or (Ib) as desired. For example, in one preferred embodiment, using DMF, reduced evaporation, reduced humidity and lowered temperatures, higher percentages of the compound represented by formula (Ia) are obtained, preferably from about 96 to about 100 percent (w/w). Crystals containing the higher percentages of the compound represented by formula (Ib) may be produced using a solvent comprising chloroform or methylene chloride, increased evaporation, and ambient temperature.

The structure of one compound of formula (Ia), and in particular, 6-methoxy-2-[[(4-methoxy-3,5-dimethyl-2-pyridinyl)methyl]sulfinyl]-1H-benzimidazole, has been confirmed by x-ray single crystal analyses on isolated crystals formed in accordance with the above methods.

By employing the above method(s) or obtaining the compound represented by formula (Ia) in solid state, one obtains the (−) and (+) enantiomers as a racemic mixture, with these enantiomers including various amounts of diastereomers as set forth herein. In one embodiment, Applicants have discovered that the (−) and (+enantiomer may be predominantly present as the $S_{xa}$—$R_{4q}$ and $S_{xb}$—$R_{4z}$ diasteromers respectively. Although not intending to be bound by theory, in this embodiment, the two molecules (i.e., compounds of formulae (Ia) and (Ib)) co-crystallize in a centric space group in which the molecules are related to each other through a center of inversion and linked by hydrogen bonding from the amine hydrogens to the sulfoxide oxygens. The $R_4$ methoxy methyl is directed towards the center of the bridged complex. Examination of the contact distances in the region where the other methoxymethyl would presumably reside demonstrates that there is not adequate space within the lattice for the other diastereomers ($S_{xa}$—$R_{4z}$ and $S_{xb}$—$R_{4q}$) to co-exist. In this embodiment, the compound represented by formula (Ia) may comprise about 99 percent (w/w) of the $S_{xb}$—$R_{4z}$ and $S_{xa}$—$R_{4q}$ diastereomers and the remaining percentage of other components which may include, for example, the diastereomers $S_{xa}$—$R_{4z}$ and $S_{xb}$—$R_{4q}$, generally inamorphous form.

In the above embodiment, the crystallization of the compounds represented by formulae (Ia) and (Ib) is believed to be controlled thermodynamically by a bipyrimidal inversion equilibrium at the sulfoxide chiral center which forces the $S_{xb}$—$R_{4q}$ diastereomer to $S_{xa}$—$R_{4q}$ and the $S_{xa}$—$R_{4z}$ diastereomer to $S_{xb}$—$R_{4z}$ diastereomers. Such behavior may be confirmed by examining the x-ray crystal structure, and more specifically, the crystal packing. Not intending to be bound by theory, it is believed that the molecular packing does not provide adequate area for the other diastereomers to be present within the current crystal lattice.

Upon obtaining a composition comprising a compound of formula (Ia) as described above, one may apply a suitable technique to resolve the individual (−) and (+) enantiomers. One may then apply a suitable technique (including, for example, those described subsequently) to resolve the diastereomer components in the (−) and (+) enantiomers. With respect to the (−) enantiomer of such compound represented by formula (Ia), in a number of embodiments, the above techniques are capable of yielding about 95 percent (w/w) of the $S_{xa}$—$R_{4q}$ diastereomer and about 5 percent (w/w) of the $S_{xa}$—$R_{4z}$ diastereomer of the compound of formula (Ia), particularly in the specific embodiment in which compound (Ia) is described by compounds of the formulae (Iai) and (Iaii). Although not intending to be bound by theory, it is believed that the bipyrimidal inversion equilibrium at the sulfoxide chiral center forces the $S_{xb}$—$R_{4q}$ diastereomer to the $S_{xa}$—$R_{4q}$ diastereomer of such compound represented by formula (Ia). Moreover, the composition of the resolved (+) enantiomer by the resolution techniques set forth herein allow for the formation of predominantly the $S_{xb}$—$R_{4z}$ diastereomer (e.g., about 95 percent (w/w)). Similar to the formation of the $S_{xa}$—$R_{4q}$ diastereomer, a bipyrimidal inversion equilibrium is believed to occur forcing the $S_{xa}$—$R_{4z}$ diastereomer to the $S_{xb}$—$R_{4z}$ diastereomer. Attentively, in another embodiment, a biosynthesis resolution method allows for the (−) enantiomer to be resolved from the (+) enantiomer wherein the composition of the (−) enantiomer includes about 50 percent (w/w) of the $S_{xa}$—$R_{4q}$ diastereomer and about 50 percent (w/w) of the $S_{xa}$—$R_{4z}$ diastereomer. Likewise, the (+) diastereomer resolved by this biosynthesis method includes about 50 percent (w/w) of the $S_{xb}$—$R_{4q}$ diastereomer and about 50 percent (w/w) of the $S_{xb}$—$R_{4z}$ diastereomer.

The above techniques can also be used to co-crystallized a metal ion analogue of the compounds represented by formulae (Ia) and (Ib) in the amounts set forth above. Redissolving such compound(s) is believed to initiate the bipyrimidal inversion which generates the distereomer components $S_{xa}$—$R_{4q}$, $S_{xa}$—$R_{4z}$, $S_{xb}$—$R_{4q}$, and $S_{xb}$—$R_{4z}$ in amounts which are believed to depend upon, but not potentially limited to, the bipyridimal inversion equilibrium rate, the time it takes to create the metal analog, and the time it takes to crystallize the analog. It should be appreciated that these variables may be manipulated by one skilled in the art Preferably, the range of each of the four diastereomers can range from about a 60:40 ratio to about a 100:0 ratio of enantiomeric $S_{ax}$—$R_{4z}$ and $S_{xb}$—$R_{4z}$ analogs to $S_{xa}$—$R_{4a}$ and $S_{xb}$—$R_{4z}$ analogs.

The present invention also provides a method of forming compounds of formula (Ib) in the solid state. In a preferred specific embodiment, the method encompasses increasing the level of the selected compound represented by formula (Ib) in a composition comprising the selected compounds represented by formulae (Ia) and (Ib). The method comprises subjecting such compound of formula (Ia) and/or formulae (Ia) and (Ib) to grinding conditions sufficient to permit a solid state phase transformation of such compound(s) to a compound of formula (Ib), or, at least, a composition having an increased percentage of such compound represented by formula (Ib) compared to the starting material. Preferably, the compound represented by the formula (Ia) is present in a composition and the above method increases the percentage of the compound represented by formula (Ib) present in the composition. In this embodiment, prior to the subjecting step, the composition may contain the compound represented by formula (Ia) essentially free from the compound represented by formula (Ib), although it should be appreciated that other examples are contemplated in which the composition comprises the compounds of formulae (Ia) and (Ib) in amounts set forth herein.

Various conditions may be manipulated during the subjecting step to govern the amount of compound represented by formula (Ib), e.g., revolutions per minute (RPM) and length of subjecting step. The subjecting step is preferably carried out from about 350 rpm to about 500 rpm, more preferably from about 350 rpm to about 450 rpm, and most preferably about 450 rpm. A preferred time for carrying out the subjecting step is from about 5 to about 30 minutes, more preferably from about 10 min to about 30 min, and most preferably about 15 minutes. Advantageously, the compounds are not degraded during this operation. The subjecting step may be carried out by various machines that apply appropriate grinding energies to solid materials. Preferably, the machine is a mechanical grinder. One example of a suitable grinder is set forth in U.S. Pat. No. 5,773,173 to Whittle et al., the disclosure of which is incorporated herein by reference in its entirety. It should be appreciated that one may employ embodiments other than those described above and still be within the scope of the method of forming such compounds of the formula (Ib) in solid state.

Although not intending to be bound by theory, such compounds of formula (Ia) are believed to be crystalline with little amorphous content. However, when grinding is applied to a solid sample comprising the compound of formula (Ia), and in a preferred embodiment the compounds of formulae (Ia) and (Ib), an increase in the amorphous character of the sample is believed to result along with an increase in the amount of compound of formula (Ib). Again, not intending to be bound by theory, it is believed that the sample undergoes a solid state transformation and "recrystallizes" or transforms over a relatively short period of time from the more amorphous state to a more crystalline state subsequent to grinding. Nonetheless, it is believed that by performing multiple grinding steps in sequence, (i.e. grinding followed by relaxation followed by grinding) one may obtain a solid sample that becomes more amorphous in character and hence comprises a greater amount of the compound of the formula (Ib) as opposed to a sample that has experienced a lesser amount of grinding.

The above method may provide various amounts of the compound of formula (Ib).

The structure of the compound of formula (Ib) can be confirmed by solid state techniques such as, for example, X-ray powder diffraction patterns, Raman, FTIR, solid state NMR, and thermal analysis, of the ground material and the unground material. For example, comparison of the two powder patterns showed distinct decreases in intensity, broadening of the peaks, and an increase in the amorphous nature for the ground material. The ground material showed a powder pattern that is more consistent with the proposed more amorphous nature of the compound of formula (Ib), e.g., 5-methoxy-2-[[(4-methoxy-3,5-dimethyl-2-pyridinyl)methyl]sulfinyl]-1H-benzimidazole.

The present invention also provides the compounds of formulae (Ia) and (Ib) in the form of pharmaceutically acceptable salts as described hereinbelow. Similar to the making of the compounds of formulae (Ia) and/or (Ib) described above, the making of a salt of each of the compounds of formulae (Ia) and/or (Ib) in solution results in the making of salts of both compounds due to tautomerization occurring in solution. Thus, these methods describe making salts of both families of compounds.

Depending upon the process conditions and the starting materials, the end product of the synthetic processes for preparing compounds represented by formulae (Ia) and/or (Ib) is typically obtained as a free base. Basic, neutral or mixed salts may be obtained as well as solvates and hemi-, mono-, sesqui-, tetra, or polyhydrates. Examples of suitable bases for salt formation include, but is not limited to, compounds containing alkali metals or alkali earth metals, although it is appreciated by the skilled artisan that bases containing other types of metals may be used. Examples of inorganic bases include, but are not limited to, sodium hydroxide, sodium carbonate, sodium bicarbonate, potassium hydroxide, calcium hydroxide, magnesium hydroxide, and the like. Organic bases in the form of, for example, nitrogen-containing components may be also used. Exemplary nitrogen-containing compounds include, but are not limited to, ammonium, organic amines, and the like. The free bases that are obtained may form salts with organic or inorganic acids.

As discussed in greater detail herein, metal hydrides, particularly sodium hydride, are preferably used in making the salts of the compounds of the present invention. Other methods that have been conventionally thought to be useful in making salts of such compounds have been found by Applicants to not invariably result in the formation of such salts, but instead have resulted in complex formation. Thus, the method of making such salts employing the metal hydrides of these compounds is not suggested by the prior art Acid addition salts may be difficult to form because of the acid labile nature of the compounds of the invention, but could be formed at a pH above 6.0 since the stability of the compounds increases. Acids suitable for making such salts may include, but are not limited to, hydrohalogen acids, sulfonic, phosphoric, nitric, and perchloric acids; aliphatic, alicyclic, aromatic, heterocyclic carboxy or sulfonic acids, such as formic, acetic, propionic, succinic, glycolic, lactic, malic, tartaric, citric, ascorbic, maleic, hydroxymaleic, pyruvic, phenytacetic, benzoic, p-aminobenzoic, antranilic, p-hydroxybenzoic, salicylic or p-aminosalicylic acid, embonic, methanesulfonic, ethanesulfonic, hydroxyethanesulfonic, ethylenesulfonic, haiogenbenzenesulfonic, toluenesulfonic, naphtylsulfonic or sulfanilic acids; methionine, tryptophane, lysine or arginine.

These or other salts of the new compounds, as e.g., picrates, may serve as purifying agents of the free bases obtained. Salts of the bases may be formed, separated from solution, and then the free base may be recovered from a new salt solution in a purer state. Because of the relationship between the new compounds in free base form and their salts, it will be understood that the corresponding salts are included within the scope of the invention.

The salts may be prepared by various techniques. For example, such salts can be prepared from organic compounds when that compound has an "acidic" proton. The proton may be removed, for example, by a type of base that allows for the formation of an anionic species of the compound countered by the cation. In embodiments encompassing polar, protic environments, such as an alkali or alkaline metal hydroxide or alkaline metal alkoxide present in an alcohol or mixed organic solvent such as a 2-butanone/toluene mixture, it is believed that the conversion to the salt may be governed by pKa differences. In various embodiments, such techniques are capable of yielding salts of the compounds of the present invention having the diastereomers represented by $S_{xa}$—$R_{4z}$ and $S_{xb}$—$R_{4q}$ in a range from about 60 to about 70 percent (w/w).

Another example of a method for preparing salts of compounds represented by formulae (Ia) and/or (Ib) comprises subjecting such compounds to a polar, aprotic environment to form such salts. Examples of polar, aprotic environments include, for example, an alkali or alkaline metal hydride in an organic solvent (e.g., tetrahydrofuran THF) or dimethylformamide (DMF)). Although not intending to be bound by theory, in polar, aprotic environments, the salt conversion may be governed by factors such as solubility of both the organic compound and the base used and the steric hindrance interactions. Although both types of reactions (e.g., polar, protic environments and polar, aprotic environments) can be used in forming the salts, reactions taking place in polar, aprotic environments are preferred. For example, using a polar, aprotic environment may preferably provide from about 90 to about 95 percent (w/w) yield of salts of the compounds, and/or compositions of the present invention. Although various alkali and alkaline metal salts can be made using the above methods, it is preferred to form sodium or magnesium salts of compounds of the present invention.

Typically, a solution of filtered alkali or alkaline metal hydride having a preferred concentration of about 50% to about 70% in mineral oil, preferably sodium or magnesium hydride, is added, preferably in situ, to a solution of one or more selected compounds and/or compositions of the present invention in an appropriate solvent and stirred for about 5 to about 30 minutes. The resulting solution is filtered, if necessary, and the resulting solids are dried in vacuo, typically at ambient temperature. The resulting powder can be re-crystallized as set forth herein or as known by one of ordinary skill in the chemical arts.

Alternatively, the desired, previously isolated compounds and/or compositions of the present invention are added to a solution of filtered alkali or alkaline metal hydride having a preferred concentration of about 50% to about 70% in mineral oil, preferably sodium or magnesium hydride, stirred, typically for about 5 to about 15 minutes, and allowed to sit at ambient temperature. Crystalline salts of the present invention result Each of the processes using hydrides for preparation of salts of compounds and compositions of the present invention can result in significantly increased/improved yields compared to the processes typically used and/or known to the ordinary skilled artisan.

In addition, other salts may be formed by various reactions. For example, in one embodiment, a complex may be formed by reacting the compounds represented by formulae (Ia) and/or (Ib) with a cation $A^{z+}$ by a suitable technique, e.g., ion-pair extraction. In the above embodiment, A is lithium, sodium, potassium, magnesium; calcium, titanium (4+), $N^+(R^1)_4$, or:

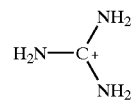

wherein $R^1$ is an alkyl group containing 1 to 4 carbon atoms, and z is 1, 2, or 4.

For example, tetrabutylammonium salts of the invention may be prepared by dissolving the $A^{z+}$ salt in water containing one or more tetrabutylammonium compounds such as, for example, the chloride or hydroxide followed by extraction of the tetrabutylammonium salt into a methylene chloride phase, and subsequent isolation of the tetrabutylammonium salt. In this manner, other tetraallkylammonium salts may be prepared.

In one embodiment, the salt of the compound of formula (I') may be formed by reacting the compound of formulae (Ia) and/or (Ib) with a base capable of releasing the cation $A^{z+}$ wherein z is 1, 2, or 4; and A is lithium, sodium, potassium, magnesium, calcium, titanium(4+), $N^+(R^1)_4$, or:

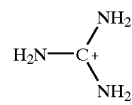

wherein $R^1$ is an alkyl group containing 1 to 4 carbon atoms, to provide a salt of the formula (I'):

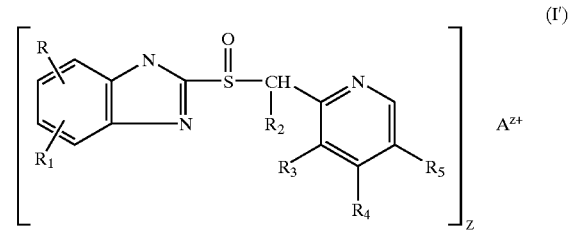

(I')

wherein R is alkoxy in the 5- or 6-position: $R_1$ is selected from the group consisting of hydrogen, alkyl, halogen, carboalkoxy, alkoxy, and alkanoyl; $R_2$ is hydrogen or alkyl; and $R_3$, $R_4$, and $R_5$ may be the same or different and are each selected from the group consisting of hydrogen, alkyl, alkoxy, and alkoxyalkoxy, and wherein z and $A^{z+}$ are defined above.

In one example, lithium, potassium, or sodium salts of the formula (I') may be prepared by treating the compounds of the formulae (Ia) and/or (Ib) with LiOH, NaOH, or KOH in an aqueous or nonaqueous medium, or with $LiOR^1$, $LiNH_2$, $LiNR^1_2$, $NaOR^1$, $NaNH_2$, $NaNR^1_2$, $KOR^{n1}$, $KNH_2$, $KNR^1_2$ wherein $R^1$ is defined above, in an aqueous or a nonaqueous medium. Magnesium, calcium, or titanium salts may be prepared by treating a compound of the formulae (Ia) or (Ib) with $Mg(OR^1)_2$, $Ca(OR^1)_2$, $CaH_2$, $Ti(OR^1)_4$ or $TiH_4$, wherein $R^1$ is defined herein, in a nonaqueous solvent such as an alcohol (for the alcoholates), or in an ether such as tetrahydrofuran.

In another example, a salt of the compound of formula (I') wherein A is:

may be prepared by treating compounds of the present invention with a strong base of the formula:

dissolved in a solvent such as, for example, an alcohol.

A salt represented by formula (I') may be converted to another salt of the same formula by exchanging the cation. When both the starting material and the salt obtained as final product are sufficiently soluble, such an exchange may be performed by using a cation-exchange resin saturated with the cation desired in the product. The exchange may also be performed by utilizing the low solubility of a desired salt.

The reaction between the compound of formulae (Ia) and/or (Ib) and $A^{z+}$ may also be carried out by ion-pair extraction. For example, tetrabutylammonium salts of the invention may be prepared by dissolving the $Na^+$ salt in water containing one or more tetrabutylammonium compounds followed by extraction of the tetrabutylammonium salt into a methylene chloride phase, and subsequent isolation of the tetrabutylammonium salt In this manner, other tetraalkylammonium salts may be prepared.

Illustrative examples of the radical $R^1$ are methyl, ethyl, n-propyl, n-butyl, isobutyl, sec-butyl, and tert-butyl.

A preferred method for forming magnesium salts of compounds of the present invention is characterized by the following consecutive steps: a) treating at least one compound of formulae (Ia) and/or (Ib) or salts thereof with magnesium alcoholate in a solution; b) separating inorganic salts from the reaction mixture; c) crystallizing the magnesium salts of such formulae (Ia) and/or (Ib); d) isolating the obtained crystalline magnesium salts and, optionally, e) purifying and drying the crystalline magnesium salts using conventional methods.

A process for manufacturing the magnesium salts is described as follows: a lower alcohol, such as methanol, ethanol, n-propanol or iso-propanol, preferably methanol, is treated in a solution of polar solvents with a weighed amount of magnesium at temperatures between about 0° C. and reflux temperature. The temperature should preferably be between about 10° C. and about 40° C. After addition of the magnesium to the solution the temperature can, in a second step, be raised further to between about 0° C. and reflux temperature, preferably about 20° C. to about 50° C. After termination of the reaction, the temperature is reduced to about 0° C. to about 40° C., preferably about 10° C. to about 25° C. The compound of formulae (Ia) and/or (Ib), or a salt thereof, is then added to the solution and alter termination of the reaction the mixture is cooled to about −10° C. to about +20° C., preferably about −5° C. to about +5° C. The solvent is then evaporated to about 40 to about 60 percent of the initial volume, which makes the inorganic salts precipitate. The precipitate is separated from the reaction solution, for example, by centrifugation or filtration, and the solution is heated from about 5° C. to about 30° C., whereafter the solution is seeded with magnesium crystals of the compound of formulae (Ia) and/or (Ib). An amount of water, which is approximately equal to the volume of the solution, is added to start the crystallization. The solution is cooled to about −10° C. to about +20° C., preferably about 0° C. to about 10° C., to complete the crystallization. The crystals are then separated from the mother liquor for example, by centrifugation or filtration, and washed with polar solvents, preferably an aqueous lower alcohol, such as aqueous methanol. Finally, the produced crystals are dried, preferably under reduced pressure and heating.

The magnesium salts may include various amounts of the compounds of the formulae (Ia) and/or (Ib). For example, in one embodiment, a magnesium salt composition may preferably comprise up to about 30 percent (w/w) of the compound of formula (Ib), and more preferably up to about 27 percent (w/w) of the compound of formula (Ib).

In another aspect, the invention also provides complexes of the compound represented by the formulae (Ia) and/or (Ib). In particular, the invention provides a composition comprising a complex of: (a) two or more compounds encompassed by compositions set forth herein comprising compounds represented by formulae (Ia) and/or (Ib); and at least one atom of a metal cation, preferably an alkali or alkaline metal cation. Exemplary metal cations are selected from the Groups IA, IIA, and IIIa of the periodic table although other cations may be employed. Preferably, the composition is present in crystalline form. Sodium and magnesium each are examples of preferred cations.

Such compositions of the present invention may employ solvent(s) that are typically employed in forming complexes. In a preferred embodiment, such compositions further include two solvents. The solvents are those which are capable of donating a pair of electrons, including, for example, alcohols, THF, DMF, DMSO, and mixtures thereof. The complexes of the invention may be formed by using materials which are known to be used in forming complexes, e.g., alkoxides and hydroxides of metal cations such as, without limitation, those described above. The two or more compounds represented by formulae (Ia) and/or (Ib) may be the same or different and may be present as compounds with any one of the four diastereomer configurations (e.g., $S_{xa}$—$R_{4q}$, $S_{xa}$—$R_4$, $S_{xb}$—$R_{4q}$, and $S_{xb}$—$R_{4z}$).

In general, complexes of compounds of formulae (Ia) and/or (Ib) typically include two compounds having at least one metal cation positioned therein. The metal cation bonds with various appropriate lone pair or electron donating sites on the two compounds, namely oxygen and nitrogen atoms with respect to such compounds. In various preferred embodiments, such complexes also typically include at least one "solvent residue" which is obtained from one or more solvents set forth herein. In such complexes, the solvent residue is bound to the metal cation and the nitrogen present on the benzimidazole portion of the compounds. Examples of suitable solvent residues include, without limitation, alkoxides (e.g., lower ($C_1$ to $C_4$) alkoxides) with ethoxide being preferred.

The ratio of metal cation to compound in a complex of the invention typically depends on the specific structure of the compound and the valence of the metal cation. In embodiments employing a solvent residue, the amount of such residue that is employed will typically depend on the above factors as well as the type of residue used. In preferred embodiments, the ratio of: (1) compounds of formulae (Ia) and/or (Ib) as defined by any of compounds (Iai), (Iaii), (Iaiii), (Iaiv), (Ibi), (Ibii), (Ibiii), and (Ibiv), respectively, or combinations thereof; to (2) one or more metal cation; to (3) solvent residue will typically be 2:1:4 or 2:2:2 for magnesium or sodium, respectively, and can otherwise vary depending upon the metal cation and compound used, and the crystalline packing forces respective thereto. Other ratios may be required depending on the charge of the cation and the type of complex embodiment In various embodiments, the compositions comprising the complexes may be essentially free from compounds represented by formula (Ib), as defined herein.

In these embodiments, the term "essentially free" preferably refers to such complexes formed with sodium as the metal cation comprising at least about 95 percent (w/w) of the compound represented by formula (Ia).

The compositions comprising the complexes described above preferably are in crystalline form.

In certain embodiments, the compositions comprising the complexes may employ the diastereomers of the compounds represented by formula (Ia) and, of applicable, the compounds represented by formula (Ib) according to any of the embodiments set forth hereinabove. In one non-limiting embodiment, for example, the concentration of compounds having the combination of the diastereomers $S_{xa}$—$R_{4z}$ and $S_{xb}$—$R_{4q}$ is from about 50 percent (w/w) to about 100 percent (w/w) of the composition, and the concentration of the compounds having the diastereomers $S_{xa}$—$R_{4q}$ and $S_{xb}$—$R_{4z}$ is from about 0 percent (w/w) to about 50 percent (w/w) of the composition, such that the sum of the total concentration of all such compounds is about 100 percent (w/w). Preferably, the concentration of such compounds having the combination of diastereomer pairs $S_{xa}$—$R_{4z}$ and $S_{xa}$—$R_{4q}$ is greater than about 70 percent Hydrates and solvates of the compounds of formulae (Ia) and (Ib) along with polymorphs thereof are also provided by the invention and may be formed according to techniques known to one having ordinary skill in the pharmaceutical arts. As an example, solvates of any embodiments encompassing the compounds represented by formula (Ia) may be made according to known techniques. Suitable solvents for use in providing the solvates are known in the art and may vary according to the particular embodiment. Exemplary solvents include alcohols, such as, without limitation, methanol, ethanol, and the like.

The invention also pertains to methods for providing each of the diastereomers $S_{xa}$—$R_{4q}$, $S_{xa}$—$R_{4z}$, $R_{xb}$—$R_{4q}$, and $S_{xa}$—$R_{4z}$ of the compounds of formulae (Ia) and/or (Ib), or pairs thereof, in resolved form. Preferably, in various embodiments, each diastereomer pair of compounds (Ia) and/or (Ib) are essentially free of the three other diastereomers, or combinations thereof, e.g., at least 95 percent (w/w).

As set forth herein, the compounds of (Ia) and (Ib) have been discovered to exhibit chirality at two distinct locations: (1) an atomic chiral center located at each sulfoxide group (as referenced by the first letter denoted in the diastereomer pair designation) and (2) a structural chiral center (i.e., a chiral plane) located at each pyridinal moiety on the compound (as referenced by the second letter denoted in the diastereomer pair designation). A preferred method for resolving each of the above diastereomer pairs involves first resolving the structural chiral center of the various materials used in making compounds (Ia) and/or (Ib) including those set forth herein. For example, the starting pyridine compound may be resolved at the $R_4$ position referred to herein, or alternatively one of the pyridinal-moiety containing intermediates can be resolved at the $R_4$ position such as, for example, a thiol compound represented by formulae (II) or (VIII). In this instance, the resolution of the thiol compound is carded out prior to oxidation which eventually forms compounds of formulae (Ia) and/or (Ib). The actual techniques for resolving the structural chiral centers may be carried out by various suitable methods.

Subsequent to oxidation, the materials used in making the compounds (Ia) and/or (Ib) are then be resolved at the atomic chiral center eventually providing each of the resolved diastereomer pairs of compounds (Ia) and/or (Ib). Any number of techniques may be used to resolve the atomic chiral center of these compounds, e.g., recrystallization from an optically active solvent, use of microorganisms, reactions with optically active acids forming salts which can be separated based on different solubilites of the diastereomers. Suitable optically active acids are, for example, the L- and D-forms of tartaic acid, di-o-tolyl-tartaric acid, malic acid, mandelic acid, camphorsulfonic acid or quinic acid.

In one embodiment, atomic chiral center resolution of the compounds of formulae (Ia) and (Ib) may be obtained by chromatographic techniques. Materials that may be used in this method include a cellulose (e.g., triphenylcarbamoyl-cellulose) coated on a column that includes a silica-containing material (e.g., silica or 3-aminopropyl silica). The column may be prepared by suspension in an organic solvent (e.g., methanol or 2-propanol) using an appropriate technique such as, for example, a descending slurry-packing technique.

Mobile phases for use in this procedure can be prepared by various methods, such as, for example, using n-hexane and diethylamine in different ratios. Other materials, however, may be employed such as, without limitation, alcohols (e.g., methanol, ethanol). The compounds of formulae (Ia) and/or (Ib) may be combined in the mobile phase along with other components known in the art such as, for example, a suitable buffer (e.g., a phosphate compound). The mobile phase is then passed through the column under processing (e.g., temperature, flow, and pressure) conditions that may be set by the operator. The diastereomer that first eluted from the column can be isolated by evaporation of the solvents. The diastereomer can be deemed isolated by known analytical techniques.

In another embodiment, the formation of compounds of formulae (Ia) and/or (Ib) having resolved atomic chiral centers may be formed by carrying out the asymmetric oxidation in an organic solvent of a pro-chiral sulphide according to the formula (X):

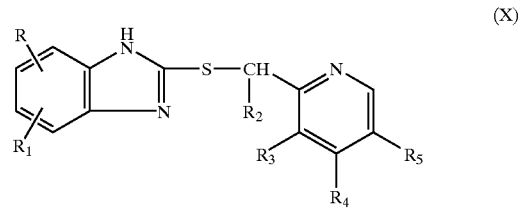

(X)

wherein R, $R_1$, $R_2$, $R_3$, $R_4$, and $R_5$ are defined above with R being present in the 6or 5-position, with an oxidizing agent and a chiral titanium complex, optionally in the presence of a base.

A number of oxidizing agents may be employed such as, for example, a hydroperoxide, more particularly tert-butylhydroperoxide or cumene hydroperoxide.

The titanium complex suitable for use in the reaction may be prepared using various methods. In one embodiment, the titanium complex is prepared from a chiral ligand and a titanium (IV) compound such as, for example, preferably titanium(IV) alkoxide, and optionally in the presence of water. An especially preferred titanium (IV) alkoxide is titanium (IV) isoperoxide or isopropoxide. Various amounts of chiral titanium complex may be used. Typically, an amount less than approximately about 0.5 equivalents is preferred and an especially preferred amount is about 0.05 to about 0.30 equivalents.

The titanium complex may also be prepared by reacting titanium tetrachloride with a chiral ligand in the presence of a base. The chiral ligand used in the preparation of the titanium complex is typically a branched or unbranched alkyl diol, or an aromatic diol. Preferred chiral diols are, for example, esters of tartaric acid, especially (+)diethyl L-tartrate or (−)-diethyl D-tartrate. It should be noted that thetitanium complex may be prepared in the presence of the compound of formula (X) or before the compound of formula (X) is added to the reaction vessel.

The oxidation is preferably carried out in the presence of a base. For example, the base may be an inorganic or organic base, such as, but not limited to, a hydrogen carbonate, an amide, or an amine such as guanidine or an amidine. Examples of other bases include triethylamine or N,N-diisopropylethylamine.

The oxidation is typically carried out in the presence of an organic solvent. The solvent can be selected with respect to suitable conditions. Suitable organic solvents include, but are not limited to, toluene, ethyl acetate, methyl ethyl ketone, methyl isobutyl ketone, diethyl carbonate, tert butyl methyl ether, tetra hydrofuran, methylene chlorde, and the like, and blends and mixtures thereof.

The oxidation is preferably carried out in the organic solvent at ambient temperature or just above ambient temperature, e.g., between about 20° C. and about 40° C. It is believed that the reaction times may be longer if the reaction is carried out below 20° C. The temperature of the reaction may be varied according to the intentions of one skilled in the art.

The products formed during the oxidation reaction may be extracted with an aqueous solution of ammonia or another N-containing base to avoid precipitation and/or formation of insoluble titanium salts. The aqueous phase is separated from the organic phase of the obtained mixture and the isolated aqueous phase is neutralized by the addition of a neutralizing agent resulting in the protonation of the diastereomers. The diastereomers may be extracted by an organic solvent. They may also be crystallized in an organic or aqueous solvent resulting in the desired resolved diastereomers of compounds (Ia) and/or (Ib).

In addition to using the above techniques to provide individual diastereomers $S_{xa}$—$R_{4q}$, $S_{xa}$—$R_{4z}$, $S_{xb}$—$R_{4q}$, and $S_{xb}$—$R_{4z}$, these techniques may be used to provide various combinations of diastereomers as set forth herein, including, without limitation, those which are essentially free from other diastereomers.

The invention also provides for methods of making salts of diastereomers and pairs thereof. A preferred method for making the salts of the individual diastereomers and/or pairs thereof first involves forming these diastereomers of pairs thereof according to the teachings of the preceding section, in which the chiral plane is first resolved followed by resolution of the sulfoxide atomic chiral center. Salts of these resolved diastereomers or pairs thereof may then be formed according to various techniques.

Examples of salts of diastereomers or pairs thereof that may be obtained include, but are not limited to, alkali and alkaline metal salts. As an example, to obtain optically pure alkali salts of the compounds of formulae (Ia) and/or (Ib), the diastereomer obtained in a manner described herein, may be treated with: (1) a base, such as for example, $M_1^+OH$ wherein $M_1$ is sodium, ammonium, potassium, or lithium, in a aqueous or nonaqueous medium; (2) $M_1^+OR^2$ wherein $M_1^+$ is defined above, and $R^2$ is an alkyl group containing 1 to 4 carbon atoms; or (3) $M_1^+NH_2$ wherein $M_1^+$ is defined above. In order to obtain the crystalline form of the alkali salts, addition of the base $M_1^+OH$ in a non-aqueous medium such as a mixture of 2-butanone and toluene, is preferred.

To obtain an optically pure alkaline metal salt of a diastereomer or pair thereof of the compounds of formulae (Ia) and/or (Ib), the optically pure alkali salt is treated with an aqueous solution of an inorganic alkaline metal salt such as, for example, $M_2^{2+}Cl_2$ wherein $M_2^{2+}$ is an alkaline metal such as calcium, magnesium, strontium, barium, and the like, whereupon the alkaline metal salt of the single enantiomer is precipitated. The optically pure alkaline metal salts may also be prepared by treating a single enantiomer of compounds of formulae (Ia) and/or (Ib) with a base such as, for example, $M_2^{2+}(OR^3)_2$ wherein $R^3$ is an alkyl group containing 1 to 4 carbon atoms, in a non-aqueous solvent such as alcohol (for alcoholates), or in an ether such as tetratiydrofuran.

A preferred embodiment for the preparation of the magnesium salts of the $S_{xa}$—$R_{4q}$ or $S_{xa}$—$R_{4z}$ diastereomer or pairs thereof of the compounds of formulae (Ia) and/or (Ib) polyhydrates comprises: a) treating a magnesium salt of the above individual diastereomer or pairs thereof of such compounds with water at a suitable temperature for a suitable time. The phrase "a suitable temperature" means a temperature which induces the transformation of starting material to product without decomposing any of these compounds. Examples of such suitable temperatures include, but are not limited to, ambient temperature. By a suitable time is meant a time that results in high convention of the starting material into product without causing any decomposition of either compound, i.e., results in a good yield. This suitable time will vary depending upon the temperature used in a way well known to people in the art. By increasing the temperature, less time is required to give the desired conversion. The amount of water is generally not crucial and will depend on the process conditions used. The magnesium salts of the above diasteraomer pairs thereof of the compounds of formulae (Ia) and/or (Ib) polyhydrates is thereafter separated from the aqueous slurry, for example, by filtration or centrifugation and thereafter dried to constant weight.

Optionally, the process may comprise: b) oxidizing compounds of formula (II) defined herein, with an oxidizing agent and a chiral titanium complex, optionally in the presence of a base. The oxidation is carried out in an organic solvent, for example, toluene or dichloromethane. The crude product is then converted to the corresponding potassium salt (or, for example, sodium salt as a replacement for each occurrence of potassium salts) by treatment with a potassium source, such as methanolic potassium hydroxide or methanolic potassium methylate, followed by isolation of the formed salt.

The resulting potassium salts of the $S_{xa}$—$R_{4q}$ or $S_{xa}$—$R_{4z}$ diastereomers, or combinations thereof, of the compounds of formulae (Ia) and/or (Ib) are thereafter converted to the corresponding magnesium salts by treatment with a magnesium source, such as, for example, magnesium sulfate in a lower alkyl alcohol, such as methanol. The solution is optionally filtered and the precipitation is initialized by addition of a non-soluble solvent such as acetone. The product is filtered off and optionally washed with water and further processed as is described in a) above. Alternatively, the potassium salts may be treated with a magnesium source, such as, for example, magnesium sulfate in water, and isolation of the magnesium salts of the $S_{xa}$—$R_{4q}$ or $S_{xa}$—$R_{4z}$ diastereomers or pairs thereof of the compounds of formulae (Ia) and/or (Ib) polyhydrates, or any other conventional technique for transforming a potassium salt to the corresponding magnesium-salt can be used.

The potassium salts of the $S_{xa}$—$R_{4q}$ or $S_{xa}$—$R_4$ diastereomers, or pairs thereof, of the compounds of formulas (Ia) and/or (Ib) are suitable intermediates in the preparation of the magnesium salts of these diastereomers of pairs thereof. The potassium salts of these diastereomers may also be used as active components in pharmaceutical formulations to be used in the treatment of various diseases described herien, particularly gastric acid related diseases.

To establish and quantitate the ratio of the 5- and 6-methoxy isomers of omeprazole API, including the novel ratios of such isomers of the present invention (the "modified omeprazole compounds"), a Raman spectrographic method was developed using a FT-Raman spectrometer (Nicolet Nexus 670 with an FT-Raman accessory, 1064 nm laser, and a step and repeat sampling device; Nicolet Instruments Corp., Madison, Wis.). The present method is conducted in three steps: preparation of standards, establishing a standard curve, and analysis of samples.

Typically, a minimum of 4 to 5 standards are prepared. In the present method, seven standards were prepared using the methods set forth in Examples 1, 1a, 36, 37, 41, and 44 herein, plus a commercially available sample of omeprazole purchased from the United States Pharmacopia (USP). In addition to the USP standard, it is necessary to use a standard which is very low in 5-methoxy isomer concentration, preferably in pure form, one which has a high concentration of 5-methoxy isomer such as in the range of about 40%, and a series of at least two other standards distributed over the range from about 5% to about 25%. To establish the standard curve, each standard is run in at least triplicate using the step and repeat sampling device operating in the continuous mode with 15 replicates for each standard preparation and 500 scans per replicate, using a resolution of 2 cm$^{-1}$, and a laser power of about 0.7 watt, under instrumental parameters set to generate an acceptable S/N.

For each of the selected standards, other than the "pure" 6-methoxy isomer, a deconvolution algorithm (self-Fourier deconvolution software; such as, for example, TQ Analyst™ from Nicolet Instruments Corporation) is used to deconvolute the peak areas of the peaks at about 1365 cm$^{-1}$ (the 5-methoxy isomer) and 1354 cm$^{-1}$ (the 6ethoxy isomer). The pure 6methoxy isomer (Example 1 a) only shows a simple peak at 1354 cm$^{-1}$ and as such the percent 6-methoxy isomer is set at a concentration of 100%. Using such an algorithm, the area percent of the 6-methoxy isomer of each standard having both the 5- and 6-methoxy isomer is determined. The standard deviation for each set of replicates is less than about 0.7% and the average. Standard deviation for the average of all runs and replicates of a given standard is less than about 0.7% or the resulting data should be investigated.

A software program capable of analyzing Raman spectra in a partial least squares format such as, for example, Nicolet's TQ Analysts™, is used to generate a standard curve using the average determined percent 6-methoxy isomer values and the spectrum of a given standard. Correlation coefficients should be at or above about 0.98 among all standards.

Each API sample is then analyzed using the method similar to that described for establishing the standards, except at least triplicate preparations with at least five replicates per sample preparation, and at least 100 scans per replicate with triplicate preparations per sample. Using the above-referenced partial least squares analysis, the percent 6-methoxy isomer, and thus the percent 5-methoxy isomer is determined for each scan and the average of the spectra is calculated. The standard deviation (SD) for each set of replicates is less than about 1.0%, and the average standard deviation of all runs and replicates of a given sample is less than about 1.0%. If the standard deviation is above 1.0%, the results should be investigated. High standard deviation values are an indication of variability which may be caused by small amounts of sample burning. If this is suspected, the preparation should be run again.

Using the methods taught above, results from establishing the standard curve are as follows:

| Standard Example/Sample | % 5-isomer | % 6-isomer |
| --- | --- | --- |
| Example 1a | 0.000 | 100.000 |
| Example 1 | 5.875 | 94.125 |
| Standard Deviation (SD) | 0.338 | |
| USP | 7.250 | 92.750 |
| SD | 0.556 | |
| Example 37 | 12.246 | 87.754 |
| SD | 0.505 | |
| Example 36 | 16.005 | 83.995 |
| SD | 0.501 | |
| Example 41 | 16.414 | 83.587 |
| SD | 0.597 | |
| Example 44 | 41.258 | 58.742 |
| SD | 0.328 | |

Using the API quantitative method taught above, three randomly selected lots of omeprazole API (commercial API lots from Merck and Company, Raway, N.J.) were analyzed. Results are as follows:

| Sample/Lot | % 5-isomer | % 6-isomer |
| --- | --- | --- |
| 01 | 7.50 | 92.50 |
| SD | 0.75 | |
| 02 | 8.02 | 91.98 |
| SD | 0.56 | |
| 03 | 7.61 | 92.39 |
| SD | 0.81 | |

Results from these data via the above-described quantitative method again confirms that the compound known as omeprazole is not 5-methoxy-2-[[(4-methoxy-3,5dimethyl-2-pyridinyl)methyl]sulfinyl]-1H-benzimidazole as previously designated, but, rather, using the USP standard for omeprazole as well as three lots of omeprazole API from the sole United States manufacturer of omeprazole, is in fact (5)6-methoxy-2-[[(4-methoxy-3,5dimethyl-2-pyridinyl) methyl]sulfinyl]-1H-benzimidazole in a tightly defined ratio of about 93:7± about 2% of the 6-methoxy isomer and 5-methoxy isomer, respectively. Accordingly, the present invention provides pure 6-methoxy-2[[(4-methoxy-3,5-dimethyl-2-pyridinyl)methyl]sulfinyl]1H-benzimidazole (6-methoxy omeprazole), which is essentially free of 5-methoxy-2-[[(4-methoxy-3,5-dimethyl-2-pyridinyl) methyl]sulfinyl]-1H-benzimidazole, and (5)6-methoxy-2-[[(4methoxy-3,5-dimethyl-2-pyridinyl)methyl]sulfinyl]-1H-benzimidazole in the ratios set forth herein, and the methods and formulations further set forth herein.

Furthermore, an additional method for establishing the ratio of the 5- and 6-methoxy isomers of omeprazole API, albeit less precise than the quantitative FT-Raman method previously described herein, as well as ratio of the 5- and 6-methoxy isomers in omeprazole drug product was developed. This method also used an FT-Raman spectrometer (Nicolet Nexus 670 with an FT-Raman accessory, 1064 nm laser, and a step and repeat sampling device). This method, too, is conducted in three stages: preparation of standards, establishing a standard curve, and analysis of samples.

Typically a minimum of 4 to 5 standards are prepared. The present FT-Raman method for API and drug product analysis uses the same method set forth above to prepare and establish the standard curve, inducing preferred aspects, as the method set forth for the more quantitative API method relative to the number of preparations, replicates, and scans per replicate of each standard, resolution, sampling device, deconvolution of standard peaks, determination of peak area, and standard deviation for each set of replicates and the average of all runs and replicates of a given standard.

Rather than a partial least squares analysis, however, a software program capable of analyzing Raman spectra in a corrected classical least squares format, for example, Nicolets TQ Analyst™, is used to generate a standard curve using the average determined percent 6-methoxy isomer values and the peak height ratio of a given pair of peaks in a standard. In general, the method is performed by a ratio of a peak related to the 6-methoxy isomer (about 1627 cm$^{-1}$) to a suitable internal omeprazole band (about 1587 cm$^{-1}$). In the event the presence and magnitude of matrices from pharmaceutical excipients in drug product interfere with the resolution of the peak related to the 6-methoxy isomer and/or the preferred internal omeprazole band, other sets of bands at such as, for example, about 1587 cm$^{-1}$ and 1201 cm$^{-1}$, respectively, and 1185 cm$^{-1}$ and 1512 cm$^{-1}$ respectively, are used. Correlation coefficients of the standard curve are at or above about 0.95 among all standards.

For omeprazole API, each sample is prepared under the same instrument conditions as the standards except it is preferred to use at least triplicate preparations with at least five replicates per sample preparation and at least 100 scans per replicate. Using the above-referenced corrected classical least squares analysis, the percent 6-methoxy isomer, and thus the percent 5-methoxy isomer, is determined for each scan, and the average of the 15 spectra is calculated. The standard deviation for each set of replicates is less than about 2.0%, and the average standard deviation of all runs and replicates of a given sample is less than about 2.0% or the sample run should be investigated.

For omeprazole drug product, capsules and tablets are similarly prepared. For capsules, a sufficient number of capsules, preferably about 5–10 capsules, are opened and the omeprazole beads are emptied into an appropriate container. The container is gently rolled to mix the beads or powder, as appropriate, from the various capsules to provide a generally homogeneous blend. For tablets, a sufficient number of tablets, preferably about 5–10 tablets, are gently ground (vigorous grinding may affect the ratio of 5- and 6-methoxy isomers in omeprazole), and blended to provide a generally homogeneous blend of the ground material.

Each appropriate composite sample is analyzed under the same instrument conditions as the standards, adjusting to an appropriate laser wattage to compensate for the presence of excipients. For FT-Raman analysis, each sample preparation (the composite from capsules or tablets) is run using at least triplicate preparations with at least three replicates and at least 500 scans per replicate. Using a corrected classical least squares analysis, the percent 6-methoxy isomer, and thus the percent 5-methoxy isomer, is determined for each scan, and the average of the 9 spectra is calculated. The standard deviation for each set of replicates is less than about 3.0%, and the average standard deviation of all runs of a given sample is less than about 3.0% or the sample run should be investigated.

Although the partial least squares method described above for API is more accurate than this classical least squares method, the deconvolution of the peaks related to the 5- and 6-methoxy isomers remains the same for both methods and, thus, the standards curve used to develop each remains the same. Results from API sample analysis with the classical least squares method shows a slightly lower bias than the results from using the partial least squares method, but the data from the partial least squares analysis of omeprazole API samples-confirms the validity of this method for a generally quantitative method for determining the ratio of 5- and 6-methoxy isomers in omeprazole drug product (Prilosec®) which is commercially available via prescription. The drug product used in the present classical least squares method was provided by Merck and Company, Raway, N.J.

Results from API analysis of the three randomly selected lots of omeprazole API used in the previous partial least squares were calculated using the classical least squares methods are as follows:

| Sample/Lot | % 5-isomer | % 6-isomer |
|---|---|---|
| 01 | 6.14 | 93.86 |
| SD | 0.97 | |
| 02 | 6.56 | 93.44 |
| SD | 1.10 | |
| 03 | 6.40 | 93.60 |
| SD | 1.21 | |

When applying this classical least squares analytical method to drug product, it was unexpectedly discovered that the ratio of 5- and 6-methoxy isomers of omeprazole, and thus, it is believed for other compounds represented by formulae (Ia) and/or (Ib), as active pharmaceutical ingredient(s) can be significantly influenced by a multitude of factors during the preparation of drug product (final pharmaceutical formulations for administration, preferably in unit dosage form).

For the sole omeprazole drug product registered by the U.S. Food and Drug Administration and sold in the United States (Prilosec®), the ratio of the 6- and 5-methoxy isomers in API typically shifts from a ratio of about 93:7 (+/− about 2%), respectively, to a ratio in drug product of about 86:14 (+/− about 3%), respectively. Factors such as mechanical manipulation (e.g., grinding or, potentially, aggressive sieving) and, particularly the use of commonly used, wet granulation processes during drug product preparation have likely contributed to this significant and unexpected shift. Accordingly, shifts from the more thermodynamically stable compounds of the present invention having a higher percentage of the 6-methoxy isomer (with the pure 6-methoxy isomer being preferred) to the less stable compounds of the present invention having increasing concentrations, of the 5-methoxy isomer in the same composition can affect the stability and dissolution profiles of drug product Compounds and pharmaceutical formulations of the present invention having such higher percentage of such 6-methoxy isomer provide greater stability whereas those having such increasing percentage of such 5-methoxy isomer provide more rapid dissolution.

Using the classical least squares analytical method described above, results for Prilosec® drug product are as follows:

| Prilosec Dosage | % 5-isomer | % 6-isomer |
| --- | --- | --- |
| 20 mg | 14.7 | 85.3 |
| SD | 2.3 | |
| 20 mg | 14.5 | 85.5 |
| SD | 2.0 | |
| 20 mg | 14.7 | 85.3 |
| SD | 3.0 | |
| 40 mg | 13.2 | 86.8 |
| SD | 1.6 | |
| 40 mg | 12.9 | 87.1 |
| SD | 0.9 | |
| 10 mg | 13.6 | 86.4 |
| SD | 2.8 | |
| 10 mg | 13.3 | 86.7 |
| SD | 2.4 | |

In addition, a homogeneous dry blend pharmaceutical formulation of the above-referenced omeprazole API from Merck and Company and mannitol was prepared with an equivalent dose of 20 mg per dosage form, preferably an enterically coated capsule as set forth herein. The above-referenced FT-Raman analytical method was used to determine the ratio of a composition of 6-methoxy-2-[[(4methoxy-3,5-dimethyl-2-pyridinyl)methyl]sulfinyl]-1H-benzimidazole to 5-methoxy-2-[[(4-methoxy-3,5-dimethyl-2-pyridinyl)methyl]sulfinyl]-1H-benzimidazole in such pharmaceutical formulation compared to the ratio of such compounds in the corresponding active pharmaceutical ingredient using the classical least squares FT-Raman analytical method for API set forth above. It was unexpectedly discovered that the ratio of the two compounds in API (about 93–94%:6–7% for the 6-methoxy isomer to the 5-methoxy isomer, respectively) was essentially the same as the ratio of the composition of the 6-methoxy isomer to the 5-methoxy isomer in the dry blended pharmaceutical formulation. These data were unexpected, because, as demonstrated above, the percentage of the 6-methoxy isomer of omeprazole significantly decreases and the percentage of the 5-methoxy isomer significantly increases when such a composition of such Merck and Company API is formulated as Prilosec® drug product.

Accordingly, in order to utilize the benefits of higher percentages of the 6- and 5-methoxy isomers of omeprazole as set forth herein, and to maintain the desired ratio of the 6- and 5-methoxy isomers of compositions and complexes of the present invention in the appropriate drug product, including the unit dosage forms taught herein, the present invention further provides pharmaceutical formulations comprising a non-toxic amount of a composition of at least one compound represented by formula (Ia) and, optionally, at least one compound represented by formula (Ib) or one or more pharmaceutically acceptable salts, solvates, hydrates, or combinations of such compounds represented by formulae (Ia) and (Ib), and at least one non-aqueous pharmaceutically acceptable carrier, diluent, or excipient, wherein the ratio of said compound represented by formula (Ia) and said compound represented by formula (Ib) in said composition is essentially the same as the ratio of said compound is represented by formula (Ia) and said compound is represented by formula (Ib) in the active pharmaceutical ingredient used in said pharmaceutical formulation.

As used in this context, the term "essentially the same" means that the API to active ingredient in drug product ratio of 6- to 5-methoxy isomers of compounds represented by formulae (Ia) and (Ib), respectively, does not vary by more than +/- five percentage points (w/w). For example, for an API having a 6- to 5-methoxy isomer ratio of about 95:5 (w/w), the active ingredient ratio in the corresponding drug product is from about 1 00:0 to about 90:0 (w/w), respectively.

Typical non-aqueous carriers, diluents, and excipients include, for example, mannitol, lactose, and the like. In addition, any of the dry blend formulations taught herein can optionally include one or more stabilizing agents which are well known in the art. A preferred stabilizing agent is pelletized sodium hydroxide which is homogeneously blended with the homogeneous dry blended formulations of the present invention prior to preparation of the final dosage form. Preferred final dosage forms (drug product) of these dry blended pharmaceutical formulations are those which are set forth herein, including preferred unit dosage forms and dosage strengths.

A preferred compound represented by formula (Ia) is 6-methoxy-2-[[(4-methoxy-3,5-dimethyl-2-pyridinyl)methyl]sulfinyl]-1H-benzimidazole, in pure form, essentially free of 5-methoxy-2[[(4-methoxy-3,5-dimethyl-2-pyridinyl)methyl]sulfinyl]-1H-benzimidazole, and as a composition with 5-methoxy-2-[[(4-methoxy-3,5dimethyl-2-pyridinyl)methyl]sulfinyl]-1H-benzimidazole as taught herein. A preferred compound represented by formula (Ib) is 5-methoxy-2-[[(4methoxy-3,5-dimethyl-2-pyridinyl)methyl]sulfinyl]-1H-benzimidazole.

The present invention further provides pharmaceutical formulations wherein said preferred 6-methoxy-2-[[(4-methoxy-3,5-dimethyl-2-pyridinyl)methyl]sulfinyl]-1H-benzimidazole is present in said compositions at a concentration less than about 83% (w/w) and, in another preferred embodiment in a concentration greater than about 89% (w/w), each relative to the corresponding 5-methoxy isomer such that the sum of such 6-methoxy isomer and such 5-methoxy isomer equals 100%.

Further provided are methods for essentially maintaining the desired active ingredient ratio of a composition comprising a compound represented by formula (Ia), preferably 6-methoxy-2-[[(4methoxy3,5dimethyl-2-pyridinyl)methyl]sulfinyl]-1H-benzimidazole, and, optionally, a compound represented by formula (Ib), preferably 5-methoxy-2 [[(4methoxy-3,5-dimethyl-2-pyridinyl)methyl]sulfinyl]-1H-benzimidazole, or one or more pharmaceutically acceptable salts, solvates, hydrates, or combinations f such compounds represented by formulae (Ia) and (Ib), in a pharmaceutical formulation compared to the ratio of said compounds represented by formulae (Ia) and (Ib) in the active pharmaceutical ingredient used in said pharmaceutical formulation comprising dry blending said composition of active pharmaceutical ingredient with at least one non-aqueous pharmaceutically acceptable carrier, diluent, or excipient. Preferred compositions and ratios of said compounds are as set forth above for drug product and herein.

Such dry blend pharmaceutical formulations of the present invention, particularly in unit dosage form are used of r treating the disease states described herein. As such, the present invention further provides methods of treating a subject (e.g., mammals, particularly humans) comprising administering to a subject in need of treatment (including prophylaxis) of gastic acid related diseases/disease states via the inhibition of gastric acid, as further discuss ed herein, a therapeutically effective, non-toxic amount of the aforementioned pharmaceutical formulations. Preferred compounds and compositions, as active ingredients, unit dosage forms, and dosage strengths are as set forth herein.

The present invention also encompasses other pharmaceutical formulations comprising a t least one active pharmaceutical ingredient of the present invention and at least one pharmaceutically acceptable carrier, diluent, or excipient, or combination thereof, the selection of which is known to the skilled artisan. For the purposes of the invention, the term "active ingredient" refers to any of the embodiments set forth herein referring to the compound(s) of formulae (Ia) and/or (Ib diastereomers thereof, any combinations of diastereomers thereof, pharmaceutically acceptable salts thereof, along with complexes, hydrates, solvates, and polymorphs of any of the above, as well as any combinations thereof as well as compositions thereof. Prodrugs of any of these active pharmaceutical ingredients may also be employed for the purposes of the invention, most preferably as part of a pharmaceutical formulation wherein said prodrug is mentabolized, in vivo, to the pharmaceutically active moiety, although their use in other embodiments may be carried out. The term "active ingredient" also encompasses, in one embodiment, a said pharmaceutical composition of the present invention which is blended with at least one pharmaceutically acceptable excipient, diluted by an excipient or enclosed within such a carrier that can be in the form of a capsule, sachet, tablet buccal, lozenge, paper, or other container. When the excipient serves as a diluent, it may be a solid, semi-solid, or liquid material which acts as a vehicle, carrier, or medium for the active ingredient. Thus, the formulations can be in the form of tablets, pills, powders, elixirs, suspensions, emulsions, solutions, syrups, capsules (such as, for example, soft and hard gelatin capsules), suppositories, sterile injectable solutions, and sterile packaged powders.

Examples of suitable excipients include, but are not limited to, starches, gum arabic, calcium silicate, microcrystalline cellulose, polyvinylpyrrolidone, cellulose, water, syrup, and methyl cellulose. The formulations can additionally include lubricating agents such as, for example, talc, magnesium stearate and mineral oil; wetting agents; emulsifying and suspending agents; preserving agents such as methyl- and propyl hydroxybenzoates; sweetening agents; or flavoring agents. Polyols, buffers, and inert fillers may also be used. Examples of polyols include, but are not limited to: mannitol, sorbitol, xylftol, sucrose, maltose, glucose, lactose, dextrose, and the like. Suitale buffers encompass, but are not limited to, phosphate, citrate, tartarate, succinate, and the like. Other inert fillers which may be used encompass those which are known in the art and are useful in the manufacture of various dosage forms. If desired, the solid pharmaceutical compositions may include other components such as bulking agents and/or granulating agents, and the like. The compositions of the invention can be formulated so as to provide quick, sustained, or delayed release of the active ingredient after administration to the patient by employing procedures well known in the art In the event that the above formulations are to be used for parenteral administration, such a formulation typically comprises sterile aqueous and non-aqueous injection solutions comprising the active ingredient, for which preparations are preferably isotonic with the blood of the intended recipient These preparations may contain anti-oxidants, buffers, bacteriostats, and solutes which render the formulation isotonic with the blood of the intended recipient Aqueous and non-aqueous sterile suspensions may include suspending agents and thickening agents. The formulations may be presented in unit-dose or multidose containers, for example sealed ampules and vials. Extemporaneous injection solutions and suspensions may be prepared from sterile powders, granules and tablets of the kind previously described.

In certain embodiments of the invention, the active ingredient may be made into the form of dosage units for oral administration. The active ingredient may be mixed with a solid, pulverant carrier such as, for example, lactose, saccharose, sorbitol, mannitol, starch, amylopectin, cellulose derivatives or gelatin, as well as with an antifriction agent such as, for example, magnesium stearate, calcium stearate, and polyethylene glycol waxes. The mixture is then pressed into tablets. If coated tablets are desired, the above prepared core may be coated with a concentrated solution of sugar, which may contain gum arabic, gelatin, talc, titanium dioxide, or with a lacquer dissolved in volatile organic solvent or mixture of solvents. To this coating, various dyes may be added in order to distinguish among tablets with different active compounds or with different amounts of the active compound present Soft gelatin capsules may be prepares in which,capsules contain a mixture of the active ingredient and vegetable oil or non-aqueous, water miscible materials such as, for example, polyethylene glycol and the like. Hard gelatin capsules may contain granules of the active ingredient in combination with a solid, pulverant carrier, such as, for example, lactose, saccharose, sorbitol, mannitol, potato starch, corn starch, amylopectin, cellulose derivatives, or gelatin.

Dosage units for rectal administration may be prepared in the form of suppositories which may contain the active ingredient in a mixture with a neutral fat base, or they may be prepared in the form of gelatin-rectal capsules which contain the active substance in a mixture with vegetable oil or paraffin oil.

Liquid preparations for oral administration may be prepared in the form of syrups or suspensions, e.g., solutions containing an active ingredient, sugar, and a mixture of ethanol, water, glycerol, and propylene glycol. If desired, such liquid preparations may contain coloring agents, flavoring agents, and saccharin. Thickening agents such as carboxymethylcellulose may also be use.

Solutions for parenteral administration by injection may be prepared as an aqueous solution of a water soluble, pharmaceutically acceptable salt of the active ingredient. These solutions may also contain stabilizing agents and/or buffering agents and may be manufactured in different dosage unit ampules.

Tablets for oral use are typically prepared in the following manner, although other techniques may be employed. The solid substances are gently ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for determined length of time to achieve a desired particle size and consistency. The granules of the dried mixture are gently sieved to remove any powder. To this mixture, disintegrating, antifriction, and anti-adhesive agents are added. Finally, the mixture is pressed into tablets using a machine with the appropriate punches and dies to obtain the desired tablet size. The operating parameters of the machine may be selected by the skilled artisan.

Typically, preparation of lozenge and buccal dosage forms are prepared by methods known to one of ordinary skill in the art.

In a particular embodiment, the active ingredient may be present in a core surrounded by one or more layers including an enteric coating layer. With respect to formation of the core, the active ingredient is typically mixed with inert, preferably water soluble, conventional pharmaceutically acceptable constituents to obtain the preferred concentration of the active ingredient in the final mixture with an alkaline reacting, otherwise inert, pharmaceutically acceptable substance (or substances), which creates a "micro-pH" around each particle of active compound of not less than a pH of 7, preferably not less than a pH of 8, when water is adsorbed to the particles of the mixture or when water is added in small amounts to the mixture. Such substances can be chosen among, but are not limited to, sodium, potassium, calcium, magnesium, and aluminum salts of phosphoric acid, carbonic acid, citric acid, or other suitable weak inorganic or organic acids; substances typically used in antacid preparations such as aluminum, calcium, and magnesium hydroxides; magnesium oxide or composite substances such as, for example, $Al_2O_3 6MgO\ CO_2 12H_2O$ $(Mg_6Al_2(OH)_{16}CO_3 4H_2O)$, $MgOAl_2O_3$, $2SiO_2 nH_2O$, wherein n is not necessarily a whole number and may be less than 2, or similar compounds; organic pH-buffering substances such as trihydroxymethylamino-methane or other similar, pharmaceutically acceptable pH-buffering substances. The stabilizing high pH-value in the powder mixture can also be achieved by using an alkaline reacting salt of the active compound such as, but not limited to, sodium, potassium, magnesium, and calcium salts of active ingredient, either alone or in combination with a conventional buffering substance as previously described.

The powder mixture may then be formulated into small beads, i.e., pellets or tablets, by conventional pharmaceutical procedures. The pellets, tablets, or gelatin capsules may then be used as cores for further processing.

The reacting cores containing the active ingredient may be separated from the enteric coating polymer(s) containing free carboxyl groups, that otherwise is capable of causing degradation/discoloration of the active compound during the coating process or during storage. The subcoating layer (i.e., the separating/barrier layer), also serves as a pH-buffering zone to contain sufficient buffer capacity such that hydrogen ions diffusing from the outside in towards the core can react with hydroxyl ions diffusing from the core towards the surface of the coated article. The pH-buffering properties of the separating layer can be further strengthened by introducing in the layer substances chosen from a group of compounds usually used in antacid formulations described above. The separating layer usually consists of one or more water soluble inert layers, optionally containing pH-buffering substances.

The separating layer(s) can be applied to the cores, typically in the form of pellets or tablets, by conventional coating procedures in a suitable coating pan or in a fluidized bed apparatus using water and/or conventional organic solvents for the coating solution. The material for the separating layer may be chosen among the pharmaceutically acceptable water soluble, inert compounds or polymers used for film-coating applications such as, for example, sugar, polyethylene glycol, polyvinylpyrrollidone, polyvinyl alcohol, hydroxypropyl cellulose, hydroxymethyl cellulose, hydroxypropyl methylcellulose, or the like. The thickness of the separating layer may be determined according to the skilled artisan.

In the case of tablets, another method to apply the coating can be performed by the dry coating technique. First, a tablet containing the active ingredient is compressed as described herein. Around this tablet, another layer is compressed using a suitable tableting technique machine. The outer, separating layer, contains pharmaceutically acceptable, in water soluble or in water, rapidly disintegrating tablet excipients. Conventional plasticizers, pigments, titanium dioxide talc, and other additives may be included in the separating layer. In embodiments encompassing gelatin capsules, the gelatin capsule itself serves as a separating layer.

The enteric coating layer is typically applied on to the subcoated cores by conventional coating techniques such as, for example, pan coating or fluidized bed coating using solutions of polymers in water and/or suitable organic solvents or by using latex suspensions of the polymers. Enteric coating polymers that can be used include, for example, cellulose acetate phthalate, hydroxypropyl methylcellulose phthalate, polyvinyl acetate phthalate, carboxymethylethylcellulose, co-polymerized methacrylic acid/ methacrylic acid methyl esters such as, for example, compounds known under the trade name Eudragit®L 12,5 or Eudragit®L 100 (Röhm Pharma of Darmstadt, Germany), or other similar compounds. The enteric coating can also be applied using water-based polymer dispersions, e.g. Aquateric® (FMC Corporation of Chicago, Ill.), Eudragit®L100-55 (Röhm Pharma or Darmstadt, Germany), Coating CE 5142 (BASF of Mount Olive, N.J.). The enteric coating layer can optionally contain a pharmaceutically accptabcle plasticizer such as, for instance, cetanol, triacetin, citric acid esters such as, for example, those known under the trade name Citroflex® (Pfizer of New York, N.Y.), phthalic acid esters, dibutyl succinate or similar plasticizers. The amount of plasticizer is usually optimized for each enteric coating polymer(s). Dispersants such as talc, colorants and pigments may also be included in the enteric coating layer.

Thus, the formulations described by the above embodiments comprise cores containing at least one active ingredient described herein, optionally mixed with an alkaline reacting compound, or cores comprising a salt of at least one active ingredient or one or more enantiomers thereof as taught herein, or one or more pharmaceutically acceptable salts, hydrates, solvates, polymorphs, or combinations thereof, optionally mixed with an alkaline reacting compound. The alkaline reacting core material and/or alkaline salt of the active ingredient is believed to potentially enhance the stability of the active ingredient. The cores suspended in water form a solution or a suspension which has a pH which is higher than that of a solution in which the polymer used for enteric coating is just soluble. The cores may be coated with an inert reacting water soluble or in water rapidly disintegrating coating, optionally containing a pH-buffering substance, which separates the cores from the enteric coating. Without this separating layer, the resistance towards gastric juice may be too short and/or the storage stability of the dosage form would be unacceptably short The sub-coated dosage form is finally coated with an enteric coating rendering the dosage form insoluble in acid media, but rapidly disintegratng/dissolving in neutral to alkaline media such as, for instance, the liquids present in the proximal part of the small intestine.

The final dosage form encompassing the above embodiments may be either an enteric coated tablet or capsule or in the case of enteric coated pellets, pellets dispensed in hard gelatin capsules or sachets or pellets formulated into tablets. It is desirable for long term stability during storage that the water content of the final dosage form containing the active ingredient (enteric coated tablets, capsules or pellets) be kept low. As a consequence, the final package containing hard gelatin capsules filled with enteric coated pellets preferably also contain a desiccant, which reduces the water content of the gelatin shell to a level where the water content of the enteric coated pellets filled in the capsules does not exceed a certain level.

Accordingly, the compounds and compositions of the present invention are preferably formulated in a unit dosage form, each dosage containing from about 5 mg to about 60 mg, and more preferably the amount set forth herein. The term "unit dosage form" refers to physically discrete units, such as capsules or tablets suitable as unitary dosages for human patients and other mammals, each unit containing a predetermined quantity of one or more active ingredient(s) calculated to produce the desired therapeutic effect, in association with at least one pharmaceutically acceptable carrier, diluent, excipient, or combination thereof. Generally, preferred dosages of active ingredient(s) in such unit dosage forms are from about 8 mg to about 10 mg, about 16 mg to about 20 mg, and about 32 mg to about 40 mg, especially 10 mg, 20 mg, and 40 mg per dosage unit.

In another aspect the invention provides a complex comprising any of the active ingredients as defined hereinabove and at least one cyclodextrin. Most preferably, the complex is in the form of an inclusion complex. As used herein, the term "active ingredient" refer to any of the embodiments set forth herein referring to the compound(s) of formulae (Ia) and/or (Ib), diastereomers thereof, any combinations of diastereomers thereof, pharmaceutically acceptable salts thereof, along with complexes, hydrates, solvates, and polymorphs of any of the above, as well as any compositions thereof, and combinations of any of the above. For the purposes of the invention, the term "cyclodextrin" is to be broadly construed and include, without limitation, alpha-cyclodextrins, beta-cyclodextrins, and gamma-cyclodextrins. An example of a description of cyclodextrin is provided in The Merck Index, $12^{th}$ Ed., (p. 458) 1996. As known in the art, cyclodextrins are cyclic origosacoharides typically consisting of 6, 7, or 8 glucose units. The glucose units are linked by alpha-1,4-glucassdic bonds. As a consequence of the chair formation of the sugar units, all secondary hydroxyl groups (e.g., at $C_2$ and $C_3$) are located on one side of the ring, while all the primary hydroxyl groups at $C_3$ are situated on the other side. As a results the external faces are hydrophilic, making the cyclodextrins water-soluble. In contrast, the cavities of the cyclodextrins are hydrophobic, since they are lined by the hydrogen of atoms $C_3$, $C_5$, and by ether-like oxygens. Also encompassed under the definition of cyclodextrin are derivatives of cyclodextrins. In various embodiments, the 18 to 24 hydroxyl groups of the respective cyclodextrin molecules are the starting points for the synthesis of such derivatives. Using known techniques, methyl-, ethyl-, hydroxyethyl-, hydroxymethyl, and hydroxypropyl substituted cyclodextrins may be utilized.

Examples of cyclodextrins that may be used include, without limitation, hydropropyl-beta-cyclodextrin, hydroxyethyl-beta-cyclodextrin, G2-alpha-cyclodextrin, G2-beta-cyclodextrin, gamma-cyclodextrin, and methyl-beta-cyclodextrin. A particularly preferred cyclodextrin is hydroxypropyl-beta-cyclodextrin (HPβCD). Combinations of cyclodextrins may also be employed for the purposes of the invention. Although not intending to be bound by any one theory, it is believed that hydrogen and/or van der Waals bonding forces are responsible for the bonding within the complex with the hydrogen bonding being present for the portion of the molecule exposed outside of the cyclodextrin ring. Theories on bonding types and strengths are documented in the literature and are known by the skilled artisan.

Although the use of cyclodextrins as solubilizing agents is generally known in the pharmaceutical arts, it is rarely, if ever, known what affect cyclodextrins will have on the bioavailability or other biological characteristics of the active ingredient(s) used with such one or more cyclodextrins. It was unexpectedly discovered that the addition of cyclodextrin to omeprazole API significantly increases both $C_{max}$ and, more importantly, AUC compared to an omeprazole formulation which does not include cyclodextrin. The solubility characteristics among compounds of the present invention will vary, but it is believed that such compounds have improved biological characteristics when formulated with cyclodextrins as taught herein.

Accordingly, the invention further encompasses compositions of matter comprising any of the active ingredients as defined hereinabove and at least one cyclodextrin. In one embodiment, the cyclodextrin and the active ingredient may be present in the form of a complex. In another embodiment, the cyclodextrin may be in free form.

In another aspect, the invention provides pharmaceutical formulations, preferably in unit dose form, comprising at least one active ingredient as defined hereinabove, at least one cyclodextrin, and at least one pharmaceutically acceptable carrier, diluent, or excipient that are defined herein, the selection of which are known to the skilled artisan. These pharmaceutical formulations can be present in any of the specific forms set forth herein or as known in the pharmaceutical arts, as appropriate. Particularly preferred are enteric coated oral dosage forms comprising at least one active ingredient and at least one cyclodextrin, preferably, hydroxypropyl-β-cyclodextrin. The above formulations may be prepared by using techniques known in the art including, without limitation, lyophilization, spray drying, and spray granulation. In the formulations, it is preferred that the active ingredient and the cyclodextrin be present in the form of an inclusion complex.

In one embodiment, hard and soft capsules comprising such at least one cyclodextrin and such active ingredient(s) are particularly preferred for the purposes of the invention. These formulations may be formed according to methods known to one skilled in the art using accepted ingredients (e.g., excipients, carriers, and/or diluents) such as, without limitation, those described hereinabove. As an example, at least one pharmaceutically acceptable, non-toxic solubilizing agent may be employed. Such readily available solubilizing agents are well known in the art and are typically represented by the family of compounds known as polyethylene glycols (PEG) having molecular weights from about 200 to about 8,000. When a liquid is desired for the final formulation or a liquid is to be used to fill soft capsules, preferably soft gelatin capsules, the preferred molecular weight range of PEG is from about 200 to about 600 with PEG 400 being especially preferred. When a semi-solid is preferred, especially for filling a hard capsule, preferably a hard gelatin capsule, a preferred PEG molecular weight is about 3350 while an especially preferred combination includes 3350 molecular weight PEG plus sufficient 400 molecular weight 6EG to improve capsule filling characteristics. Enterically coated hard gelatin capsules are particularly preferred with the higher molecular weight (e.g., 3350) PEG.

The formulation may comprise various amounts of cyclodextrin and active ingredient. Preferably, the complex comprises these components in a molar ratio of active ingredient to cyclodextrin ranging from about 1:4 to about 1:28, more preferably from about 1:4 to about 1:10.

The invention also provides methods of treating a subject (e.g., mammal, particularly humans) comprising administering to a subject in need of such treatment a therapeutically effective amount of at least one active ingredient, formulation thereof, or unit dose forms thereof, each as described herein. The active ingredient(s) may be used to treat a number of disorders. Generally, such active ingredients are useful for inhibiting gastric acid secretions and for preventing and treating gastric acid related diseases in mammals, particularly humans. These diseases include, but may not be limited to, duodenal ulcer, *H. pylori* infection, gastric ulcer, gastroesophageal reflux disease and symptoms associated therewith (e.g., heartbum), erosive esophagitis, pathological hypersecretary conditions (e.g., Zollinger-Ellison syndrome, endocrine adenomas and systematic mastocytosis), gastritis, duodenitis. The active ingredient(s) may also be used for the treatment of other gastrointestinal disorders where gastric acid inhibitory effect is desirable (e.g., in patients on NSAID therapy, in patients with Non Ulcer Dyspepsia). The active ingredient(s) may also be used in patients in intensive care situations, in patients with acute upper gastrointestinal bleeding, pre- and post-operatively to prevent acid aspiration of gastric acid and to prevent and treat stress ulceration. Moreover, the active ingredient(s) may be useful in the treatment of psoriasis as well as in the treatment of Heliocobacter infections and diseases related to those. The active ingredient(s) may also be used for the treatment of inflammatory conditions in mammals and particularly humans, particularly those involving lysozymal enzymes.

As used herein, the term "treatment", or a derivative thereof, contemplates partial or complete inhibition of the stated disease state such as, for example, duodenal ulcer, when an active ingredient of the present invention is administered prophylactically or following the onset of the disease state for which such active ingredient of the present invention is administered. For the purposes of the present invention, prophylaxis refers to administration of the active ingredient(s) to a mammal to protect the mammal from any of the disorders set forth herein, as well as others. Other examples of such conditions that may be treated include rheumatoid arthritis and gout.

Other disorders that may be prevented or treated in accordance with the invention including schizophrenia, symptoms of bradyphremia in Parkinson's Disease, elevated intraocular pressure in the eye of a patient, and microbial infections associated with gram-negative bacteria (especially microaerophilic bacteria), bacteria of the genus Campylbacter represented by *C. pylori*. The treatment of infectious diseases due to such bacteria in mammalian animals including without limitation humans, cattle, horse, dog, mouse, rat, the control and inhibition of environmental pollution, and disinfectant use may be achieved by virtue of the invention.

The active ingredient(s) disclosed herein possess worthwhile therapeutic properties as gastric acid secretion inhibitors as demonstrated by the following tests. To determine the gastric acid secretion inhibitory properties, experiments are performed on conscious dogs provided with gastric fistulas of conventional type and duodenal fistulas, the latter ones used for direct intraduodenal administration of the active ingredient(s). After 18 hours starvation and deprivation of water the dogs are given a subcutaneous infusion of pentagastrin (1–4 nmol/kg/h) lasting for 6 to 7 hours. Gastric juice is collected in consecutive 30 minute samples. An aliquot of each sample is titrated with 0.1N NaOH to pH 7 for titrable acid concentration using an automatic titrator and pH-meter. Acid output is calculated as mmol $H^+$/60 minutes. The active ingredient(s), suspended in 0.5 percent methyl cellulose, is given intraduodenally in doses from 4 to 20 nmol/kg when the secretory response to pentagastrin reaches a steady level. This embodiment may also be used for prophylaxis by administration of the active ingredient prior to pentagastrin.

The typical active daily dose of the active ingredients(s) will depend on various actors such as, for example, the individual requirement of each patient, the route of administration, and the disease. An attending physician may adjust the dosage rate based on these and other criteria it he or she so desires. As an example, a suitable oral dosage form may encompass from about 5 to about 360 mg total daily dose, typically administered in one single dose or equally divided doses. A more preferred range is from about 8 mg to about 60 mg total daily dose, and a most preferred range is from about 10 mg to about 40 mg total daily dose. Additionally, the active ingredient(s) may be administered in a solution, and, as an example, the daily doses set forth above may be employed. In one embodiment, the active ingredient(s) may be added in appropriate amounts to a solution such that the solution comprises, for example, from about 0.1 mg/mL to about 10 mg/mL of the active ingredient (s). It should be appreciated that daily doses other than those described above may be administered to a subject, as appreciated by an attending physician. Preferred active ingredients are those as set forth herein, while especially preferred ingredients include; for example, 6-methoxy-2-[[(4methoxy-3,5-dimethyl-2-pyridinyl)methyl]sulfinyl]-1H-benzimidazole, in pure form, 6-methoxy-2-[[(4-methoxy-3,5-dimethyl-2-pyridinyl)methyl]sulfinyl]-1H-benzimidazole essentially free of 5-methoxy-2-[[(4methoxy-3,5-dimethyl-2-pyridinyl)methyl]sulfinyl]-1H-benzimidazole, a composition comprising 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl)methyl]sulfinyl]-1H-benzimidazole wherein said 6-methoxy-2-[[(4-methoxy-3,5-dimethyl-2-pyridinyl)methyl]sulfinyl]-1H-benzimidazole comprises from about 96% to about 100% (w/w) of said composition and a composition comprising 6-methoxy-2-[[(4-methoxy-3,5dimethyl-2-pyridinyl)methyl]sulfinyl]-1H-benzimidazole and 5-methoxy-2-[[(4-methoxy-3,5dimethyl-2-pyridinyl)methyl]sulfinyl]-1H-benzimidazole is present in an amount greater than about 9%, preferably 15%, and most preferably 18% (w/w) of said composition. For the method of improving the bioavailability of one or more active ingredients set forth below, a composition comprising 6-methoxy-2-[[(4-methoxy-3,5-dimethyl-2-pyridinyl) methyl]sulfinyl]-1H-benzimidazole and 5-methoxy-2-[[(4-methoxy-3,5-dimethyl-2-pyridinyl)methyl]sulfinyl]-1H-benzimidazole is also preferred. Also preferred are unit dosage forms as taught herein, particularly in the amount of total active ingredient of about 8 mg to about 10 mg, about 16 mg to about 20 mg, and about 32 mg to about 40 mg per dosage unit.

In another aspect, the present invention provides a method of improving the bioavailability of one or more active ingredient of the present invention in a subject (e.g., mammal, particularly humans) comprising administering to a subject in need of such treatment a therapeutically effective amount of at least one active ingredient, composition thereof, or formulation thereof as described above, and at least one cyclodextrin. This method may be carried out in accordance with any of the techniques set forth herein, including employing, without limitation, any of the recited dosage forms, particularly in the unit dosages set forth herein. For the purposes of the invention, the term "bioavailability" is defined as the total amount of active ingredient systematically available over time. Bioavailability may be determined by measuring total systemic active ingredient concentrations over time after administration of such active ingredient(s) of the present invention either singularly or in comparison with bioavailability after administration of a conventional omeprazole formulation (e.g., Prilosec®). As an example, improved bioavailability may be defined as the Area Under the Curve (AUC). AUC is the integrated measure of systemic active ingredient concentrations over time in units of mass-time/volume. Following the administration of an active ingredient dose, the AUC from the time of dosing to the time when no active ingredient remains in the body, is a measure of the exposure of the subject to the active ingredient or, in some cases, the active molecule which is a metabolite of an active ingredient In a preferred embodiment, this method typically allows for an increase in AUC of about 20 percent or greater relative to a conventional omeprazole formulation. In another embodiment, the method allows for an increase in $C_{max}$ of a subject of about 25 percent or greater relative to a conventional omeprazole formulation.

The following examples are intended to illustrate the invention, and are not to be construed as limiting the scope of the invention. For the purposes of the examples, the phrase "(5)6-methoxy 2-[[(4-methoxy-3,5-dimethyl-2-pyridinyl)-methyl]sulfinyl]-1H-benzimidazole" refers to a combination of, preferably a co-crystallized mixture, (with or without an amount of amorphous compounds), of 5-methoxy-2-[[(4-methoxy-3-dimethyl-2-pyridinyl)-methyl]sulfinyl]-1H-benzimidazole and 6-methoxy-2-[[(4-methoxy-3,5-dimethyl-2-pyridinyl)-methyl]sulfinyl]-1H-benzimidazole, each as determined and referenced herein.

EXAMPLE 1

Preparation of Essentially Pure 6-Methoxy-2-[[(4methoxy-3,5-dimethyl2-pyridinyl)methyl]sulfinyl]-1H-benzimidazole Approximately 850 mL of methanol was placed in a 1 liter glass bottle with a screw cap. The solution was saturated by dissolving approximately 10.5 g of (5)6-methoxy-2[[(4-methoxy-3,5-dimethyl-2-pyridinyl)-methyl]sulfinyl]-1H-benzimidazole, and the resulting solution was stirred. Once the solution was saturated, an additional 17 g of (5)6-methoxy-2-[[(4-methoxy-3,5-dimethyl-2-pyridinyl)-methyl]sulfinyl]-1H-benzimidazole was added to the saturated solution to create a suspension. The cap was sealed and the saturated suspension was allowed to stir and equilibrate for about four days.

After four days, the suspension was filtered through a paper filter and then washed with a small amount of methanol. The supernatant was returned to the 1 liter glass bottle and an additional 10 g of (5)6-methoxy-2[[(4methoxy-3,5-dimethyl-2-pyridinyl)-methyl]sulfinyl]-1H-benzimidazole was added to the saturated solution. The procedure was repeated to create an additional sample. All samples are shown to be essentially pure 6-methoxy-2-[[(4-methoxy-3,5-dimethyl-2-pyridinyl)-methyl]sulfinyl]-1H-benzimidazole by Raman spectroscopy. This procedure has also been successfully carried out using ethanol.

EXAMPLE 1a

Preparation of Pure 6-Methoxy-2[[(4methoxy-3,5-dimethyl-2-pyridinyl)methyl]sulfinyl]-1H-benzimidazole To a 1000 mL glass bottle having a screw cap having about 300 mL of methanol was added 1.93 g of sodium hydroxide pellets. The solution was stirred until such pellets dissolved, and omeprazole API was added until a heavy suspension was formed. The solution was capped and allowed to sit, at ambient temperature, for four days, then filtered using vacuum filtration and a paper filter. The resulting solid was washed with three, 50 mL portions of methanol, then placed in a vacuum oven to dry at ambient temperature. The title compound was removed after drying for 24 hours, and the purity confirmed by FT-Raman spectroscopy.

EXAMPLE 2

Preparation of Essentially Free 6-Methoxy-2-[[(4-methoxy-3,5dimethyl-2-pyridinyl)-methyl]sulfinyl]-1H-benzimidazole To a 50 mL beaker was added about 1 g of (5)6-methoxy-2-[[(4-methoxy-3,5-dimethyl-2-pyridinyl)-methyl]sulfinyl]-1H-benzimidazole to 30 mL of dimethylformamide (DMF). Additional (5)6-methoxy-2[[(4methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 µm Poly (tetrafluoroethylene) (PTFE). or Nylon filter. The resulting saturated solution was placed in a shallow petri dish, covered and stored under refrigerated conditions (approximately 5° C.) with a humidity range of about 0 to 50 percent until crystals formed (between 4–6 days). The identity of the title compound is confirmed by single crystal x-ray diffraction and Raman spectroscopy, and shown to contain between about 96 and 98 percent (w/w) of the 6-methoxy-2[[(4-methoxy-3,5dimethyl-2pyridinyl)methyl]sulfinyl]-1H-benzimidazole and between about 2 and 4 percent (w/w) of 5-methoxy-2-[[(4-methoxy-3,5-dimethyl-2-pyridinyl)-methyl]sulfinyl]-1H-benzimidazole.

EXAMPLE 3

Preparation of (5)6-Methoxy-2-[[(4methoxy-5-dimethyl-2pyridinyl)-methyl]sulfinyl]-1H-benzimidazole The procedure set forth in Example 2 is repeated except that ethanol is employed as a solvent in place of DMF and the resulting structure is shown by various X-ray crystal diffraction and/or Raman spectroscopy to contain between about 82 and 85 percent (w/w) of 6-methoxy-2[[(4methoxy-3,5-dimethyl-2-pyridinyl)-methyl]sulfinyl]-1H-benzimidazole and between about 15 and 18 percent (w/w) of 5-methoxy 2[[(4-methoxy-3,5-dimethyl-2-pyridinyl)-methyl]sulfinyl]1H-benzimidazole.

EXAMPLE 4

Preparation of 5(6)-Methoxy-2-[[(4-methoxy-3,5dimethyl-2-pyridinyl)-methyl]sulfinyl]-1H-benzimidazole Isomers To a 50 mL beaker was added about 1 g of 5(6)-methoxy-2-[[(4-methoxy-3,5-dimethyl-2-pyridinyl)-methyl]sulfinyl]-1H-benzimidazole to 30 mL of DMF. Additional 5(6)-methoxy-2-[[(4-methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 µm PTFE or Nylon filter. The resulting saturated solution was placed in a shallow petri dish, covered, and stored at ambient temperature and a humidity range of about 0 to 50 percent until crystals formed (between 1–2 days). The identity of the title compound is confirmed by single crystal x-ray diffraction and/or Raman spectroscopy. The resulting structure was determined to contain about 93 percent (w/w) of the 6-methoxy-2-[[(4-methoxy-3,5-dimethyl-2pyridinyl)-methyl]sulfinyl]-1H-benzimidazole and about 7 percent (w/w) of the 5-methoxy-2-[[(4-methoxy-3,5-dimethyl-2-pyridinyl)-methyl]sulfinyl]-1H-benzimidazole.

EXAMPLE 5

Preparation of 5(6)-Methoxy-2-[[(4-methoxy-3,5-dimethyl-2-pyridinyl)-methyl]sulfinyl]-1H-benzimidazole Isomers To a 50 mL beaker was added about 1 g of 5(6)-methoxy-2[[(4-methoxy-3,5-dimethyl-2-pyridinyl)-methyl]sulfinyl]-1H-benzimidazole to 30 mL of methylene chloride. Additional 5(6)-methoxy-2-[[(4-methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 µm PTFE or Nylon filter. The resulting saturated solution was placed in a beaker, covered, and stored under refrigerated conditions (approximately 5° C.) until crystals formed (between 1–2 days). The identity of the title compound is confirmed by single crystal x-ray diffraction and/or Raman spectroscopy. The resulting material was determined to contain between about 84 and 88 percent (w/w) of the 6-methoxy-2-[[(4methoxy-3,5-dimethyl-2-pyridinyl)-methyl]sulfinyl]-1H-benzimidazole and between about 12 and 16 percent (w/w) of the 5-methoxy-2-[[(4-methoxy-3,5-dimethyl-2-pyridinyl)-methyl]sulfinyl]1H-benzimidazole.

EXAMPLE 6

Preparation of 6(6)-Methoxy-2[[(4-methoxy-3,5-dimethyl-2-pyridinyl)-methyl]sulfinyl]-1-benzimidazole Isomers To a 50 mL beaker was added about 1 g of 5(6)-methoxy-2-[[(4methoxy-3,5-dimethyl-2-pyridinyl)-methyl]sulfinyl]-1H-benzimidazole to 25 mL of acetone. Additonal 5(6)-methoxy-2[[(4-methoxy-3,5dimethyl-2-pyridinyl)-methyl]sulfinyl]-1H-benzimidazole was added to the resulting solution until a suspension of the material was formed. The solution was stirred for approximately 5 minutes, and then filtered through a 0.45 µm PTFE or Nylon filter. The resulting saturated solution was placed in a 50 mL beaker, covered, and stored at ambient temperature and a humidity range of about 0 to 50 percent until crystals formed (between 1–2 days). The identity of the title compound is confirmed by single crystal x-ray diffraction and/or Raman spectroscopy. The resulting material was determined to contain about 86 percent (w/w) of the 6-methoxy-2-[[(4-methoxy-3,5-dimethyl-2-pyridinyl)-methyl]sulfinyl]-1H-benzimidazole and about 14 percent (w/w) of the 5-methoxy-2[[(4methoxy-3,5-dimethyl-2-pyridinyl)-methyl]sulfinyl]-1H-benzimidazole.

EXAMPLE 7

Preparation of 5(6)-Methoxy-2-[[(4-methoxy-3,5-dimethyl-2pyridinyl)-methyl]sulfinyl]-1H-benzimidazole Isomers The procedure set forth in Example 6 is repeated except that an ACN/water mixture was used as a solvent in place of acetone. A similar composition of 6-methoxy-2[[(4methoxy-3,5-dimethyl-2-pyridinyl)-methyl]sulfinyl]-1H-benzimidazole and 5-methoxy-2-[[(4-methoxy-3,5-dimethyl-2-pyridinyl)-methyl]sulfinyl]-1H-benzimidazole resulted.

EXAMPLE 8

Preparation of 5(6)-Methoxy-2-[[(4methoxy-3,5-dimethyl-2pyridinyl)-methyl]sulfinyl]-1H-benzimidazole Isomers The procedure set forth in Example 6 is repeated except that ACN was used as a solvent in place of acetone. A similar composition of 6-methoxy-2-[[(4-methoxy-3,5-dimethyl-2-pyridinyl)-methyl]sulfinyl]1H-benzimidazole and 5-methoxy-2-[[(4methoxy-3,5dimethyl-2-pyridinyl)-methyl]sulfinyl]-1H-benzimidazole resulted.

EXAMPLE 9

Preparation of (5)6-Methoxy-2-[[(4-methoxy-3,5-dimethyl-2-pyridinyl)-methyl]sulfinyl]-1H-benzimidazole Isomers To a 400 mL beaker was added about 5 g of (5)6-methoxy-2-[[(4-methoxy-3,5-dimethyl-2pyridinyl)-methyl]sulfinyl]-1H-benzimidazole to 200 mL of ethanol. 1.0 mL of ammonium hydroxide was added to this solution and additional 5(6)-methoxy-2-[[(4-methoxy-3,5-dimethyl-2-pyridinyl)-methyl]sulfinyl]-1H-benzimidazole was added to the resulting solution until a suspension of the material was formed. The solution was stirred for about 10 minutes, then filtered through a paper filter. The resulting saturated solution was placed in two separate drying vessels, and stored in a fume hood at ambient temperature until crystals formed (between 1–12 hours). The identity of the title compound was confirmed by single crystal x-ray diffraction. The resulting structure was determined to contain about 82 percent (w/w) of the 6-methoxy-2-[[(4methoxy-3,5-dimethyl-2-pyridinyl-methyl]sulfinyl]-1H-benzimidazole and about 18 percent (w/w) of the 5-methoxy-2-[[(4-methoxy-3,5-dimethyl-2-pyridinyl)-methyl]sulfinyl]-1H-benzimidazole.

EXAMPLE 10

Preparation of (5)6-Methoxy-2-[[(4-methoxy-3,6-dimethyl-2-pyridinyl)-methyl]sulfinyl]-1H-benzimidazole (5)6-methoxy-2[[(4methoxy-3,5-dimethyl-2-pyridinyl)-methyl]sulfinyl]1H-benzimidazole (16.2 g; 0.0492 mol)) is reacted with m-chlorobenzoic acid (13.6 g; 0.0537 mol) with $CH_2Cl_2$ acting as a solvent at a pH of 8.6. The pH is maintained by the presence of $KHCO_3$ (5.6 g; 0.056 mol) acting as a buffer. The temperature is maintained at about 0° C. during the addition. Diluted NaOH is added to a pH above 12 and the $CH_2Cl_2$ phase is separated off. Dimethylformamide (4.7 g) is charged to the water phase and the pH is kept above 9, whereupon crystals a mixture of (5)6-methoxy-2-[[(4-methoxy-3,5-dimethyl-2-pyridinyl)methyl]sulfinyl]-1H-benzimidazole are formed. The crystals are filtered off and are washed with water and methanol at a temperature of about 0° C. The washed crystals are then dried under vacuum and are found to predominantly contain 6-methoxy-2-[[(4-methoxy-3,5dimethyl-2-pyridinyl)methyl]sulfinyl] 1H-benzimidazole.

EXAMPLE 11

Preparation of the Sodium Salt of 6-Methoxy-2-[[(4methoxy-3,5-dimethyl-2-pyridinyl)methyl]sulfinyl]-1H-benzimidazole To a stirring suspension of 10 g (29 mmol) of (5)6methoxy-2-[[(4-methoxy-3,5-dimethyl-2-pyridinyl)

methyl]sulfinyl]-1H-benzimidazole in 200 mL of methyl ethyl ketone (MEK) in a 1 L flask was added at ambient temperature 6 mL of a 5 M aqueous sodium hydroxide solution. To that mixture was added 200 mL of toluene. After approximately 7 minutes, the mixture became a clear solution. Approximately 2 minutes after that, the mixture became turbid again. This mixture was allowed to stir at ambient temperature overnight. The following morning, several crystals of 6-methoxy-2-[[(4-methoxy-3,5-dimethyl-2-pyridinyl)methyl]sulfinyl]-1H-benzimidazole sodium salt were added to act as seed crystals. Within a few minutes the product began to precipitate. After approximately 1 hour, the product was isolated by vacuum filtration through filter paper on a ceramic Buchner funnel and rinsed with 25 mL of diethyl ether. The resulting solids were allowed to air-dry for 24 hours.

EXAMPLE 12

Preparation of the Sodium Salt of 6-Methoxy-2-[[(4-methoxy-3,5-dimethyl-2-pyridinyl)methyl]sulfinyl]-1H-benzimidazole To a flask containing 20 mL of methanol was slowly added with stirring 580 mg (14.48 mmol) of 60% sodium hydride dispersed in mineral oil. The resulting cloudy mixture was vacuum filtered through a glass-fiber filter paper to yield a clear solution. To this clear solution was added with stirring 5 g (14.48 mmol) of 6-methoxy-2-[[(4-methoxy-3,5-dimethyl-2-pyridinyl)methyl]sulfinyl]-1H-benzimidazole. After approximately 5 minutes of stirring the solution became clear. The stirring was stopped, the flask was covered and set aside. After approximately 5 minutes, crystals began to form. The mixture was placed in a 5° C. refrigerator overnight The next day, the solids were isolated by vacuum filtration to give approximately 5 g of the desired product as a white, crystalline powder.

EXAMPLE 13

Preparation of the Sodium Salt of 6-Methoxy-2-[[(4-methoxy-3,5-dimethyl-2-pyridinyl)methyl]sulfinyl]-1H-benzimidazole To a stirring solution of 5 g (14.48 mmol) of (5)6methoxy-2-[[(4-methoxy-3,5-dimethyl-2-pyridinyl)methyl]sulfinyl]-1H-benzimidazole in 50 mL of dimethyl formamide (DMF) in a 00 mL beaker was slowly added at ambient temperature 580 mg (14.48 mmol) of 60% sodium hydride dispersed in mineral oil. Once all the sodium hydride was added, the mixture was allowed to str for an additional 10 minutes. The solution was vacuum filtered through filter paper on a ceramic Buchner funnel. A 20 mL portion of the resulting solution was placed in a 250 mL round-bottom flask, diluted with 50 mL of toluene and concentrated under reduced pressure at 20° C. (2 times), followed by 50 mL of tetrahydrofuran (1 time). The resulting solids were dried 18 hours at ambient temperature in vacuo to yield the desired product as an off-white, crystalline powder. The powder was recrystallized from methanol by placing a filtered, saturated solution into the 5° C. refrigerator for several days, until crystals were present.

EXAMPLE 14

Preparation of the Sodium Salt of 6-Methoxy-2-[[(4-methoxy-3,5-dimethyl-2-pyridinyl)methyl]sulfinyl]-1H-benzimidazole To a stirring suspension of 5 g (14.48 mmol) of (5)6-methoxy-2-[[(4-methoxy-3,5-dimethyl-2-pyridinyl)methyl sulfinyl]-1H-benzimidazole in 50 mL of tetrahydrofuran (THF) in a 100 mL beaker was slowly added at ambient temperature 580 mg (14.48 mmol) of 60% sodium hydride dispersed in mineral oil. Once all the sodium hydride was added, the mixture was allowed to stir for an additional 20 minutes. The solids were isolated by vacuum filtration through filter paper on a ceramic Buchner funnel and rinsed with a small amount of THF. The solids were dried 18 hours at ambient temperature in vacuo to yield 4.8 g (90%) of the desired product as an off-white, crystalline powder. The powder was recrystallized from 1:1 methanol:ethyl acetate by placing a filtered, saturated solution into the 5° C. refrigerator for several days, until crystals were present

EXAMPLE 15

Preparation of the Sodium Salt of (−)(5)6-Methoxy-2-[[(4-methoxy-3,5-dimethyl-2-pyridinyl)methyl]sulfinyl]-1H-benzimidazole To a stirring solution of 1.5 g (4.33 mmol)of (−)5)6-methoxy-2-[[(4-methoxy-3,5-dimethyl-2-pyridinyl)methyl]sulfinyl]-1H-benzimidazole in 15 mL of tetrahydrofuran (THF) in a 50 mL beaker was slowly added at ambient temperature 173 mg of 60% sodium hydride dispersed in mineral oil. Once, all the sodium hydride was added, the mixture was allowed to stir for 45 minutes at ambient temperature. An additional 15 mL of THF was added to the mixture and was allowed to stir for an additional 20 minutes. The precipitated solids were isolated by vacuum filtration through filter paper on a ceramic Buchner funnel, rinsed with 40 mL of the THF and dried 18 hours at ambient temperature in vacuo to yield 1.3 g (81 percent) of the desired product as an off-white powder.

EXAMPLE 16

Preparation of (+)-(5)6-Methoxy-2-[[(4-methoxy-3,5-dimethyl-2-pyridinyl)methyl]sulfinyl]-1H-benzimidazole Sodium Salt To a stirring suspension of 650 mg (1.89 mmol) of (+)5)6-methoxy-2-[[(4-methoxy-3,5-dimethyl-2-pyridinyl)methyl]sulfinyl]-1H-benzimidazole in 6.5 mL of methyl ethyl ketone (MEK) in a 50 mL flask was added, at ambient temperature 0.39 mL of a 5M aqueous sodium hydroxide solution. To that mixture was added 13 mL of toluene. The resulting mixture was turbid, so an additional 6.5 mL of MEK was added and the mixture became a clear, yellow solution. This mixture was allowed to stir at ambient temperature overnight. The following morning, several crystals of 6-methoxy-2-[[(4-methoxy-3,5-dimethyl-2-pyridinyl)methyl]sulfinyl]-1H-benzimidazole sodium salt were added to act as seed crystals, but no product crystals formed. A stream of dry nitrogen gas was blown over the mixture to begin removing the solvent After approximately 10 minutes, the product precipitated. The solids were isolated by vacuum filtration and washed with a small amount of diethyl ether. The solids were then placed into a vacuum desiccator to remove the last traces of ether, to yield approximately 500 mg of the desired product as an off-white powder.

EXAMPLE 17

Preparation of (5)6-Methoxy-2-[[methoxy-3,5-dimethyl-2-pyridinyl)methyl]sulfinyl]-1H-benzimidazole Magnesium Salt Tetrahydrate 1.65 g of 6-methoxy-2-[[(4-methoxy-3,5dimethyl-2-pyridinyl)methyl]sulfinyl]-1H-benzimidazole sodium salt was dissolved in 30 mL of water. To the stirring solution was added 0.47 g of magnesium chloride dissolved in 20 mL of water. Immediately upon the addition of the magnesium chloride solution a white powder precipitated. The suspension was allowed to stir for 5 minutes, and then the product was isolated by vacuum filtration. The solids were then placed into a vacuum desiccator overnight to give the desired product as a white powder. A small portion of the powder was dissolved in methanol at about 75 mg/mL, filtered and diluted with a equal volume of water. This solution was partially covered and set aside to slowly evaporate. After approximately 5 days, crystals were isolated, analyzed by single crystal x-ray diffraction and shown to be the desired product.

EXAMPLE 18

Preparation of a Mixture of the (−) Enantiomers of (5)6-Methoxy-2-[[(4-methoxy-3,5-dimethyl-2-pyridinyl) methyl]sulfinyl]-1H-benzimidazole (5)6-methoxy-2-[[(4methoxy-3,5dimethyl-2-pyridinyl) methyl]thio]-1H-benzimidazole (4.0 g, 12.1 mmol) is suspended in toluene (12 mL). (−) Diethyl D-tartrate (0.17 mL, 1.0 mmol) and titanium(IV) isopropoxide (0.15 mL, 0.50 mmol) are added with stirring at 50° C. The mixture is stirred at 50° C. for 50 minutes and then N,N-diisopropylethylamine(0.085 mL, 0.50 mmol) is added at ca. 30° C. Then, cumene hydroperoxide (83%, 2.1 mL, 11.9 mmol) is added and the mixture is stirred for 15 minutes at 30° C. The resulting mixture contains the (−) enantiomers of (5)6 methoxy-2-[[(4methoxy-3,5-dimethyl-2-pyridinyl) methyl]sulfinyl]-1H-benzimidazole.

EXAMPLE 19

Preparation of a Mixture of the (+) Enantiomers of (5)6-Methoxy-2[[(4-methoxy-3,5dimethyl-2-pyridinyl) methyl]sulfinyl]-1H-benzimidazole (+) Diethyl L-tartrate (1.71 mL, 10 mmol) and titanium (IV) isopropoxide (1.5 ml, 5 mmol) are dissolved in methylene chloride (50 mL). Water (90 μl. 5 mmol) is added with stirring and the resultant mixture is heated to reflux for one hour. The mixture is cooled to room temperature. Thereafter, (5)6-methoxy-2-[[(4-methoxy-3,5-dimethyl-2-pyridinyl) methyl]thio]-1H-benzimidazole (1.65 g 5 mmol) and cumene hydroperoxide (80%, 1.5 g, 5.5 mmol) are added at room temperature. The solution is stirred at room temperature for 90 minutes. The final product provides (5)6-methoxy-2-[[(4-methoxy-3,5-dimethyl-2-pyridinyl)methyl] sulfinyl]-1H-benzimidazoles.

EXAMPLE 20

Preparation of (−)-(5)6-Methoxy-2-[[(4-methoxy-3, 5-dimethyl-2-pyridinyl)methyl]sulfinyl]-1H-benzimidazole Magnesium Salt To a nitrogen-purged flask containing 50 mL of methanol was added with stirring 0.11 g (4.5 mmol) of magnesium metal, followed by a catalytic amount (~0.55 mL) of methylene chloride. This mixture was heated to 40° C. for 5 hours, then removed from the heat an allowed to cool to ambient temperature. To the cloudy, stirring solution was added approximately 2 g of (−)-5(6)-methoxy-2-[[(4methoxy-3,5-dimethyl-2-pyridinyl)methyl]sulfinyl]-1H-benzimidazole. The flask was purged well with nitrogen, sealed and allowed to stir at ambient temperature overnight Approximately 0.1 mL of water was then added to the reaction mixture and allowed to stir for 30 minutes to precipitate inorganic magnesium salts. The mixture was then vacuum filtered, and the filtrate reduced to approximately 20% of the original volume under reduced pressure. To that resulting solution was added with stirring 100 mL of acetone. After approximately 5 minutes of stirring, a precipitate began to form. The mixture was allowed to stir for an additional 30 minutes. The solids were isolated by vacuum filtration and washed with some fresh acetone. The solids were allowed to air dry to yield 640 mg of the desired product.

EXAMPLE 21–29

Preparation of 6-Methoxy-2-[[(4-methoxy-3,5-dimethyl-2-pyridinyl)methyl]sulfinyl]-1H-benzimidazole from Mixtures of 5-and 6-methoxy Benzimidazoles Compositions which are formed in Examples 3–10 are subjected to the procedure set forth in Example 1. Pure 6-methoxy compounds were thereafter obtained from this procedure.

EXAMPLE 30–33

Preparation of 6-Methoxy-2[[(4-methoxy-3,5-dimethyl-2-pyridinyl)methyl]sulfinyl]-1H-benzimidazole from Mixtures of 5- and 6-methoxy Benzimidazoles Compositions which are formed in Examples 15–17 and 20 are subjected to the procedure set forth in Example 1. Pure salts of the 6-methoxy compounds were thereafter obtained from this procedure.

EXAMPLE 34

Determination of Percentage of Co-crystallized 5- and 6-Methoxy-2-[[(4-methoxy-3,5dimethyl-2-pyridinyl)-methyl]sulfinyl]-1H-Benzimidazole Isomers Typically, a single crystal X-ray diffraction was used to determine the percentage of 5- and 6-methoxy-2 [[(4methoxy-3,5-dimethyl-2-pyridinyl) methyl]sulfinyl]-1H-benzimidazole isomers in an API. Without being bound to theory, it is believed that a crystalline material diffracts X-rays due to the constructive and destructive interference of the scatter of X-rays from the atoms of the molecule within the crystal lattice. The intensity and positions of the diffraction spots produced by the crystal is capable of generating structural information about the locations of the atoms in the molecule of a crystal.

In this instance, a single crystal of the material to be examined is mounted at the end of a glass fiber. The crystal is aligned in the diffractometer in a specific orientation. The diffraction spots are measured, then the crystal is rotated to the next position. The above sequence is then repeated until thousands of individual diffraction spots are measured and recorded. The diffraction spots are then analyzed and the data phased to generate an electron density map from which a molecular structure of the molecule is uniquely determined. The X-ray diffraction data is generated using either a Nonius CAD4 diffractometer or a Nonius Kappa CCD diffractometer made commercially available by Nonius Corporation of Delft, Netherlands. The diffraction data generated for the various batches of omeprazole API tested shows the molecular structure of the drug present. It was determined from the data that the crystal lattice contained various degrees of disorder of the 6- and 5-methoxy isomers within the API. The two isomers were found to co-crystallize within a single crystal lattice. This co-crystallization within the single lattice is believed to cause a distortion of the six independent unit cell parameters in relation to the amount of each isomer present. The exact amount of 5-methoxy isomer present was determined by a least-squares minimization of the data. A linear regression analysis of the cell constants to the percentage of the 5-methoxy isomer present demonstrated good correlation coefficients.

In this example, the compounds were found to contain predominantly two diastereomers, namely the $S_{xa}$—$R_{4q}$ and $S_{xb}$—$R_{4z}$ derivatives. Such proposed behavior was not expected, since the manner in which the compounds were synthesized is believed to be non-discriminatory towards selection of the $R_{4q}$ or $R_4$. chiral plane with the corresponding $S_{xa}$ or $R_{4z}$ chiral center. Although not intending to be bound by theory, structural analysis reveals that the 5- and 6-methoxy isomer is crystallize through a center of inversion and are linked by hydrogen bonding from the amine hydrogens to the sulfoxide oxygens. The methoxy methyls are believed to be directed towards the center of the bridged complex. Again not being bound by theory, examination of the contact, distances in the region where the other methoxy methyl may reside reveals that there may not be adequate space within the lattice for the other diastereomers ($S_{xa}$—$R_{4z}$ and $S_{xb}$—$R_{4q}$) to co-exist. The oxygen atom of the methoxy is observed to sit only about 3.6 Å from 4 other non-hydrogen atoms and 3.2 Å from 2 hydrogen atoms of an adjoining molecule of omeprazole. Normal Van DerWaals contact distances are typically about 3.7 Å for non-hydrogen atoms.

EXAMPLE 35

Preparation of (5)6-Methoxy-2-[[(4-methoxy-3,5-dimethyl-2-pyridinyl)-methyl]sulfinyl]-1H-benzimidazole To a 50 mL beaker was added about 1 g of (5)6-methoxy-2-[[(4-methoxy-3,5-dimethyl-2-pyridinyl)-methyl]sulfinyl]-1H-benzimidazole to 30 mL of dimethylformamide (DMF). Additional (5)6-methoxy-2-[[(4-methoxy-3,5-dimethyl-2pyridinyl)-methyl]sulfinyl]-1H-benzimidazole was added to the resulting solution until a suspension of the material was formed. The solution was stirred for approximately 10 minutes, and then filtered through a 0.45 μm Poly (tetrafluoroethylene) (PTFE) or Nylon filter. The resulting saturated solution was placed in a shallow petri dish, covered and stored under refrigerated conditions (approximately 5° C.) and a humidity range of approximately 50 to 90 percent until crystals formed (between 4–7 days). The identity of the title compound is confirmed by single crystal x-ray diffraction and/or Raman spectroscopy. The resulting material was shown to contain between about 85 and 89 percent (w/w) of the 6-methoxy-2-[[(4-methoxy-3,5-dimethyl-2pyridinyl)methyl]sulfinyl]-1H-benzimidazole and between about 11 and 15 percent (w/w) of 5-methoxy-2-[[(4methoxy-3,5-dimethyl-2-pyridinyl)-methyl]sulfinyl]-1H-benzimidazole.

EXAMPLE 36

Preparation of (5)6-Methoxy-2-[[(4methoxy-3,5-dimethyl-2-pyridinyl)-methyl]sulfinyl]-1H-benzimidazole To a 50 mL beaker was added about 1 g of (5)6-methoxy-2-[[(4methoxy-3,5-dimethyl-2-pyridinyl)-methyl]sulfinyl]-1H-benzimidazole to 30 mL of acetone. Additional (5)6-methoxy-2-[[(4methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under refrigerated conditions (approximately 5° C.) and a humidity range of approximately 50 to 90 percent until crystals formed (between 1–2 days). The identity of the title compound is confirmed by single crystal x-ray diffraction and/or Raman spectroscopy. The resulting material was shown to contain between about 79 and 82 percent (w/w) of the 6-methoxy-2-[[(4methoxy-3,5-dimethyl-2-pyridinyl)-methyl]sulfinyl]-1H-benzimidazole and between about 18 and 21 percent (w/w) of 5-methoxy-2-[[(4methoxy-3,5-dimethyl-2-pyridinyl)-methyl]sulfinyl]-1H-benzimidazole.

EXAMPLE 37

Preparation of (5)6-Methoxy-2-[[(4methoxy-3,5-dimethyl-2-pyridinyl)-methyl]sulfinyl]-1H-benzimidazole To a 50 mL beaker was added about 1 g of (5)6-methoxy-2-[[(4-methoxy-3,5-dimethyl-2-pyridinyl)-methyl]sulfinyl]-1H-benzimidazole to 30 mL of methylene chloride. Additional (5)6-methoxy-2-[[(4methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 μm Poly (tetrafluoroethylene) (PTFE) or Nylon filter. The resulting saturated solution was placed in a shallow peti dish, covered and stored under refrigerated conditions (approximately 5° C.) and a humidity range of approximately 50 to 90 percent until crystals formed (between 1–2 days). The identity of the title compound is confirmed by single crystal x-ray diffraction and/or Raman spectroscopy. The resulting material was shown to contain between about 81 and 86 percent (w/w) of the 6-methoxy-2-[[(4methoxy-3,5-dimethyl-2-pyridinyl)-methyl]sulfinyl]-1H-benzimidazole and between about 14 and 19 percent (w/w) of 5-methoxy-2-[[(4-methoxy-3,5-dimethyl-2-pyridinyl)-methyl]sulfinyl]-1H-benzimidazole.

EXAMPLE 38

Preparation of (5)6-Methoxy-2-[[(4methoxy-3,5-dimethyl-2-pyridinyl)-methyl]sulfinyl]-1H-benzimidazole To a 50 mL beaker was added about 1 g of (5)6-methoxy-2[[(4-methoxy-3,5-dimethyl-2-pyridinyl)-methyl]sulfinyl]-1H-benzimidazole to 30 mL of acetonitrile. Additional (5)6-methoxy-2-[[(4methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under refrigerated conditions (approximately 5° C.) and a humidity range of approximately 50 to 90 percent until crystals formed (between 1–2 days). The identity of the title compound is confirmed by single crystal x-ray diffraction and/or Raman spectroscopy. The resulting material was shown to contain between about 88 and 92 percent (w/w) of the 6-methoxy-2-[[(4methoxy-3,5-dimethyl-2-pyridinyl)methyl]sulfinyl]-

1H-Benzimidazole and between about 8 and 12 percent (w/w) of 5-methoxy-2-[[(4-methoxy-3,5-dimethyl-2-pyridinyl)-methyl]sulfinyl]-1H-benzimidazole.

EXAMPLE 39

Preparation of (6)6-Methoxy-2-[[(4-methoxy-3,5-dimethyl-2-pyridinyl)-methyl]sulfinyl]-1H-benzimidazole To a 50 mL beaker was added about 19 of (5)6-methoxy-2[[(4-methoxy-3,5-dimethyl-2-pyridinyl)-methyl]sulfinyl]-1H-benzimidazole to 30 mL of dimethylformamide (DMF) containing 1 mL of ammonuim hydroxide. Additional (5)6-methoxy-2-[[(4-methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under refrigerated conditions (approximately 5° C. and a humidity range of approximately 50 to 90 percent until crystals formed (between 1–3 days). The identity of the title compound is confirmed by single crystal x-ray diffraction and/or Raman spectroscopy. The resulting material was shown to contain between about 84 and 86 percent (w/w) of the 6-methoxy-2-[[(4methoxy-3,5-dimethyl-2-pyridinyl)-methyl]sulfinyl]-1H-benzimidazole and between about 14 and 16 percent (w/w) of 5-methoxy-2-[[(4methoxy-3,5-dimethyl-2-pyridinyl)-methyl]sulfinyl]-1H-benzimidazole.

EXAMPLE 40

Preparation of (5)6-Methoxy-2-[[(4-methoxy-3,5-dimethyl-2-pyridinyl)-methyl]sulfinyl]-1H-benzimidazole To a 50 mL beaker was added about 1 g of (5)6-methoxy-2-[[(4methoxy-3,5-dimethyl-2-pyridinyl)-methyl]sulfinyl]-1H-benzimidazole to 30 mL of dimethylformamide (DMF) containing 1 mL of ammonium hydroxide. Additional (5)6-methoxy-2-[[(4-dimethoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under refrigerated conditions (approximately 5° C.) and a humidity range of approximately 50 to 90 percent until crystals formed (between 2–4 days). The identity of the title compound is confirmed by single crystal x-ray diffraction and/or Raman spectroscopy. The resulting material was shown to contain between about 88 and 92 percent (w/w) of the 6-methoxy-2-[[(4methoxy-3,5-dimethyl-2-pyridinyl)-methyl]sulfinyl]-1H-benzimidazole and between about 8 and 12 percent (w/w) of 5-methoxy-2-[[(4-methoxy-3,5-dimethyl-2-pyridinyl)-methyl]sulfinyl]-1H-benzimidazole.

EXAMPLE 41

Preparation of (5)6-Methoxy-2[[(4-methoxy-3,5-dimethyl-2-pyridinyl)-methyl]sulfinyl]-1H-benzimidazole To a 50 mL beaker was added about 1 g of (5)6-methoxy-2-[[(4-methoxy-3,5-dimethyl-2-pyridinyl)-methyl]sulfinyl]-1H-benzimidazole to 30 mL of ethanol containing 1 mL of ammonium hydroxide. Additional (5)6-methoxy-2-[[(4-methoxy-3,5methyl2-pyridinyl)-methyl]sulfinyl]-1H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under refrigerated conditions (approximately 5° C.) until crystals formed (between 2–6 days). The identity of the title compound is confirmed by single crystal x-ray diffraction and/or Raman spectroscopy. The resulting material was shown to contain between about 85 and 88 percent (w/w) of the 6-methoxy-2[[(4methoxy-3,5-dimethyl-2-pyridinyl)-methyl]sulfinyl]-1H-benzimidazole and between about 12 and 15 percent (w/w) of 5-methoxy-2[[(4-methoxy-3,5-dimethyl-2-pyridinyl)-methyl]sulfinyl]-1H-benzimidazole.

EXAMPLE 42

Preparation of Essentially Free 6-Methoxy-2-[[(4-methoxy-3,5-dimethyl-2-pyridinyl)-methyl]sulfinyl]-1H-benzimidazole To a 50 mL beaker was added about 1 g of (5)6-methoxy-2[[(4methoxy-3,5-dimethyl-2-pyridinyl)-methyl]sulfinyl]-1H-benzimidazole to 30 mL of dimethylformamide (DMF) containing 1 mL of ammonium hydroxide. Additional (5)6-methoxy-2-[[(4-methoxy-3,5-dimethyl-2-pyridinyl)-methyl]sulfinyl]-1H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under ambient conditions (approximately 25° C.) and a humidity range of 0 to 50 percent until crystals formed (between 1–4 days). The identity of the title compound is confirmed by single crystal x-ray diffraction and/or Raman spectroscopy. The resulting material was shown to contain between about 96 and 98 percent (w/w) of the 6-methoxy-2-[[(4-methoxy-3, dimethyl-2-pyridinyl)-methyl]sulfinyl]-1H-benzimidazole and between about 2 and 4 percent (w/w) of 5-methoxy-2-[[(4methoxy-3,5dimethyl-2-pyridinyl)-methyl]sulfinyl]-1H-benzimidazole.

EXAMPLE 43

Preparation of (5)6-Methoxy-2-[[(4-methoxy-3,5-dimethyl-2-pyridinyl)-methyl]sulfinyl]-1H-benzimidazole To a 50 mL beaker was added about 1 g of (5)6-methoxy-2-[[(4-methoxy-3,5-dimethyl-2-pyridinyl)-methyl]sulfinyl]-1H-benzimidazole to 30 mL of a 75:25 mixture of ethanol:toluene. Additional (5)6-methoxy-2[[(4methoxy-3,5-dimethyl-2-pyridinyl)-methyl]sulfinyl]-1 H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under refrigerated conditions (approximately 5° C.) and a humidity range of approximately 50 to 90 percent until crystals formed (between 4–12 days). The identity of the title compound is confirmed by single crystal x-ray diffraction and/or Raman spectroscopy. The resulting material was shown to contain between about 82 and 90 percent (w/w) of the 6-methoxy-2-[[(4-methoxy- 3,5-dimethyl-2-pyridinyl)-methyl]sulfinyl]-1H-benzimidazole and between about 10 and 18 percent (w/w) of 5-methoxy-2-[[(4methoxy-3,5-dimethyl-2-pyridinyl)-methyl]sulfinyl]-1H-benzimidazole.

EXAMPLE 44

Preparation of (5)6-Methoxy-2[[(4methoxy-3,5-dimethyl-2-pyridinyl)-methyl]sulfinyl]-1H-benzimidazole To a 50 mL beaker was added about 1 g of (5)6-methoxy-2-[[(4-methoxy-3,5-dimethyl-2-pyridinyl)-methyl]sulfinyl]-1H-benzimidazole to 30 mL of chloroform. Additional (5)6-methoxy-2-[[(4-methoxy-3,5dimethyl-2-pyridinyl)-methyl]sulfinyl]-1H-benzimidazole was added to the resulting solution until a suspension of the material was formed. The solution was stirred for approximately 10 minutes, and then filtered through a 0.45 μm Poly(tetrafluoroethylene) (PTFE) or Nylon filter. The resulting saturated solution was placed in a shallow petri dish, covered and stored under refrigerated conditions (approximately 5° C.) and a humidity range of approximately 50 to 90 percent until crystals formed (between 1–2 days). The identity of the title compound is confirmed by single crystal x-ray diffraction and/or Raman spectroscopy. The resulting material was shown to contain between about 50 and 60 percent (w/w) of the 6-methoxy-2-[[(4methoxy-3,5-dimethyl-2-pyridinyl)methyl]sulfinyl]-1H-benzimidazole and between about 40 and 50 percent (w/w) of 5-methoxy-2[[(4-methoxy-3,5dimethyl-2-pyridinyl)-methyl]sulfinyl]-1H-benzimidazole.

EXAMPLES 45–112

Examples 45–112 generally pertain to formulations of the invention comprising at least one active ingredient and at least one cyclodextrin. In these examples, bulk drug samples of 5(6)-methoxy-2[[(4-methoxy-3,5-dimethyl-2-pyridinyl)-methyl]sulfinyl]-1H-benzimidazole were sourced from Uquifa, S. A, Esteve Quimica, S. A., Cipla, Dr. Reddy's Laboratories, Ltd. Solubility studies were performed using all of the above materials. Lyophilization was performed using 5(6)-methoxy-2-[[(4-methoxy-3,5dimethyl-2-pyridinyl)-methyl]sulfinyl]-1H-benzimidazole from Dr. Reddy's Laboratories, Ltd. All other work was performed using Uquifa material including the manufacture of all clinical prototypes. Early development work, including solubility studies, lyophilization, spray drying, utilized Encapsin™ brand hydroxypropyl-beta-cyclodextrin (HPβCD) purchased from Amaizo located in Hammond, Ind. Hydroxypropyt-beta-cyrlodextrin (HPβCD) purchased from Wacker Biochem Corp of Adrian, Mich., was used in the manufacture of all clinical prototypes.

Solubilrty studies were performed by the addition of a known mass of 5(6)-methoxy-2-[[(4-methoxy-3,5-dimethyl-2-pyridinyl)-methyl]sulfinyl]1H-benzimidazole and/or HP CD to a given volume of solvent system. Solubilities were determined by observation, as the maximum concentration at which 5(6)-methoxy-2-[[(4-methoxy-3,5-dimethyl-2-pyridinyl)-methyl]sulfinyl]-1H-benzimidazole completely dissolved. Additionally, concentrations of 5(6)-methoxy-2-[[(4methoxy-3,5-dimethyl-2-pyridinyl)methyl]sulfinyl]-1H-benzimidazole and HP CD at set molar ratios were solubilized in systems of high pH (adjusted as high as 12.2, with 1N NaOH), the pH was adjusted (using 2N HCl) in a stepwise downward manner until precipitation occurred.

In addition, the general definitions, manufacturer, and manufacturer location for the following terms are provided:

| | | |
|---|---|---|
| Acesulfame-k ® | acetosulfam (sweetener) | Hoechst Celanese: Chatam, NJ |
| Aquaceat CPD 30 ® | aqueous ethylcellulose dispensant | FMC Corporation; Philadelphia, PA |
| Avicel PH 102 ® | microcrystalline cellulose | FMC Corporation; Philadelphia, PA |
| Cab-o-Sil ® | colloidal silicon dioxide | Cabot Corporation Rancho Santo Margarita, CA |
| Eudragit L-30 D-55 ® (USPNF) | type B of aqueous latex dispersion of methylacrylic acid polymer | Rohm America; Piscataway, NJ |
| Eudragit L 30D ® | aqueous latex dispension of F100 | Rohm America Piscataway, NJ |
| Eudragit L-30 D-55 ® | aqueous latex dispension of methylacrylic acid copolymer type C | Rohm America Piscataway, NJ |
| Fastflo ® | lactose 316 | Foremost Company; San Francisco, CA |
| Opadry Clean ® | hydroxypropylmethyl-cellulose and polyethylene glycol (plasticizer) | Colorcon: West Point, PA |
| Opadry White ® | hydroxypropylmethylcellulose polyethylene glycol (plasticizer), and titanium dioxide | Colorcon; West Point, PA |

EXAMPLE 45

Preparation of a Solution Containing Hydroxypropyl-beta-cyclodextrin and 5(6)-Methoxy-2-[[(4-methoxy-3,5-dimethyl-2-pyridinyl)-methyl]sulfinyl]-1H-benzimidazole A solution containing hydroxypropyl-betacyclodextdn (HPβCD) and 5(6)-methoxy-2[[(4-methoxy-3,5-dimethyl-2-pyridinyl)-methyl]sulfinyl]-1H-benzimidazole was prepared as follows. 30 g of HPβCD was weighed and added to 50 mL of water to dissolve therein. 5 g of 5(6)-methoxy-[[(4-methoxy-3,5-dimethyl-2-pyridinyl)-methyl]sulfinyl]-1H-benzimidazole was thereafter added to the cyclodextrin solution. A 1 M sodium hydroxide solution was added until all of the 5(6)-methoxy-2-[[(4-methoxy-3,5-dimethyl-2-pyridinyl)-methyl]sulfinyl]-1H-benzimidazole was in solution (approximate pH was 11.7). The pH was then adjusted to 10.0 with 1M hydrochloric acid solution and water was added to achieve a final volume of 100 mL. The resulting solution, prepared at 5 percent (w/v) 5(6)-methoxy-2-[[(4-methoxy-3,5-dimethyl-2-pyridinyl)-methyl]sulfinyl]-1H-benzimidazole and 30 percent (w/v) HPβCD, was found to be stable for at least six days with little discoloration, as set forth in the following table.

| | Percent Active Ingredient | |
|---|---|---|
| Day | 5° C. | Ambient Temperature |
| 1 | 99.9% | 101.0% |
| 2 | 98.9% | 97.7%* |
| 3 | 98.8% | 98.7%** |

*solution was pale brown/red color
**solution was deep brown color

EXAMPLE 46

Lyophilization of a Solution Containing Hydroxypropyl-beta-cyclodextrin and 5(6)-Methoxy-2[[(4-methoxy-3,5-dimethyl-2-pyridinyl)-methyl]sulfinyl]-1H-benzimidazole A lyophilzation procedure was carned out using 200 mL of a solution of combined HPβCD/5(6)-methoxy-2

[[(4methoxy-3,5-dimethyl-2pyridinyl)-methyl]sulfinyl]-1H-benzimidazole of 17.5 percent (w/v) and a 5(6)-methoxy-2-[[(4-methoxy-3,5-dimethyl-2-pyridinyl)-methyl]sulfinyl]1H-benzimidazole to HPβCD mass ratio of 1:6.

EXAMPLE 47

Lyophilization of a Solution Containing Hydroxypropyl-beta-cyclodextrin and 5(6)-Methoxy-2-[[(4-methoxy-3,5-dimethyl-2-pyridinyl)-methyl]sulfinyl]-1H-benzimidazole A lyophilzation procedure was carried out using 1345 mL of a solution of combined HPβCD/5(6)-methoxy-2 [[(4methoxy-3,5-dimethyl-2-pyridinyl)-methyl]sulfinyl]-1H-benzimidazole of 3 percent (w/v) and a 5(6)-methoxy-2-[[(4-methoxy-3 5dimethyl-2-pyridinyl)-methyl]sulfinyl]-1H-benzimidazole to HPβCD mass ratio of 1:6.8. The solution was prepared by dissolving 5.1 g of 5(6)-methoxy-2-[[(4-methoxy-3,5-dimethyl-2-pyridinyl)-methyl]sulfinyl]-1H-benzimidazole in 19 mL of a 40 percent solution of tetraethanolamine (TEA) and thereafter adding 1361 mL of a 2.3% (w/v) solution of HPβCD.

EXAMPLE 48

Spray Drying a Solution Containing Hydroxypropyl-beta-cyclodextrin and 5(6)-Methoxy-2-[[(4-methoxy-3,5-dimethyl-2-pyridinyl)-Methyl]sulfinyl]-1H-benzimidazole 2000 mL of a complexed solution of 5(6)-methoxy-2-[[(4-methoxy-3,5-dimethyl-2-pyridinyl)-methyl]sulfinyl]-1H-benzimidazole and HPβCD was prepared according to Example 45 with a combined HPβCD/5(6)-methoxy-2-[[(4methoxy-3,5-dimethyl-2-pyridinyl)-methyl]sulfinyl]-1H-benzimidazole (w/v) of 17.5 percent and a 5(6)-methoxy-2-[[(4methoxy-3,5-dimethyl-2pyridinyl)-methyl]sulfinyl]-1H-benzimidazole to HPβCD mass ratio of 1:6. This solution was spray dried using a Spray Drier, Model GB-21 made commercially available by Yamato located in Tokyo, Japan.

EXAMPLE 49

Spray Granulation of a Solution Containing Hydroxypropyl-beta-cyclodextrin and 5(6)-Methoxy-2-[[(4-methoxy-3,5-dimethyl-2-pyridinyl)-methyl]sulfinyl]-1H-benzimidazole 2000 to 6000 mL of a complexed solution of 5(6)-methoxy-2[[(4-methoxy-3,5-dimethyl-2-pyridinyl)-methyl]sulfinyl]-1H-benzimidazole and HPβCD was prepared according to Example 41 with a combined HPβCD/5(6)-methoxy-2-[[(4methoxy-3,5-dimethyl-2-pyridinyl)-methyl]sulfinyl]-1H-benzimidazole (w/v) ranging from 17.5 to 35.0 percent and a 5(6)-methoxy-2-[[(4-methoxy-3,5dimethyl-2-pyridinyl)-methyl]sulfinyl]-1H-benzimidazole to HPβCD mass ratio of 1:6. The complexed solution was top sprayed onto lactose 316 in a MP-1 Multi Processor made commercially available by Niro-Aeromatic located in Columbia, Md. at product temperature of 40° C. and an initial spray rate of 11 g/min, with a total spray time of 8 hours.

EXAMPLE 50

Compact Preparation of a Solid Material Containing Hydroxypropyl-beta-cyclodextrin and 5 (6)-Methoxy-2[[(4-methoxy-3,5-dimethyl-2-pyridinyl)-methyl]sulfinyl]-1H-benzimidazole Solid complexed material prepared according to the lyophilization procedure of Example 46 was used to prepare various compacts. The compacts were prepared in approximately 10 mg strengths. An excipient compatibility study was carried out with the study being set up as a fractional factorial design with independent variables which include: complex type, type of bulking agent (lactose vs. mannitol), tablet size (120 mg, 140 mg, and 16 mg), and level of colloidal silicon dioxide (0 percent, 0.5 percent, and 1.0 percent). 70 mg of the complexed material was compressed into compacts of 120 mg, 140 mg, and 160 mg containing 20 percent Avicel PH 102®, 2.0 percent Acesulfame-K, and either Lactose 316 or granular mannitol as the bulking agent. Compacts were prepared with and without Cab-O-Sil L90®. These materials were sieved, blended, and pressed into compacts using 9/32", plain, smooth, concave tolling on a Korsch PH 100 Tablet Press made commercially available by Korsch Pressen GmbH of Berlin, Germany, turned manually.

EXAMPLE 51

Compact Preparation of a Solid Material Containing Hydroxypropyl-beta-cyclodextrin and 5 (6)-Methoxy-2[[(4-methoxy3,5-dimethyl-2-pyridinyl)-methyl]sulfinyl]-1H-benzimidazole The procedure according to Example 50 was repeated using the solid complexed material prepared according to the lyophilization procedure of Example 47.

EXAMPLES 52–75

Tablet Preparation of a Solid Material Containing Hydroxypropyl-beta-cyclodextrin and 5(6)-Methoxy-2-[[(4methoxy-3,5-dimethyl-2-pyridinyl)-methyl]sulfinyl]-1H-benzimidazole These examples were carried out with solid complexed material at an 5(6)-methoxy-2-[[(4-methoxy-3,5-dimethyl-2-pyridinyl)-methyl]sulfinyl]-1H-benzimidazole to HPβCD mass ratio of 1:6. Three prototype cores were prepared at approximately 10 mg strengths of 5(6)-methoxy-2-[[(4methoxy-3,5-dimethyl-2-pyridinyl)-methyl]sulfinyl]-1H-benzimidazole from both sprayed onto lactose and lyophilization complex material (complex without TEA). This material was milled with a Quadro Comil (0.024 inch round screen) and combined with either Lactose 316 or Avicel PH 102, Acesulfame-K, (all prescreened through a #20 screen) and blended in a 4-quart v-blender for 9 minutes (3 without intensifier, 3 with intensifier, and 3 without intensifier). Magnesium stearate was screened through a #20 screen, added to the blend and blended for 2 minutes. The blends were transferred to a Korsch PH100 or Key DB-16 tablet press and compressed to a target weight of 160 mg with a target hardness of approximately 8 to 10 kP, using 9/32 inch round piain/plain concave tooling. Each of the core tablets was coated in a NIP-1 Multi Processor made commercially availabe by Niro-Aeromatic of Columbia, Md. with a Wurster column insert. Tablets were undercoated with Opadry Clear (Colorcon YS-1-7472). After drying, a portion of each core prototype was coated with a solution containing Eudragit L-30 D-55 or Aquaccat CPD-30. Prototype formulas and coating solutions are set forth in the foregoing tables. The prototypes were prepared at 20 mg strengths from a sprayed on lactose complex using Lactose 316 as the bulking agent Tablets were manufactured as described above and undercoated with Opadry White® (Colorcon YS-1-7003). After drying, core prototypes were coated with a solution containing Eudragit L-30 D-55.

Stability sample packages for initial prototypes consisted of 10 mg and 20 mg tablets contained in a 60 cc white HDPE bottle, with a polypropylene cap with an induction seal and polyester coil. Bottles were stored at 40° C. with 75 percent relative humidity, 25° C. with 60 percent relative humidity and 5° C.

|  | Prototype Formulas | | | | | |
|---|---|---|---|---|---|---|
|  | 10 mg core tablets | | | | 20 mg core tablets | |
| Formulation | A | B | C | K | L | M |
| Lyophilization Complex | 43.75% | | | | | |
| Sprayed on Lactose | | 87.50% | 87.50% | 50.90% | 95.80% | 95.80% |
| Lactose 316 | 32.75% | 9.75% | | 46.35% | 1.45% | 1.45% |
| Avicel PH 102 | 20.00% | | 9.75% | | | |
| Acesulfame K | 2.00% | 2.00% | 2.00% | 2.00% | 2.00% | 2.00% |
| Magnesium | 0.50% | 0.50% | 0.50% | 0.50% | 0.50% | 0.50% |
| Cabosil | 1.00% | 0.25% | 0.25% | 0.25% | 0.25% | 0.25% |
| Total | 100% | 100% | 100% | 100% | 100% | 100% |

| Formulation | mg/tablet D | mg/tablet E | mg/tablet F | mg/tablet G | mg/tablet H |
|---|---|---|---|---|---|
| Core Component | | | | | |
| Active Ingredient | 10.0 | 10.0 | 10.0 | 10.0 | 10.0 |
| HP CD | 60.0 | 60.0 | 60.0 | 60.0 | 60.0 |
| Lactose 316 | 52.4 | 55.6 | 85.6 | 52.4 | 85.6 |
| Avicel PH 102 | 32.0 | 32.0 | | | |
| Acesulfame K | 3.2 | 3.2 | 3.2 | 3.2 | 3.2 |
| Magnesium Stearate | 0.8 | 0.8 | 0.8 | 0.8 | 0.8 |
| Colloidal Silicon Dioxide | 1.6 | 0.4 | 0.4 | 1.5 | 0.4 |
| Core Total | 160 | 160 | 160 | 160 | 160 |
| Coating Component | | | | | |
| Opadry Clear | 4.8 | 4.8 | 4.8 | 4.8 | 9.6 |
| Eudragit L 30 D 55 | 16.8 | 24.0 | 24.0 | | |
| Aquacoat CPD | | | | 9.1 | 17.5 |
| Talc | 16.8 | 24.0 | 24.0 | | |
| Triethyl Citrate | 3.4 | 4.8 | 1.3 | 1.9 | 3.5 |
| Total (mg) | 201.8 | 217.6 | 214.1 | 175.8 | 190.7 |

| Formulaton | mg/tablet I | mg/tablet J | mg/tablet N | mg/tablet O |
|---|---|---|---|---|
| Core Component | | | | |
| Active Ingredient | 10.0 | 10.0 | 20.0 | 20.0 |
| HP CD | 60.0 | 60.0 | | 142.9 |
| Lactose 316 | 70.0 | 52.4 | 143.6 | 2.5 |
| Avicel PH 102 | 15.6 | 32.0 | | |
| Acesulfame K | 3.2 | 3.2 | 3.4 | 3.4 |
| Magnesium Stearate | 0.8 | 0.8 | 0.9 | 0.9 |
| Colloidal Silicon Dioxide | 0.4 | 1.6 | 0.4 | 0.4 |
| Croscarmellose Sodium | | | 117 | |
| Core Total | 160 | 160 | 170 | 170 |
| Coating Component | | | | |
| Opadry Clear | 10.4 | 8.0 | | |
| Opadry White | | | | 7.7 |
| L 30 D 55 | | | | 7.8 |
| Aquacoat CPD | 19.0 | 15.6 | | |
| Talc | | | | 7.8 |

| -continued | | | |
|---|---|---|---|
| Triethyl Citrate | 3.7 | 3.0 | 1.5 |
| Total (mg) | 193.1 | 186.6 | 194.8 |

| Coating Solution Formulations | |
|---|---|
| Opadry Clear Coat | % |
| Opadry Clear | 5.0 |
| Purified Water | 95.0 |
| Total | 100.0 |
| Opadry White Coating | % |
| Opadry Clear | 12.0 |
| Purified Water | 88.0 |
| Total | 100.0 |
| Eudragit L30 D55 | % |
| Eudragit L 30 D | 30.3 |
| Talc | 9.1 |
| Triethyl Citrate | 1.8 |
| Purified Water | 58.8 |
| Total | 100.0 |
| Aquacoat CPD-30 | % |
| Aquacoat CPD-30 | 55.7 |
| Triethyl Citrate | 3.3 |
| Purified Water | 41.0 |
| Total | 100.0 |

EXAMPLES 76–80

Preparation of Clinical Prototypes of a Solid Material Containing Hydroxypropyl-beta-cyclodextrin and 5(6)-Methoxy-2-[[(4-methoxy-3,5-dimethyl-2-pyridinyl)-methyl]sulfinyl]-1H-benzimidazole Clinical prototypes were manufactured by complexing 5(6)-methoxy-2-[[(4-methoxy-3,5-dimethyl-2-pyridinyl)-methyl]sulfinyl]-1H-benzimidazole ("active ingredient") with HPβCD in solution and spraying the solution onto lactose. The spray on lactose material was then blended with excipients listed in the below table and compressed into core tablets. The mass ratios of 5(6)-methoxy-2-[[(4-methoxy-3,5-dimethyl-2-pyridinyl)-methyl]sulfinyl]1H-benzimidazole to HPβCD ranged from 1:4 to 1:20 with core tablet weights of 170 mg to 550 mg, respectively as set forth in the table below.

| | Quantitative Formulas of Core Tablets | | | | |
|---|---|---|---|---|---|
| Component | 1:4 mg/tablet | 1:6 mg/tablet | 1:10 mg/tablet | 1:15 mg/tablet | 1:20 mg/tablet |
| Active Ingredient | 20.0 | 20.0 | 20.0 | 20.0 | 20.0 |
| HRβCD | 80.0 | 120.0 | 200.0 | 300.0 | 400.0 |
| Lactose 316 | 68.7 | 28.7 | 53.7 | 228.7 | 128.7 |
| Magnesium Stearate | 0.9 | 0.9 | 0.9 | 0.9 | 0.9 |
| Colloidal Silicon Dioxide | 0.4 | 0.4 | 0.4 | 0.4 | 0.4 |
| Total (mg) | 170.0 | 170.0 | 275.0 | 550.0 | 550.0 |

All tablets were coated to a 4.5 percent total solids weight gain with an Opadry White coating solution as a subcoat. After drying, a 10 percent total solids weight gain from an Eudragit L 30 or D-55 coating solution was applied as an enteric coat The stability of the sample packages for clinical prototypes consisted of 20 mg tablets contained in a 60 cc white HDPE bottle, with a polypropylene CRC cap with an induction seal and a polyester coil. Bottles were stored at 40° C. with 75 percent relative humidity, 30° C. with 60 percent relative humidity, 25° C. with 60 percent relative humidity, and 5° C.

EXAMPLES 81–85

Preparation of Clinical Prototypes of a Solid Material Containing Hydroxypropyl-beta-cyclodextrin and 5(6)-Methoxy-2-[[(4-methoxy-3,5-dimethyl-2-pyridinyl)-methyl]sulfinyl]-1H-benzimidazole The procedure according to Examples 76–80 was repeated except that a 15 percent total solids weigh gain from an Eudragit FS 30 D (previously known as Eudragit Preparation 4110D) coating solution was applied as an enteric coat.

EXAMPLE 86

Solubility Assessment

The solubility of 5(6)-methoxy-2-[[(4-methoxy-3,5-dimethyl-2-pyridinyl)-methyl]sulfinyl]-1H-benzimidazole was assessed as a function of HPβCD concentration in water. 5(6)-methoxy-2[[(4-methoxy-3,5dimethyl-2-pyridinyl)-methyl]sulfinyl]-1H-benzimidazole was found to have an aqueous solubility in water of approximately 0.3 mg/mL (09 mM). In general, the solubility of the active ingredient is influenced by solution pH. Solubility was found to increase linearly as a function of HPβCD concentration.

EXAMPLE 87

Solubility Assessment

The procedure according to Example 86 was repeated except that water with a borate buffer (pH of 8) was employed. Solubility was found to increase linearly as a function of HPβCD concentration.

EXAMPLE 88

Solubility Assessment

The procedure according to Example 86 was repeated except that water with a phosphate buffer (pH of 11) was employed. Solubility was found to increase linearly as a function of HPβCD concentration.

EXAMPLES 89–98

Prototypes of 5(6)-Methoxy-2-[[(4-methoxy-3,5-dimethyl-2-pyridinyl)-methyl]sulfinyl]-1H-benzimidazole and HPβCD Prototype formulations of 10 mg cores 5(6)-methoxy-2-[[(4-methoxy-3,5-dimethyl-2-pyridinyl)-methyl]sulfinyl]-1H-benzimidazole ("active ingredient") were prepared using either lactose or Avicel as the bulking agent. Formulations are presented in the table set forth in Example 52–75 under "Prototype Formulations". Physical characterzations are presented in the table hereinbelow. No significant differences in processing were observed for any of the formulations. All formulas were compresse to approximately 7 kP hardness, containing about 4.6 percent moisture, and disintegrated in less than 11 minutes.

Physical Characteristics of Initial 10 mg Prototypes
10 mg formulations of Active Ingredient

| Formulation | Weight (g) | Thickness (in) | Hardness (kp) | Disintegration* (min) | Moisture (%) |
|---|---|---|---|---|---|
| A | 0.1576 (0.005) | 0.152 (0.004) | 7.0 (0.47) | 10:35 (:16) | 4.63 |
| B | 0.163 (0.004) | 0.153 (0.003) | 6.6 (0.71) | 8:01 (:15) | 4.73 |
| C | 0.1649 (0.003) | 0.156 (0.002) | 6.8 (0.50) | 8:56 (:20) | 4.65 |
| D | 0.1985 (0.005) | NT | NT | 26:29, ¹SIF (:49) | 3.3 |
| E | 0.2042 (0.006) | NT | NT | 30:21, SIF (:37) | 3.74 |
| F | 0.1984 (0.004) | NT | NT | 25:05, SIF (:40) | 3.8 |
| G | 0.1755 (0.004) | NT | NT | NT | NT |
| H | 0.182 (0.005) | NT | NT | 12:28, SIF (:50) | 4.03 |
| I | 0.1922 (0.005) | NT | NT | 15:50, SIF (:55) | 4.24 |
| J | 0.1826 (0.003) | NT | NT | 15:22, SIF (:31) | 4.2 |
| K | 0.1582 (0.001) | 0.139 (0.0005) | 11.5 (2.7) | 10:20 (:29) | 4.88 |

NT = not tested
*Disintegration media is water unless otherwise indicated
¹Disintegration in Simulated Intestinal Fluid (SIF) preceeded by 1 hr in Simulated Gastric Fluid (SGF)
Numbers in parentheses are standard deviations

EXAMPLES 95–101

Prototypes of 5(6)-Methoxy2-[[(4-methoxy-3,5-dimethyl-2-pyridinyl)-methyl]sulfinyl]-1H-benzimidazole and HPβCD Initial 20 mg core prototypes were manufactured with only lactose as a bulking agent They were compressed with mean hardnesses of 8.7 and 16.5 kP (16.5 kP hardness required approximately 3000 lbs. of compression force). Mean disintegration times were less than 8 minutes for both prototypes. Moisture levels were found to be 5.14 percent and 5.64 percent as set forth in the below table.

An Opadry White undercoat with Eudragit L 30 D-55 as the enteric coat was used for the 20 mg tablets strengths. This system showed the least or no discoloration and was used for clinical prototypes.

Physical Characteristics of Initial 20 mg Prototypes
20 mg Active Ingredient Formulations

| Formulation | Weight (g) | Thickness (in) | Hardness (kp) | Disintegration* (min) | Moisture (%) |
|---|---|---|---|---|---|
| L | 0.1683 (0.005) | 0.151 (0.0004) | 8.7 (1.1) | 8:00 (:22) | 5.14 (0.01) |
| M | 0.1674 (0.0007) | 0.155 (0.0005) | 16.5 (1.6) | 7:21 (:10) | 5.64 |
| N | 0.1713 (0.002) | NT | 7.2 (2.3) | 5:16 (:40) | NT+ |
| O | 0.1691 | NT | NT | 10:56, SIF (:15) | NT |

NT = not tested
*Disintegration media is water unless otnerwise indicated
¹Disintegration in Simulated Intestinal Fluid (SIF) proceeded by 1 hr in Simulated Gastric Fluid (SGF)
Numbers in parentheses are standard deviations

EXAMPLES 102–106

Dissolution of Prototypes of 5(6)-Methoxy-2-[[(4-methoxy-3,5-dimethyl-2-pyridinyl)-methyl]sulfinyl]-1H-benzimidazole and HPβCD Dissolutions of various prototypes set forth in Examples 81–85 were determined and compared against a Prilosec® formulation in the form of a capsule containing enteric coated granules. The Prilosec formulation contained no cyclodextrins. The dissolution was conducted for 60 minutes in acid followed by 60 minutes in pH 7.4 buffer. The prototypes of the invention having 5(6)-methoxy-2-[[(4-methoxy-3,5-dimethyl-2pyridinyl)-methyl]sulfinyl]-1H-Benzimidazole to HPβCD mass ratios of 1:4 and 1:6 displayed dissolution behavior comparable to the Prilosec® formulation.

EXAMPLES 107–109

Bioavailability Assessment ($C_{max}$, AUC, and $T_{max}$)

Fasted-state bioavailability studies were conducted in normal healthy subjects (six subjects per study) comparing three formulations of the present invention to Prilosec® in a 2-way crossover design. All formulations were administered as a single 20 mg dose immediately following an overnight fast. Blood was collected at 0.0, 0.5, 1.0, 1.5, 2.0, 2.5, 3.0, 3.5, 4.0, 5.0, 6.0, 7.0, 8.0 hours in the study, with additional collections being made at hours 10 and 12. The studies were conducted comparing three 20 mg tablets to Prilosec. The comparison consisted of 6 different subjects, with three formulations containing active ingredient to HPβCD mass ratios of 1:6, 1:6, 1:10, and coatings of Eudragit FS3OD, L3OD, and L3OD, respectively (denoted respectively as formulations A, B, and C). The formulations of the invention generally displayed improved bioavailability relative to the innovator formulation (i.e., Prilosec) as set forth in the following table.

| | Bioavailability Study Results | | |
|---|---|---|---|
| Formulation | $C_{max}$* | AUC* | $T_{max}$ |
| A | +28% | +6% | 5.8 hrs (vs 2.0 for the innovator) |
| B | +14% | +13% | 2.2 hrs (vs 1.4 for the innovator) |
| C | +60% | +11% | 2.8 hrs (vs 2.4 for the innovator) |

EXAMPLES 110–112

Bioavailability Assessment ($C_{max}$, AUC, and $T_{max}$)

The procedure according to Examples 107–109 was repeated except that these studies was conducted in 47 subjects, 15 or 16 subjects per study received one of three 20 mg tablets containing active ingredient to HPβCD mass ratios of 1:4, 1:15, 1:20, denoted as formulations D, E, and F respectively. All tablets were coated with Eudragit L3OD. All 47 subjects received Prilosec. Blood collections were not made at the 10 and 12 hour marks.

The formulations of the invention generally displayed improved bioavailability relative to the innovator formulation (i.e., Prilosec) as set forth in the following table.

| | Bioavailability Study Results | | |
|---|---|---|---|
| Formulation | $C_{max}$* | AUC* | $T_{max}$ |
| D | +116% | +30% | 2.0 hrs (vs 2.2 for the innovator) |
| E | +54% | +19% | 2.4 hrs (vs 2.0 for the innovator) |
| F | +73% | +23% | 1.9 hrs (vs 1.9 for the innovator) |

The examples and embodiments as set forth in the detailed description are for illustrative purposes only and do not limit the scope of the invention as defined by the claims.

EXAMPLE 113

Enteric Coated Tablet

A formulation employing an active ingredient is made according to the following recipe:

| | g |
|---|---|
| Core Material | |
| Active Ingredient | 225 |
| Mannitol | 1425 |
| Hydroxypropyl cellulose | 60 |
| Microcrystalline cellulose | 40 |
| Anhydrous lactose | 80 |
| Sodium lauryl sulfate | 5 |
| Dibasic sodium phosphate dihydrate | 8 |
| Purified water | 350 |
| Separating Layer | |
| Core material | 300 |
| Hydroxypropyl cellulose | 30 |
| Talc | 51 |
| Magnesium stearate | 4 |
| Water | 600 |
| Enteric Coating Layer | |
| Pellets covered with separating layer | 279 |
| Methacrylic acid copolymer | 140 |
| Triethyl citrate | 42 |
| Mono-and diglycerides | 7 |
| Polysorbate 80 | 0.7 |
| Water | 300 |
| Tablets | |
| Enteric coating layered pellets | 352 |
| Microcrystalline cellulose | 1,052 |
| Sodium Stearyl fumarate | 3 |

Sodium lauryl sulfate is dissolved in purified water to form a granulation liquid. The active ingredient along with the other dry ingredients used in making the core are dry mixed. The granulation liquid is added to the powder mixture and the resulting mass is kneaded and granulated to a proper consistency.

The wet mass is forced through an extruder equipped with screens. The extrudate is spheronized in a spheronizing apparatus. The core material is dried in a fluid bed dryer and classified into a suitable particle range. The prepared core material is covered with a separating layer in a fluid bed apparatus with a hydroxypropyl methylcellulose solution containing talc and magnesium stearate.

The enteric coating layer is sprayed onto the pellets covered with the separating layer from an aqueous dispersion of methacrylic acid copolymer, mono- and diglycerides, triethyl citrate, and polysorbate in a fluid bed apparatus.

Enteric coating layered pellets, microcrystalline cellulose and sodium stearyl fumarate are mixed and compressed into tablets using a rotary tableting machine.

EXAMPLE 114

Tablet

A tablet is formed from the following ingredients:

| Ingredient | g |
|---|---|
| active ingredient | 400–430 |
| lactose, anhydrous | 1,400–1,420 |
| polyvinylpyrrolodine | 100 |
| sodium carbonate, anhydrous | 15 |
| methyl cellulose | 12 |
| distilled water | 200 |
| magnesium stearate | 30 |

The active ingredient, lactose, polyvinylpyrrolidone, and sodium carbonate are homogenized and granulated by the addition of the methyl cellulose and distilled water. The wet mass is dried in a fluidized bed drier using an inlet air temperature of +50° C. for 30 minutes. The dried mixture is then forced through a sieve with an aperture of 0.5 mm. After mixing with magnesium stearate, the granulate is tableted on a tableting machine using 6 mm punches. The tablet weight is 100 mg. The tablet may optionally be coated with the separating layer and/or enteric coating as described in Example 113.

That which is claimed:

1. A granulated blend comprising per dosage unit an amount of active pharmaceutical ingredient within the range from about 5 mg to about 60 mg of 6-methoxy-2-[[(4-methoxy-3,5-dimethyl-2-pyridinyl)methyl]sulfinyl]-1H-benzimidazole, or one or more pharmaceutically acceptable salts, solvates, hydrates, or combinations thereof, in pure form, and at least one pharmaceutically acceptable carrier, diluent, or excipient, wherein said 6-methoxy-2-[[(4-methoxy-3,5-dimethyl-2-pyridinyl)methyl]sulfinyl]-1H-benzimidazole in said pharmaceutical formulation remains pure or is essentially free of 5-methoxy-2-[[(4-methoxy-3,5-dimethyl-2-pyridinyl)methyl]sulfinyl]-1H-benzimidazole, said pharmaceutical formulation in unit dosage form being adapted for oral administration in the form of a capsule or tablet.

2. A granulated blend according to claim 1 in a form suitable for administration to treat gastric acid related diseases in mammals.

3. A granulated blend according to claim 1 wherein said amount of active ingredient in said per dosage unit dosage is selected from the group consisting of about 10 mg, 20 mg, and 40 mg.

4. A granulated blend comprising per dosage unit an amount of active pharmaceutical ingredient within the range from about 5 mg to about 60 mg of 6-methoxy-2-[[(4-methoxy-3,5-dimethyl-2-pyridinyl)methyl]sulfinyl]-1H-benzimidazole, or one or more pharmaceutically acceptable salts, solvates, hydrates, or combinations thereof, which is essentially free of 5-methoxy-2-[[(4-methoxy-3,5-dimethyl-2-pyridinyl)methyl]sulfinyl]-1H-benzimidazole, and at least one pharmaceutically acceptable carrier, diluent, or excipient, wherein said 6-methoxy-2-[[(4-methoxy-3,5-dimethyl-2-pyridinyl)methyl]sulfinyl]-1H-benzimidazole in said pharmaceutical formulation remains essentially free of said 5-methoxy-2-[[(4-methoxy-3,5-dimethyl-2-pyridinyl)methyl]sulfinyl]-1H-benzimidazole, said pharmaceutical formulation in unit dosage form being adapted for oral administration in the form of a capsule or tablet.

5. A granulated blend according to claim 1 in a form suitable for administration to treat gastric acid related diseases in mammals.

6. A granulated blend according to claim 1 wherein said amount of active ingredient in said per dosage unit dosage is selected from the group consisting of about 10 mg, 20 mg, and 40 mg.

7. A granulated blend comprising per dosage unit an amount of active pharmaceutical ingredient within the range from about 5 mg to about 60 mg of a composition comprising 6-methoxy-2-[[(4-methoxy-3,5-dimethyl-2-pyridinyl)methyl]sulfinyl]-1H-benzimidazole, and, optionally, 5-methoxy-2-[[(4-methoxy-3,5-dimethyl-2-pyridinyl)methyl]sulfinyl]-1H-benzimidazole or one or more pharmaceutically acceptable salts, solvates, hydrates, or combinations thereof, and at least one pharmaceutically acceptable carrier, diluent, or excipient, wherein the ratio of said composition of 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl)methyl]sulfinyl]-1-H-benzimidazole in said formulation is essentially the same as the ratio of said 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl)methyl]sulfinyl]-1H-benzimidazole in the active pharmaceutical ingredient used in said pharmaceutical formulation, said formulation in unit dosage form being adapted for oral administration in the form of a capsule or tablet.

8. A granulated blend according to claim 7 in a form suitable for administration to treat gastric acid related diseases in mammals.

9. A granulated blend according to claim 7 wherein said amount of active ingredient in said per dosage unit dosage is selected from the group consisting of about 10 mg, 20 mg, and 40 mg.

10. A granulated blend according to claim 7 comprising a non-toxic, therapeutically effective amount of 6-methoxy-2-[[(4-methoxy-3,5-dimethyl-2-pyridinyl)methyl]sulfinyl]-1H-benzimidazole, in pure form, or one or more pharmaceutically acceptable salts, solvates, hydrates, or combinations thereof, and at least one pharmaceutically acceptable carrier, diluent, or excipient.

11. A granulated blend according to claim 7 comprising a non-toxic, therapeutically effective amount of 6-methoxy-2-[[(4-methoxy-3,5-dimethyl-2-pyridinyl)methyl]sulfinyl]-1H-benzimidazole, which is essentially free of 5-methoxy-2-[[(4-methoxy-3,5-dimethyl-2-pyridinyl)methyl]sulfinyl]-1H-benzimidazole, or one or more pharmaceutically acceptable salts, solvates, hydrates, or combinations thereof, and at least one pharmaceutically acceptable carrier, diluent, or excipient.

12. A granulated blend according to claim 7 comprising a non-toxic, therapeutically effective amount of a composition of 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl)methyl]sulfinyl]-1H-benzimidazole or one or more pharmaceutically acceptable salts, solvates, hydrates, or combinations thereof, and at least one pharmaceutically acceptable carrier, diluent, or excipient, wherein the amount of said 6-methoxy-2-[[(4-methoxy-3,5-dimethyl-2-pyridinyl)methyl]sulfinyl]-1H-benzimidazole in said composition is present at a concentration less than about 83 percent (w/w).

13. A granulated blend according to claim 7 comprising a non-toxic, therapeutically effective amount of a composition of 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl)methyl]sulfinyl]-1H-benzimidazole or one or more pharmaceutically acceptable salts, solvates, hydrates, or combinations thereof, and at least one pharmaceutically acceptable carrier, diluent, or excipient, wherein the amount of said 6-methoxy-2-[[(4-methoxy-3,5-dimethyl-2-pyridinyl)methyl]sulfinyl]-1H-benzimidazole in said composition is present at a concentration greater than about 89 percent (w/w).

14. A granulated blend according to claim 1, wherein said granulation is a wet granulation or a dry granulation.

15. A granulated pharmaceutical formulation in unit dosage form comprising per dosage unit an amount of active pharmaceutical ingredient within the range from about 5 mg to about 60 mg of 6-methoxy-2-[[(4-methoxy-3,5-dimethyl-2-pyridinyl)methyl]sulfinyl]-1H-benzimidazole, or one or more pharmaceutically acceptable salts, solvates, hydrates, or combinations thereof, in pure form, and at least one pharmaceutically acceptable carrier, diluent, or excipient, wherein said 6-methoxy-2-[[(4-methoxy-3,5-dimethyl-2-pyridinyl)methyl]sulfinyl]-1H-benzimidazole in said pharmaceutical formulation remains pure or is essentially free of 5-methoxy-2-[[(4-methoxy-3,5-dimethyl-2-pyridinyl) methyl]sulfinyl]-1H-benzimidazole, said pharmaceutical formulation in unit dosage form being adapted for oral administration in the form of a capsule or tablet.

16. A pharmaceutical formulation according to claim 15 wherein said capsule or tablet is enterically coated.

17. A pharmaceutical formulation according to claim 16 in a form adapted for administration to treat gastric acid related diseases in mammals.

18. A pharmaceutical formulation according to claim 16 wherein said amount of active ingredient in said unit dosage form is selected from the group consisting of about 10 mg, 20 mg, and 40 mg.

19. A granulated pharmaceutical formulation in unit dosage form comprising per dosage unit an amount of active pharmaceutical ingredient within the range from about 5 mg to about 60 mg of 6-methoxy-2-[[(4-methoxy-3,5-dimethyl-2-pyridinyl)methyl]sulfinyl]-1H-benzimidazole, or one or more pharmaceutically acceptable salts, solvates, hydrates, or combinations thereof, which is essentially free of 5-methoxy-2-[[(4-methoxy-3,5-dimethyl-2-pyridinyl) methyl]sulfinyl]-1H-benzimidazole, and at least one pharmaceutically acceptable carrier, diluent, or excipient, wherein said 6-methoxy-2-[[(4-methoxy-3,5-dimethyl-2-pyridinyl)methyl]sulfinyl]-1H-benzimidazole in said pharmaceutical formulation remains essentially free of said 5-methoxy-2-[[(4-methoxy-3,5-dimethyl-2-pyridinyl) methyl]sulfinyl]-1H-benzimidazole, said pharmaceutical formulation in unit dosage form being adapted for oral administration in the form of a capsule or tablet.

20. A pharmaceutical formulation according to claim 19 wherein said capsule or tablet is enterically coated.

21. A pharmaceutical formulation according to claim 20 in a form adapted for administration to treat gastric acid related diseases in mammals.

22. A pharmaceutical formulation according to claim 20 wherein said amount of active ingredient in said unit dosage form is selected from the group consisting of about 10 mg, 20 mg, and 40 mg.

23. A granulated pharmaceutical formulation in unit dosage form comprising per dosage unit an amount of active pharmaceutical ingredient within the range from about 5 mg to about 60 mg of a composition comprising 6-methoxy-2-[[(4-methoxy-3,5-dimethyl-2-pyridinyl)methyl]sulfinyl]-1H-benzimidazole, and, optionally, 5-methoxy-2-[[(4-methoxy-3,5-dimethyl-2-pyridinyl)methyl]sulfinyl]-1H-benzimidazole or one or more pharmaceutically acceptable salts, solvates, hydrates, or combinations thereof, and at least one pharmaceutically acceptable carrier, diluent, or excipient, wherein the ratio of said composition of 6-methoxy-2-[[(4-methoxy-3,5-dimethyl-2-pyridinyl) methyl]sulfinyl]-1H-benzimidazole and 5-methoxy-2-[[(4-methoxy-3,5-dimethyl-2-pyridinyl)methyl]sulfinyl]-1H-benzimidazole in said formulation is essentially the same as the ratio of said 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl) methyl]sulfinyl]-1H-benzimidazole in the active pharmaceutical ingredient used in said pharmaceutical formulation, said formulation in unit dosage form being adapted for oral administration in the form of a capsule or tablet.

24. A pharmaceutical formulation according to claim 23 wherein said capsule or tablet is enterically coated.

25. A pharmaceutical formulation according to claim 24 a form adapted for administration to treat gastric acid related diseases in mammals.

26. A pharmaceutical formulation according to claim 25 wherein said amount of active ingredient in said unit dosage form is selected from the group consisting of about 10 mg, 20 mg, and 40 mg.

27. A granulated pharmaceutical formulation according to claim 23 comprising a non-toxic, therapeutically effective amount of 6-methoxy-2-[[(4-methoxy-3,5-dimethyl-2-pyridinyl)methyl]sulfinyl]-1-benzimidazole, in pure form, or one or more pharmaceutically acceptable salts, solvates, hydrates, or combinations thereof, and at least one pharmaceutically acceptable carrier, diluent, or excipient.

28. A granulated pharmaceutical formulation according to claim 23 comprising a non-toxic, therapeutically effective amount of 6-methoxy-2-[[(4-methoxy-3,5-dimethyl-2-pyridinyl)methyl]sulfinyl]-1H-benzimidazole, which is essentially free of 5-methoxy-2-[[(4-methoxy-3,5-dimethyl-2-pyridinyl)methyl]sulfinyl]-1H-benzimidazole, or one or more pharmaceutically acceptable salts, solvates, hydrates, or combinations thereof, and at least one pharmaceutically acceptable carrier, diluent, or excipient.

29. A granulated pharmaceutical formulation according to claim 23 comprising a non-toxic, therapeutically effective amount of a composition of 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl) methyl]sulfinyl]-1H-benzimidazole or one or more pharmaceutically acceptable salts, solvates, hydrates, or combinations thereof, and at least one pharmaceutically acceptable carrier, diluent, or excipient, wherein the amount of said 6-methoxy-2-[[(4-methoxy-3,5-dimethyl-2-pyridinyl) methyl]sulfinyl]-1H-benzimidazole in said composition is present at a concentration less than about 83 percent (w/w).

30. A granulated pharmaceutical formulation according to claim 23 comprising a non-toxic, therapeutically effective amount of a composition of 6-methoxy-2-[[(4-methoxy-3,5-dimethyl-2-pyridinyl)methyl]sulfinyl]-1H-benzimidazole and 5-methoxy-2-[[(4-methoxy-3,5-dimethyl-2-pyridinyl) methyl]sulfinyl]-1H-benzimidazole or one or more pharmaceutically acceptable salts, solvates, hydrates, or combinations thereof, and at least one pharmaceutically acceptable carrier, diluent, or excipient, wherein the amount of said 6-methoxy-2-[[(4-methoxy-3,5-dimethyl-2-pyridinyl) methyl]sulfinyl]-1H-benzimidazole in said composition is present at a concentration greater than about 89 percent (w/w).

31. A method of essentially maintaining the desired active ingredient ratio of a composition comprising 6-methoxy-2-[[(4-methoxy-3,5-dimethyl-2-pyridinyl)methyl]sulfinyl]-1H-benzimidazole and, optionally 5-methoxy-2-[[(4- methoxy-3,5-dimethyl-2-pyridinyl)methyl]sulfinyl]-1H-benzimidazole or one or more pharmaceutically acceptable salts, solvates, hydrates, or combinations thereof, in a pharmaceutical formulation compared to the ratio of said 6-methoxy-2-[[(4-methoxy-3,5-dimethyl-2-pyridinyl) methyl]sulfinyl]-1H-benzimidazole and 5-methoxy-2-[[(4-methoxy-3,5-dimethyl-2-pyridinyl)methyl]sulfinyl]-1H-benzimidazole in the active pharmaceutical ingredient used in said pharmaceutical formulation comprising mechanically manipulating said composition of active pharmaceutical ingredient with at least one pharmaceutically acceptable carrier, diluent or excipient.

32. A method according to claim 31, wherein said 6-methoxy-2-[[(4-methoxy-3,5-dimethyl-2-pyridinyl) methyl]sulfinyl]-1H-benzimidazole is present in pure form.

33. A method according to claim 31, wherein said 6-methoxy-2-[[(4-methoxy-3,5-dimethyl-2-pyridinyl) methyl]sulfinyl]-1H-benzimidazole is essentially free of 5-methoxy-2-[[(4-methoxy-3,5-dimethyl-2-pyridinyl) methyl]sulfinyl]-1H-benzimidazole.

34. A method according to claim 31, wherein said 6-methoxy-2-[[(4-methoxy-3,5-dimethyl-2-pyridinyl) methyl]sulfinyl]-1H-benzimidazole is present in said composition at a concentration less than about 83 percent (w/w).

35. A method according to claim 31, wherein said 6-methoxy-2-[[(4-methoxy-3,5-dimethyl-2-pyridinyl) methyl]sulfinyl]-1H-benzimidazole is present in said composition at a concentration greater than about 89 percent (w/w).

36. A method according to claim 31, wherein said mechanical manipulation is grinding.

37. A method according to claim 31, wherein said mechanical manipulation is sieving.

38. A method of essentially maintaining the desired active ingredient ratio of a composition comprising 6-methoxy-2-[[(4-methoxy-3,5-dimethyl-2-pyridinyl)methyl]sulfinyl]-1H-benzimidazole and, optionally 5-methoxy-2-[[(4-methoxy-3,5-dimethyl-2-pyridinyl)methyl]sulfinyl]-1H-benzimidazole or one or more pharmaceutically acceptable salts, solvates, hydrates, or combinations thereof, in a pharmaceutical formulation compared to the ratio of said 6-methoxy-2-[[(4-methoxy-3,5-dimethyl-2-pyridinyl) methyl]sulfinyl]-1H-benzimidazole and 5-methoxy-2-[[(4-methoxy-3,5-dimethyl-2-pyridinyl)methyl]sulfinyl]-1H-benzimidazole in the active pharmaceutical ingredient used in said pharmaceutical formulation comprising granulating said composition of active pharmaceutical ingredient with at least one phamarceutically acceptable carrier, diluent or excipient.

39. A method according to claim 38, wherein said 6-methoxy-2-[[(4-methoxy-3,5-dimethyl-2-pyridinyl) methyl]sulfinyl]-1H-benzimidazole is present in pure form.

40. A method according to claim 38, wherein said 6-methoxy-2-[[(4-methoxy-3,5-dimethyl-2-pyridinyl) methyl]sulfinyl]-1H-benzimidazole is essentially free of 5-methoxy-2-[[(4-methoxy-3,5-dimethyl-2-pyridinyl) methyl]sulfinyl]-1H-benzimidazole.

41. A method according to claim 38, wherein said 6-methoxy-2-[[(4-methoxy-3,5-dimethyl-2-pyridinyl) methyl]sulfinyl]-1H-benzimidazole is present in said composition at a concentration less than about 83 percent (w/w).

42. A method according to claim 38, wherein said 6-methoxy-2-[[(4-methoxy-3,5-dimethyl-2-pyridinyl) methyl]sulfinyl]-1H-benzimidazole is present in said composition at a concentration greater than about 89 percent (w/w).

43. A method according to claim 38, wherein said granulation is a wet granulation.

44. A method according to claim 38, wherein said granulation is a dry granulation.

45. A method according to claim 38, wherein said granulation is essentially a dry granulation.

* * * * *

UNITED STATES PATENT AND TRADEMARK OFFICE
CERTIFICATE OF CORRECTION

PATENT NO.     : 6,653,329 B1
DATED          : November 25, 2003
INVENTOR(S)    : Whittle et al.

It is certified that error appears in the above-identified patent and that said Letters Patent is hereby corrected as shown below:

Column 50,
Lines 38-40, delete "Preparation of (5)6-methoxy-2-[[(4methoxy-5-dimethyl-2pyridinyl)methyl]sulfinyl]-1H-benzimidazole" and insert -- Preparation of (5)6-methoxy-2-[[(4-methoxy-3,5-dimethyl-2-pyridinyl)methyl]sulfinyl]-1$H$-benzimidazole --

Column 51,
Lines 37-39, delete "Preparation of 6(6)-Methoxy-2[[(4-methoxy-3,5-dimethyl-2-pyridinyl)-methyl]sulfinyl]-1-benzimidazole Isomers" and insert -- Preparation of 5(6)-methoxy-2-[[(4-methoxy-3,5-dimethyl-2-pyridinyl)-methyl]sulfinyl]-1$H$-benzimidazole isomers --

Column 52,
Lines 41-43, delete "Preparation of (5)6-Methoxy-2-[[(4-methoxy-3,6-dimethyl-2-pyridinyl)-methyl]sulfinyl]-1H-benzimidazole" and insert -- Preparation of (5)6-methoxy-2-[[(4-methoxy-3,5-dimethyl-2-pyridinyl)-methyl]sulfinyl]-1$H$-benzimidazole --

Column 59,
Lines 7-9, delete "Preparation of (6)6-Methoxy-2-[[(4-methoxy-3,5-dimethyl-2-pyridinyl)-methyl]sulfinyl]-1H-benzimidazole" and insert -- Preparation of (5)6-methoxy-2-[[(4-methoxy-3,5-dimethyl-2-pyridinyl)-methyl]sulfinyl]-1$H$-benzimidazole --

Column 66,
Amend the following section as shown:

Core Component

| | | | | | |
|---|---|---|---|---|---|
| Active Ingredient | 10.0 | 10.0 | 10.0 | 10.0 | 10.0 |
| HPβCD | 60.0 | 60.0 | 60.0 | 60.0 | 60.0 |
| Lactose 316 | 52.4 | 85.6 | 85.6 | 52.4 | 85.6 |
| Avicel PH 102 | 32.0 | | | 32.0 | |
| Acesulfam K | 3.2 | 3.2 | 3.2 | 3.2 | 3.2 |
| Magnesium Stearate | 0.8 | 0.8 | 0.8 | 0.8 | 0.8 |
| Colloidal Silicon Dioxide | 1.6 | 0.4 | 0.4 | 1.6 | 0.4 |
| Core Total | 160 | 160 | 160 | 160 | 160 |

UNITED STATES PATENT AND TRADEMARK OFFICE
CERTIFICATE OF CORRECTION

PATENT NO. : 6,653,329 B1
DATED : November 25, 2003
INVENTOR(S) : Whittle et al.

It is certified that error appears in the above-identified patent and that said Letters Patent is hereby corrected as shown below:

Column 66 (cont'd),
Amend the following section as shown:

Core Component

| | | | | |
|---|---|---|---|---|
| Active Ingredient | 10.0 | 10.0 | 20.0 | 20.0 |
| HPβCD | 60.0 | 60.0 | | 142.9 |
| Lactose 316 | 70.0 | 52.4 | 143.6 | 2.5 |
| Avicel PH 102 | 15.6 | 32.0 | | |
| Acesulfame K | 3.2 | 3.2 | 3.4 | 3.4 |
| Magnesium Stearate | 0.8 | 0.8 | 0.9 | 0.9 |
| Colloidal Silicon Dioxide | 0.4 | 1.6 | 0.4 | 0.4 |
| Croscarmellose Sodium | | 1.7 | | |
| Core Total | 160 | 160 | 170 | 170 |

Column 67,
Amend the following section as shown:

Quantitative Formulas of Core Tablets

| Component | 1:4 mg/tablet | 1:6 mg/tablet | 1:10 mg/tablet | 1:15 mg/tablet | 1:20 mg/tablet |
|---|---|---|---|---|---|
| Active Ingredient | 20.0 | 20.0 | 20.0 | 20.0 | 20.0 |
| HPβCD | 80.0 | 120.0 | 200.0 | 300.0 | 400.0 |
| Lactose 316 | 68.7 | 28.7 | 53.7 | 228.7 | 128.7 |
| Magnesium Stearate | 0.9 | 0.9 | 0.9 | 0.9 | 0.9 |
| Colloidal Silicon Dioxide | 0.4 | 0.4 | 0.4 | 0.4 | 0.4 |
| Total (mg) | 170.0 | 170.0 | 275.0 | 550.0 | 550.0 |

UNITED STATES PATENT AND TRADEMARK OFFICE
CERTIFICATE OF CORRECTION

PATENT NO.    : 6,653,329 B1
DATED         : November 25, 2003
INVENTOR(S)   : Whittle et al.

It is certified that error appears in the above-identified patent and that said Letters Patent is hereby corrected as shown below:

Column 73,
Line 65, delete "claim 1" and insert -- claim 4 --

Column 74,
Line 1, delete "claim 1" and insert -- claim 4 --

Signed and Sealed this

Twenty-fourth Day of August, 2004

JON W. DUDAS
*Director of the United States Patent and Trademark Office*